US008653111B2

(12) United States Patent
Thede et al.

(10) Patent No.: US 8,653,111 B2
(45) Date of Patent: *Feb. 18, 2014

(54) SUBSTITUTED DIHYDROPYRAZOLONES FOR TREATING CARDIOVASCULAR AND HEMATOLOGICAL DISEASES

(75) Inventors: Kai Thede, Berlin (DE); Ingo Flamme, Reichshof (DE); Felix Oehme, Wuppertal (DE); Jens-Kerim Ergüden, Wülfrath (DE); Friederike Stoll, Düsseldorf (DE); Joachim Schuhmacher, Wuppertal (DE); Hanno Wild, Wuppertal (DE); Peter Kolkhof, Wuppertal (DE); Hartmut Beck, Köln (DE); Jörg Keldenich, Wuppertal (DE); Metin Akbaba, Ratingen (DE); Mario Jeske, Solingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/356,256

(22) Filed: Jan. 23, 2012

(65) Prior Publication Data

US 2012/0121727 A1    May 17, 2012

Related U.S. Application Data

(63) Continuation of application No. 12/447,192, filed as application No. PCT/EP2007/008877 on Oct. 12, 2007.

(30) Foreign Application Priority Data

Oct. 26, 2006 (DE) .......................... 10 2006 050 516

(51) Int. Cl.
*A61K 31/4439* (2006.01)
*C07D 401/14* (2006.01)

(52) U.S. Cl.
USPC ........................................ 514/341; 546/272.7

(58) Field of Classification Search
USPC ........................................ 514/341; 546/272.7
See application file for complete search history.

(56) References Cited

U.S. PATENT DOCUMENTS

| | | | |
|---|---|---|---|
| 6,121,305 A | 9/2000 | Obara et al. | |
| 8,067,407 B2 * | 11/2011 | Jeske et al. | 514/211.15 |
| 2003/0083351 A1 | 5/2003 | Almstead et al. | |
| 2006/0067927 A1 | 3/2006 | Chandrasekaran et al. | |
| 2006/0160826 A1 | 7/2006 | Ghanbari et al. | |
| 2010/0035906 A1 | 2/2010 | Flamme et al. | |
| 2010/0093803 A1 | 4/2010 | Thede et al. | |
| 2010/0305085 A1 | 12/2010 | Thede et al. | |

FOREIGN PATENT DOCUMENTS

| | | |
|---|---|---|
| CA | 2608099 A1 | 11/2006 |
| CA | 2667392 | 2/2008 |
| JP | 10306077 | 11/1998 |
| WO | 02/092573 A2 | 11/2002 |
| WO | 03/051833 A2 | 6/2003 |
| WO | 2004/052284 | 6/2004 |
| WO | 2004/087066 | 10/2004 |
| WO | 2004/089303 A2 | 10/2004 |
| WO | 2005/030121 | 4/2005 |
| WO | 2007/008541 A2 | 1/2007 |

OTHER PUBLICATIONS

S.P. Singh et al.: "Reaction of 1-[5-Hydroxy-3-Methyl-1-(2-Thiazolyl)-4-Pyrazolyl]-1,3-Butanediones with Phenyl and Heterocyclic Hydrazines: a Convienient Syntheses of 4,5-Bipyrazoles," Indian Journal of Heterocyclic Chemistry, Jul.-Sep. 1993, 3: 5-8.

J. Elguero et al.: "A 1H and 13C NMR Study of the Structure and Tautomerism of 4-Pyrazolylprazolinones," J. Heterocyclic Chem., May-Jun. 1990, 27: 865-870.

H. Barth er al.: "Konstitution and Synthese des Muscafavins," Liebigs Ann. Chem., 1981, pp. 2164-2179.

R.A. Evans er al.—Trifluromethyl-substituted Dehydrodizepines and Cyanopyrroles form Azido-/Tetrazolo-pyridines, J Chem. Commun., 1992, 15: 1062-1064.

F. Oehme et al.: "A Nonradioactive 96-well Plate Assay for the Detection of Hypozia-Inducible Factor Prolyl Hydroxylase Activity," Analytical Biochemistry, 2004, 330: 74-80.

F. Oehme et al.: "Overexpression of PH-4, a Novel Putative Proline 4-Hydroxylase, Modulates Activity of Hypoxia-Inducible Transcription Factors," Biochemical and Biophysical Research Communications, 2002, 296: 343-349.

C.A. Heid et al.: "Real Time Quantative PCR," Genome Research, 1996, 6(10): 986-994.

N. Yokoyama et al.: Synthesis and Structure-Activity Relationships of Oxamic Acid and Acetic Acid Derivatives Released to L-Thyronine,: J. Med. Chem., 1995, 38:695-707.

N. Sperber er al.: "Parasympathetic Blocking Agernt, III. N-Alkylpiperidinecarboxylic Esters," J. Am. Chem. Soc, 1959, 81: 704-709.

M.A. Meziane et al.: "A New Route to 1-Oxo-1,2-Dihydropyrimido[1,6-a]Benzimidazole-4-Carboxylates from Ethyl 2-(Benzimidazol-2-yl)-3-(Dimethylamino)Acrylate Using Solvent-Free Conditions," Synthesis, Jul. 1996, pp. 967-969.

Vippagunta et al., "Crystalline Solids," Advanced Drug Delivery Reviews, 2001, 48: 3-26.

West, "Solid Solutions," 1988, Chapter 10, pp. 358 and 365.

(Continued)

*Primary Examiner* — Samantha Shterengarts
(74) *Attorney, Agent, or Firm* — Karen B. King

(57) ABSTRACT

The present application relates to novel substituted dihydropyrazolone derivatives, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

14 Claims, No Drawings

(56) References Cited

OTHER PUBLICATIONS

Ulrich, "Crystallization: 4. Crystal Characteristics," Kirk-Othmer Encyclopedia of Chemical Technology, Aug. 2002.

R.I Dowell et al.: Novel Inhibitore of Prolyl 4-hydroxylase: Part 4. Pyridine-2-Carboxylic Acid Analogues with Alternative 2-Substituents,: Eur. J. Med. Chem, 1993, 25:513-516.

Hill et al. "Inhibition of TRPM2 channels by the antifungal agents clotrimazole and econazole," Naunyn Schmiedebergs Arch. Pharmacol, 2004, 370: 277-238, abstract only.

U.S. Appl. No. 11/919,478, filed Oct. 30, 2009.

U.S. Appl. No. 12/447,201, filed Oct. 26, 2007.

U.S. Appl. No. 12/447,207, filed Dec. 21, 2009.

Philipp et al., "Stabilization of hypoxia inducible factor rather than modulcation of collagen metabolism improves cardiac function after acute myocardial infarction in rats," European Journal of Heart Failure, 2006, 8:347-354.

Ivan, "HIF_Prolyl hydroxylase in hibitors: From basic science to clinical trials," Maedica—a Journal of Clinical Medicine, 2006, 1(2): 67-69.

* cited by examiner

SUBSTITUTED DIHYDROPYRAZOLONES FOR TREATING CARDIOVASCULAR AND HEMATOLOGICAL DISEASES

The present application relates to novel substituted dihydropyrazolone derivatives, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

A deficient supply of oxygen to the human organism or its components which either impairs regular functioning of the organism or its components due to its duration and/or its extent or causes its functioning to break down completely is called hypoxia. Hypoxia can be caused by a reduction in the available oxygen in the air breathed in (e.g. during periods at a high altitude), by disorders in external respiration (e.g. as a result of disturbed functioning of the lungs or obstruction of the respiratory tract), by a reduction in the cardiac output (e.g. in the event of cardiac insufficiency, acute right ventricular overloading with pulmonary embolism), by too low an oxygen transport capacity of the blood (e.g. as a result of an anemia or intoxication, e.g. with carbon monoxide), locally demarcated by a reduced blood flow as a result of vascular occlusions (ischaemia states typically e.g. of the heart, the lower extremities or the brain, diabetic macro- and microangiopathy) or also by an increased oxygen requirement of the tissue (e.g. as a result of increased muscular work or local inflammations) [Eder, Gedigk (ed.), *Allgemeine Pathologie und pathologische Anatomie*, 33rd ed., Springer Verlag, Berlin, 1990]

The human organism is capable to a limited extent of adapting acutely and chronically to situations of reduced oxygen supply. In addition to an immediate response, which includes inter alia an increase in the cardiac output and respiratory output and a local dilation of blood vessels by vegetative-nervous control mechanisms, hypoxia brings about a change in the transcription of numerous genes. The function of the gene products here serves to compensate the oxygen deficiency. Thus, expression of several enzymes of glycolysis and glucose transporter I is enhanced, as a result of which anaerobic ATP production increases and survival of the oxygen deficiency is rendered possible [Schmidt, Thews (ed.), *Physiologie des Menschen*, 27th ed., Springer Verlag, Berlin, 1997; Löffler, Petrides (ed.), *Biochemie und Pathobiochemie*, 7th ed., Springer Verlag, Berlin, 2003].

Hypoxia furthermore leads to enhanced expression of vascular endothelial cell growth factor, VEGF, as a result of which regeneration of blood vessels (angiogenesis) is stimulated in hypoxic tissues. The blood flow through ischaemic tissue is thereby improved in the long term. This counter-regulation is evidently only very inadequate in the case of various cardiovascular diseases and vascular occlusion diseases [overview in: Simons and Ware, *Therapeutic angiogenesis in cardiovascular disease*, Nat. Rev. Drug. Discov. 2 (11), 863-71 (2003)].

Furthermore, in cases of systemic hypoxia expression of the peptide hormone erythropoietin formed predominantly in the interstitial fibroblasts of the kidneys is enhanced. The formation of red blood cells in the bone marrow is thereby stimulated, and the oxygen transport capacity of the blood is therefore increased. This effect has been and is used by high-performance athletes in so-called high altitude training. A decrease in the oxygen transport capacity of the blood e.g. as a result of anemia after hemorrhaging usually causes an increase in erythropoietin production in the kidney. With certain forms of anemia, this regulatory mechanism may be disturbed or its normal value may be set lower. Thus e.g. in patients suffering from renal insufficiency, erythropoietin is indeed produced in the kidney parenchyma, but in significantly reduced amounts with respect to the oxygen transport capacity of the blood, which results in so-called renal anemia. Renal anemia in particular, but also anemias caused by tumors and HIV infection are conventionally treated by parenteral administration of recombinant human erythropoietin (rhEPO). No alternative therapy with an orally available medicament currently exists for this expensive therapy [overview in: Eckardt, *The potential of erythropoietin and related strategies to stimulate erythropoiesis*, Curr. Opin. Investig. Drugs 2(8), 1081-5 (2001); Berns, *Should the target hemoglobin for patients with chronic kidney disease treated with erythropoietic replacement therapy be changed?*, Semin. Dial. 18 (1), 22-9 (2005)]. Recent studies demonstrate that, in addition to its erythropoiesis-increasing action, erythropoietin also has a protective (anti-apoptotic) action on hypoxic tissue, in particular the heart and the brain, which is independent thereof. Furthermore, according to recent studies therapy with erythropoietin reduces the average severity of morbidity in patients with cardiac insufficiency [overviews in: Caiola and Cheng, *Use of erythropoietin in heart failure management*, Ann. Pharmacother. 38 (12), 2145-9 (2004); Katz, *Mechanisms and treatment of anemia in chronic heart failure*, Congest. Heart. Fail. 10 (5), 243-7 (2004)].

The genes described above which are induced by hypoxia have the common feature that the increase in their expression under hypoxia is caused by so-called hypoxia-inducible transcription factor (HIF). HIF is a heterodimeric transcription factor which comprises an alpha and a beta subunit. Three HIF alpha isoforms are described, of which HIF-1 alpha and HIF-2 alpha are highly homologous and are of importance for hypoxia-induced gene expression. While the beta subunit (of which 2 isoforms have been described), which is also called ARNT (aryl hydrocarbon receptor nuclear translocator), is expressed constitutively, expression of the alpha subunit depends on the oxygen content in the cell. Under normoxia, the HIF alpha protein is poly-ubiquitinized and then degraded proteasomally. Under hypoxia this degradation is inhibited, so that HIF alpha dimerizes with ARNT and can activate its target genes. The HIF dimer bonds here to so-called hypoxia-responsive elements (HRE) in the regulatory sequences of its target genes. The HRE are defined by a consensus sequence. Functional HRE have been detected in the regulatory elements of numerous hypoxia-induced genes [overviews in: Semenza, *Hypoxia-inducible factor 1: oxygen homeostasis and disease pathophysiology*, Trends Mol. Med. 7 (8), 345-50 (2001); Wenger and Gassmann, *Oxygen(es) and the hypoxia-inducible factor*-1, Biol. Chem. 378 (7), 609-16 (1997)].

The molecular mechanism on which this regulation of HIF alpha is based has been clarified by the works of several independent groups of researchers. The mechanism is conserved from species to species: HIF alpha is hydroxylated by a subclass of oxygen-dependent prolyl 4-hydroxylases, called PHD or EGLN, on two specific prolyl radicals (P402 and P564 of the human HIF-1 alpha subunit). The HIF prolyl 4-hydroxylases are iron-dependent, 2-oxoglutarate-converting dioxygenases [Epstein et al., *C. elegans EGL-9 and mammalian homologs define a family of dioxygenases that regulate HIF by prolyl hydroxylation*, Cell 107 (1), 43-54 (2001); Bruick and McKnight, *A conserved family of prolyl-4-hydroxylases that modify HIF*, Science 294 (5545), 1337-40 (2001); Ivan et al., *Biochemical purification and pharmacological inhibition of a mammalian prolyl hydroxylase acting on hypoxia-inducible factor*, Proc. Natl. Acad. Sci. U.S.A. 99

(21), 13459-64 (2002)]. The enzymes were annotated as prolyl hydroxylases for the first time in 2001 [Aravind and Koonin, *The DNA-repair protein AlkB, EGL-9, and leprecan define new families of 2-oxoglutarate- and iron-dependent dioxygenases*, Genome Biol. 2 (3), research0007.1-0007.8, Epub 2001 Feb. 19].

The pVHL tumor suppressor protein, which together with elongin B and C forms the so-called VBC complex, which adapts the HIF alpha subunit to an E3 ubiquitin ligase, bonds to the prolyl-hydroxylated HIF alpha subunit. Since the prolyl 4-hydroxylation of the HIF alpha subunit and its subsequent degradation takes place as a function of the intracellular concentration of oxygen, HIF prolyl 4-hydroxylases have also been called a cellular oxygen sensor. Three isoforms of these enzymes have been identified: EGLN1/PHD2, EGLN2/PHD1 and EGLN3/PHD3. Two of these enzymes (EGLN2/PHD1 and EGLN3/PHD3) are induced transcriptionally even under hypoxia and are possibly responsible for the lowering of the HIF alpha levels to be observed under chronic hypoxia [overview in: Schofield and Ratcliffe, *Oxygen sensing by HIF hydroxylases*, Nat. Rev. Mol. Cell. Biol. 5 (5), 343-54 (2004)].

Selective pharmacological inhibition of HIF prolyl 4-hydroxylases brings about the increase in the gene expression of HIF-dependent target genes and is therefore beneficial for the therapy of numerous disease syndromes. In the case of diseases of the cardiovascular system in particular, an improvement in the course of the diseases is to be expected from induction of new blood vessels and the change in the metabolic situation of ischaemic organs from aerobic to anaerobic ATP production. An improvement in the vascularization of chronic wounds promotes the healing process, especially in the case of poorly healing ulcera cruris and other chronic skin wounds. The induction of endogenous erythropoietin in certain disease forms, in particular in patients with renal anemia, is likewise a therapeutic goal to be aimed for.

The HIF prolyl 4-hydroxylase inhibitors described hitherto in the scientific literature do not meet the requirements to be imposed on a medicament. These are either competitive oxoglutarate analogues (such as e.g. N-oxalylglycine), which are characterized by their very low action potency, and therefore in in vivo models have as yet shown no action in the sense of an induction of HIF target genes. Or they are iron-complexing agents (chelators), such as desferroxamine, which act as non-specific inhibitors of iron-containing dioxygenases and, although they bring about an induction of the target genes, such as e.g. erythropoietin, in vivo, evidently counteract erythropoiesis by complexing of the available iron.

The object of the present invention is to provide novel compounds which can be employed for treatment of diseases, in particular cardiovascular and hematological diseases.

In the context of the present invention, compounds are now described which act as specific inhibitors of HIF prolyl 4-hydroxylases and on the basis of this specific action mechanism bring about in vivo, after parenteral or oral administration, the induction of HIF target genes, such as e.g. erythropoietin, and the biological processes thereby caused, such as e.g. erythropoiesis.

2-Heteroaryl-4-aryl-1,2-dihydropyrazolones having a bactericidal and/or fungicidal action are disclosed in EP 165 448 and EP 212 281. The use of 2-heteroaryl-4-aryl-1,2-dihydropyrazolones as lipoxygenase inhibitors for treatment of respiratory tract, cardiovascular and inflammatory diseases is claimed in EP 183 159. 2,4-Diphenyl-1,2-dihydropyrazolones having a herbicidal activity are described in DE 2 651 008. The preparation and pharmacological properties of certain 2-pyridyl-1,2-dihydropyrazolones are reported in *Helv. Chim. Acta* 49 (1), 272-280 (1966). WO 96/12706, WO 00/51989 and WO 03/074550 claim compounds having a dihydropyrazolone partial structure for treatment of various diseases, and hydroxy- or alkoxy-substituted bipyrazoles for treatment of neuropsychiatric diseases are disclosed in WO 2006/101903. Heteroaryl-substituted pyrazole derivatives for treatment of pain and various CNS diseases are furthermore described in WO 03/051833 and WO 2004/089303. WO 2006/114213 has meanwhile disclosed 2,4-dipyridyl-1,2-dihydropyrazolones as inhibitors of HIF prolyl 4-hydroxylases.

The x-ray crystal structure of the compound 3-methyl-1-(pyridin-2-yl)-4-(1-pyridin-2-yl-3-methyl-1H-pyrazol-5-yl)-2H-3-pyrazolin-5(1H)-one (other name: 5,5'-dimethyl-2, 2'-di-pyridin-2-yl-1',2'-dihydro-2H, 3'H-3,4'-bipyrazol-3'-one) is reported in *Acta Crystallogr., Section E: Structure Reports Online* E57 (11), o1126-o1127 (2001) [*Chem. Abstr.* 2001:796190]. The synthesis of certain 3',5-dimethyl-2-phenyl-1'-(1,3-thiazol-2-yl)-1'H, 2H-3,4'-bipyrazol-5'-ol derivatives is described in *Indian J. Heterocyclic Chem.* 3 (1), 5-8 (1993) [*Chem. Abstr.* 1994:323362]. The preparation and tautomerism of individual 4-(pyrazol-5-yl)-pyrazolin-5-one derivatives is reported in *J. Heterocyclic Chem.* 27 (4), 865-870 (1990) [*Chem. Abstr.* 1991:428557]. A therapeutic use has not hitherto been described for the compounds mentioned in these publications. The compound 2-tert-butyl-1'-[4-(4-chlorophenyl)-1,3-thiazol-2-yl]-3',5-dimethyl-1'H, 2H-3,4'-bipyrazol-5'-ol is listed as a test example in WO 2007/008541.

The present invention provides compounds of the general formula (I)

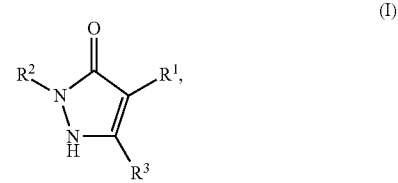

in which
R¹ represents a heteroaryl group of the formula

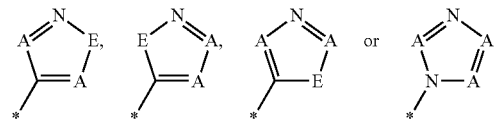

wherein
\* denotes the linkage point with the dihydropyrazolone ring,
A in each individual occurrence denotes C—R⁴ or N, wherein at most two ring members A represent N at the same time, and
E denotes O, S or N—R⁵,
R² represents a heteroaryl group of the formula

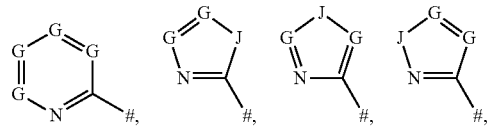

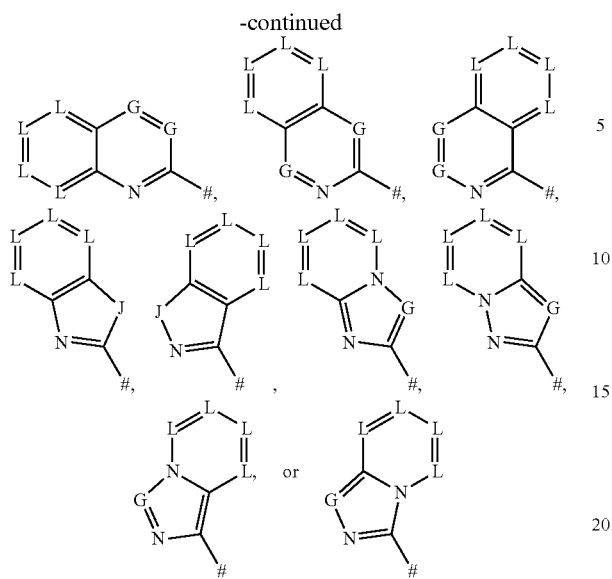

wherein # denotes the linkage point with the dihydropyrazolone ring,

G in each individual occurrence denotes C—$R^6$ or N, wherein at most two ring members G represent N at the same time, J denotes O, S or N—$R^7$ and L in each individual occurrence denotes C—$R^8$ or N, wherein at most two ring members L represent N at the same time, wherein $R^4$, $R^6$ and $R^8$ are identical or different and in each individual case, independently of one another, represent hydrogen or a substituent chosen from the series consisting of halogen, cyano, nitro, ($C_1$-$C_6$)-alkyl, ($C_3$-$C_7$)-cycloalkyl, 4- to 10-membered heterocycloalkyl, phenyl, 5- or 6-membered heteroaryl, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein (i) ($C_1$-$C_6$)-alkyl in its turn can be substituted once to three times in an identical or different manner by radicals chosen from the series consisting of halogen, cyano, oxo, ($C_3$-$C_7$)-cycloalkyl, 4- to 10-membered heterocycloalkyl, phenyl, 5- or 6-membered heteroaryl, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the cycloalkyl, heterocycloalkyl, phenyl and heteroaryl radicals mentioned last in their turn can in each case be substituted up to three times in an identical or different manner by halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and/or ($C_1$-$C_4$)-alkoxycarbonyl, (ii) ($C_3$-$C_7$)-cycloalkyl, 4- to 10-membered heterocycloalkyl, phenyl and 5- or 6-membered heteroaryl in their turn can in each case be substituted once to three times in an identical or different manner by radicals chosen from the series consisting of ($C_1$-$C_6$)-alkyl, halogen, cyano, oxo, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the alkyl radical mentioned last can in its turn be substituted up to three times in an identical or different manner by halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_7$)-cycloalkyl, 4- to 7-membered heterocycloalkyl, phenyl and/or 5- or 6-membered heteroaryl, (iii) $R^9$, $R^{10}$, $R^{11}$, $R^{13}$, $R^{14}$, $R^{17}$, $R^{19}$, $R^{21}$, $R^{24}$, $R^{25}$, $R^{26}$, $R^{28}$, $R^{29}$ and $R^{30}$ independently of one another for each individual occurrence represent a radical chosen from the series consisting of hydrogen, ($C_1$-$C_6$)-alkyl, ($C_3$-$C_7$)-cycloalkyl, 4- to 10-membered heterocycloalkyl, phenyl and 5- or 6-membered heteroaryl, wherein ($C_3$-$C_7$)-cycloalkyl, 4- to 10-membered heterocycloalkyl, phenyl and 5- or 6-membered heteroaryl in their turn can in each case be substituted up to three times in an identical or different manner by halogen, cyano, ($C_1$-$C_4$)-alkyl, tri-fluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and/or ($C_1$-$C_4$)-alkoxy-carbonyl and ($C_1$-$C_6$)-alkyl can be substituted once to three times in an identical or different manner by halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_7$)-cycloalkyl, 4- to 7-membered heterocycloalkyl, phenyl and/or 5- or 6-membered heteroaryl, (iv) $R^{12}$, $R^{15}$, $R^{16}$, $R^{18}$, $R^{20}$, $R^{22}$, $R^{23}$, $R^{23}$, $R^{27}$ and $R^{31}$ independently of one another for each individual occurrence represent a radical chosen from the series consisting of hydrogen and ($C_1$-$C_6$)-alkyl, wherein ($C_1$-$C_6$)-alkyl can be substituted once to three times in an identical or different manner by halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and/or ($C_1$-$C_4$)-alkoxycarbonyl, and/or wherein (v) $R^{11}$ and $R^{12}$, $R^{14}$ and $R^{15}$, $R^{16}$ and $R^{17}$, $R^{18}$ and $R^{19}$, $R^{20}$ and $R^{21}$, $R^{21}$ and $R^{22}$, $R^{23}$ and $R^{24}$, $R^{26}$ and $R^{27}$ and $R^{30}$ and $R^{31}$ in each case paired together with the atoms to which they are bonded can form a 5- or 6-membered heterocycloalkyl ring, which can be substituted once to three times in an identical or different manner by halogen, cyano, ($C_1$-$C_4$)-alkyl, trifluoromethyl, hydroxyl, ($C_1$-$C_4$)-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl, and $R^5$ and $R^7$ are identical or different and independently of one another represent hydrogen or a substituent chosen from the series consisting of $(C_1-C_6)$-alkyl, $(C_3-C_7)$-cycloalkyl, 4- to 7-membered heterocycloalkyl, phenyl and 5- or 6-membered heteroaryl, wherein (i) $(C_1-C_6)$-alkyl in its turn can be substituted once to three times in an identical or different manner by radicals chosen from the series consisting of halogen, cyano, oxo, $(C_3-C_7)$-cycloalkyl, 4- to 7-membered heterocycloalkyl, phenyl, 5- or 6-membered heteroaryl, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the cycloalkyl, heterocycloalkyl, phenyl and heteroaryl radicals mentioned last in their turn can in each case be substituted up to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl, and (ii) $(C_3-C_7)$-cycloalkyl, 4- to 7-membered heterocycloalkyl, phenyl and 5- or 6-membered heteroaryl in their turn can in each case be substituted once to three times in an identical or different manner by radicals chosen from the series consisting of $(C_1-C_6)$-alkyl, halogen, cyano, oxo, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the alkyl radical mentioned last in its turn can be substituted up to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and/or 5- or 6-membered heteroaryl, wherein (a) $R^9$, $R^{10}$, $R^{11}$, $R^{13}$, $R^{14}$, $R^{17}$, $R^{19}$, $R^{21}$, $R^{24}$, $R^{25}$, $R^{26}$, $R^{28}$, $R^{29}$ and $R^{30}$ independently of one another for each individual occurrence represent a radical chosen from the series consisting of hydrogen, $(C_1-C_6)$-alkyl, $(C_3-C_7)$-cycloalkyl, 4- to 7-membered heterocycloalkyl, phenyl and 5- or 6-membered heteroaryl, wherein $(C_3-C_7)$-cycloalkyl, 4- to 7-membered heterocycloalkyl, phenyl and 5- or 6-membered heteroaryl in their turn can in each case be substituted up to three times in an identical or different manner by halogen, cyano, $(C_1-C_4)$-alkyl, tri-fluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxy-carbonyl and $(C_1-C_6)$-alkyl can be substituted once to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and/or 5- or 6-membered heteroaryl, (b) $R^{12}$, $R^{15}$, $R^{16}$, $R^{18}$, $R^{20}$, $R^{22}$, $R^{23}$, $R^{27}$ and $R^{31}$ independently of one another for each individual occurrence represent a radical chosen from the series consisting of hydrogen and $(C_1-C_6)$-alkyl, wherein $(C_1-C_6)$-alkyl can be substituted once to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and/or $(C_1-C_4)$-alkoxycarbonyl, and/or (c) $R^{11}$ and $R^{12}$, $R^{14}$ and $R^{15}$, $R^{16}$ and $R^{17}$, $R^{18}$ and $R^{19}$, $R^{20}$ and $R^{21}$, $R^{21}$ and $R^{22}$, $R^{23}$ and $R^{24}$, $R^{26}$ and $R^{27}$ and $R^{30}$ and $R^{31}$ in each case paired together with the atoms to which they are bonded can form a 5- or 6-membered heterocycloalkyl ring, which can be substituted once to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl, and $R^3$ represents hydrogen, $(C_1-C_6)$-alkyl or $(C_3-C_7)$-cycloalkyl, and their salts, solvates and solvates of the salts, with the exception of the compounds 3-methyl-1-(pyridin-2-yl)-4-(1-pyridin-2-yl-3-methyl-1H-pyrazol-5-yl)-2H-3-pyrazolin-5(1H)-one, 3',5-dimethyl-2-phenyl-1'-(4-phenyl-1,3-thiazol-2-yl)-1'H, 2H-3,4'-bipyrazol-5'-ol, 3',5-dimethyl-2-phenyl-1'-(4-thiophen-2-yl-1,3-thiazol-2-yl)-1'H, 2H-3,4'-bipyrazol-5'-ol, 3',5-dimethyl-1'-(4-methyl-1,3-thiazol-2-yl)-2-phenyl-1'H, 2H-3,4'-bipyrazol-5'-ol, 2-(4-chlorophenyl)-3',5-dimethyl-1'-(4-phenyl-1,3-thiazol-2-yl)-1'H, 2H-3,4'-bipyrazol-5'-ol and 2-tert-butyl-1'-[4-(4-chlorophenyl)-1,3-thiazol-2-yl]-3',5-dimethyl-1'H, 2H-3,4'-bipyrazol-5'-ol.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures.

The stereoisomerically uniform constituents can be isolated from such mixtures of enantiomers and/or diastereomers in a known manner.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" includes compounds which themselves can be biologically active or inactive, but are converted (for example metabolically or hydrolytically) into compounds according to the invention during their dwell time in the body.

In the context of the present invention, the substituents have the following meaning, unless specified otherwise:

$(C_1-C_6)$-Alkyl and $(C_1-C_4)$-alkyl in the context of the invention represent a straight-chain or branched alkyl radical having 1 to 6 or, respectively, 1 to 4 carbon atoms. A straight-chain or branched alkyl radical having 1 to 4 carbon atoms is preferred. There may be mentioned by way of example and preferably: methyl, ethyl, n-propyl, isopropyl, n-butyl, isobutyl, sec-butyl, tert-butyl, 1-ethylpropyl, n-pentyl and n-hexyl.

$(C_1-C_6)$-Alkoxy and $(C_1-C_4)$-alkoxy in the context of the invention represent a straight-chain or branched alkoxy radical having 2 to 6 or, respectively, 1 to 4 carbon atoms. A straight-chain or branched alkoxy radical having 1 to 4 carbon atoms is preferred. There may be mentioned by way of example and preferably: methoxy, ethoxy, n-propoxy, isopropoxy, n-butoxy, tert-butoxy, n-pentoxy and n-hexoxy.

Mono-$(C_1-C_4)$-alkylamino and mono-$(C_1-C_4)$-alkylamino in the context of the invention represent an amino group with a straight-chain or branched alkyl substituent which contains 1 to 6 or, respectively, 1 to 4 carbon atoms. A straight-chain or branched monoalkylamino radical having 1 to 4 carbon atoms is preferred. There may be mentioned by way of example and preferably: methylamino, ethylamino, n-propylamino, isopropylamino, n-butylamino, tert-butylamino, n-pentylamino and n-hexylamino.

Di-$(C_1-C_4)$-alkylamino and di-$(C_1-C_4)$-alkylamino in the context of the invention represent an amino group with two identical or different straight-chain or branched alkyl substituents which each contain 1 to 6 or, respectively, 1 to 4 carbon atoms. Straight-chain or branched dialkylamino radicals having in each case 1 to 4 carbon atoms are preferred. There may be mentioned by way of example and preferably: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

$(C_1-C_6)$-Alkoxycarbonyl and $(C_1-C_4)$-alkoxycarbonyl in the context of the invention represent a straight-chain or branched alkoxy radical having 1 to 6 or, respectively, 1 to 4 carbon atoms which is linked via a carbonyl group. A straight-chain or branched alkoxycarbonyl radical having 1 to 4 carbon atoms in the alkoxy group is preferred. There may be mentioned by way of example and preferably: methoxycarbonyl, ethoxycarbonyl, n-propoxycarbonyl, isopropoxycarbonyl, n-butoxycarbonyl and tert-butoxycarbonyl.

$(C_3-C_7)$-Cycloalkyl and $(C_3-C_6)$-cycloalkyl in the context of the invention represent a monocyclic, saturated carbocyclic radical having 3 to 7 or, respectively, 3 to 6 ring carbon atoms. There may be mentioned by way of example and preferably: cyclopropyl, cyclobutyl, cyclopentyl, cyclohexyl and cycloheptyl.

4- to 10-membered heterocycloalkyl in the context of the invention represents a heterocyclic radical which is mono- or optionally bicyclic, saturated or contains a double bond and has 4 to 10 ring atoms, contains one or two ring hetero atoms from the series consisting of N, O and/or S and is linked via a ring carbon atom or optionally a ring nitrogen atom. There may be mentioned by way of example: azetidinyl, oxetanyl, thietanyl, pyrrolidinyl, pyrrolinyl, pyrazolidinyl, dihydropyrazolyl, tetrahydrofuranyl, thiolanyl, 1,3-oxazolidinyl, 1,3-thiazolidinyl, piperidinyl, tetrahydropyridyl, piperazinyl, tetrahydropyranyl, dihydropyranyl, tetrahydrothiopyranyl, 1,3-dioxanyl, 1,4-dioxanyl, morpholinyl, thiomorpholinyl, hexahydroazepinyl, hexahydro-1,4-diazepinyl, octahydroazocinyl, octahydropyrrolo[3,4-b]pyrrolyl, octahydroisoindolyl, octahydro-pyrrolo[3,4-b]pyridyl, hexahydropyrrolo[3,4-c]pyridyl, octahydropyrrolo[1,2-a]pyra-zinyl, decahydroisoquinolinyl, octahydropyrido[1,2-a]pyrazinyl, 7-azabicyclo[2.2.1]heptanyl, 3-azabicyclo[3.2.0]heptanyl, 3-azabicyclo[3.2.1]octanyl and 8-azabicyclo[3.2.1]octanyl, 8-oxa-3-azabicyclo[3.2.1]octanyl. A monocyclic, saturated 4-to 7-membered heterocycloalkyl radical having a total of 4 to 7 ring atoms, which contains one or two ring hetero atoms from the series consisting of N, O and/or S and is linked via a ring carbon atom or optionally a ring nitrogen atom is preferred in the context of the invention. There may be mentioned by way of example: azetidinyl, oxe-tanyl, thietanyl, pyrrolidinyl, pyrazolidinyl, tetrahydrofuranyl, thiolanyl, 1,3-oxazolidinyl, piperidinyl, piperazinyl, tetrahydropyranyl, tetrahydrothiopyranyl, 1,3-dioxanyl, 1,4-dioxanyl, morpholinyl, thiomorpholinyl, hexahydroazepinyl and hexahydro-1,4-diazepinyl. A 4- to 6-membered heterocycloalkyl radical having a total of 4 to 6 ring atoms, which contains one or two ring hetero atoms from the series consisting of N and/or O, such as, for example, pyrrolidinyl, tetrahydrofuranyl, piperidinyl, piperazinyl, tetrahydropyranyl and morpholinyl, is particularly preferred.

5- or 6-membered heteroaryl in the context of the invention represents an aromatic heterocyclic radical (heteroaromatic) having a total of 5 or, respectively, 6 ring atoms which contains up to four identical or different ring hetero atoms from the series consisting of N, O and/or S and is linked via a ring carbon atom or optionally via a ring nitrogen atom. There may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl. 5- or 6-membered heteroaryl radicals having up to three ring hetero atoms from the series consisting of N, O and/or S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl and pyrazinyl, are preferred.

Halogen in the context of the invention includes fluorine, chlorine, bromine and iodine. Fluorine, chlorine and bromine are preferred, and fluorine and chlorine are particularly preferred.

If radicals in the compounds according to the invention are substituted, the radicals can be mono- or polysubstituted, unless specified otherwise. In the context of the present invention, for all the radicals which occur several times, the meaning thereof is independent of one another. Substitution by one, two or three identical or different substituents is preferred. Substitution by one or two identical or different substituents is particularly preferred.

Compounds of the formula (I) which are preferred in the context of the present invention are those in which $R^1$ represents a heteroaryl group of the formula

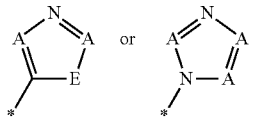

wherein
* denotes the linkage point with the dihydropyrazolone ring,

A in each individual occurrence denotes C—$R^4$ or N, wherein at most two ring members A represent N at the same time, wherein $R^4$ in each individual case, independently of one another, represents hydrogen or a substituent chosen from the series consisting of fluorine, chlorine, bromine, cyano, nitro, $(C_1-C_6)$-alkyl, hydroxyl, $(C_1-C_6)$-alkoxy, trifluoromethoxy, amino, mono-$(C_1-C_6)$-alkylamine, di-$(C_1-C_6)$-alkylamino, hydroxycarbonyl and $(C_1-C_6)$-alkoxycarbonyl, wherein the $(C_1-C_6)$-alkyl radical mentioned in its turn can be substituted up to three times in an identical or different manner by fluorine, chlorine, bromine, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and/or $(C_1-C_4)$-alkoxycarbonyl, and
E denotes O, S or N—$R^5$, wherein
$R^5$ represents hydrogen or $(C_1-C_6)$-alkyl,
$R^2$ represents a heteroaryl group of the formula

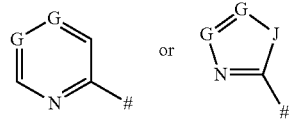

wherein
# denotes the linkage point with the dihydropyrazolone ring,

G in each case denotes C—$R^6$ or N, wherein not more than one of the two ring members G represents N, wherein $R^6$ in each individual case, independently of one another, represents hydrogen or a substituent chosen from the series consisting of fluorine, chlorine, bromine, cyano, $(C_1-C_6)$-alkyl, $(C_3-C_6)$-cycloalkyl, 4- to 6-membered heterocycloalkyl, phenyl, 5- or 6-membered heteroaryl, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$OR^{28}$ and —$NR^{30}R^{31}$, wherein (i) $(C_1-C_6)$-alkyl in its turn can be substituted once to three times in an identical or different manner by radicals chosen from the series consisting of fluorine, chlorine, bromine, cyano, $(C_3-C_6)$-cycloalkyl, 4- to 6-membered heterocycloalkyl, phenyl, 5- or 6-membered heteroaryl, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$, —$SO_2$—$R^{24}$, —$OR^{28}$ and —$NR^{30}R^{31}$, wherein the cycloalkyl, heterocycloalkyl, phenyl and heteroaryl radicals mentioned last in their turn can in each case be substituted up to twice in an identical or different manner by fluorine, chlorine, bromine, cyano, $(C_1-C_4)$-alkyl, trifluoromethyl, hydroxyl, $(C_1-C_4)$-alkoxy, trifluoro-methoxy, oxo, amino, mono-$(C_1-C_4)$-alkylamino, di-$(C_1-C_4)$-alkylamino, hydroxycarbonyl and/or $(C_1-C_4)$-alkoxy-carbonyl, (ii) $(C_3-C_6)$-cycloalkyl, 4- to 6-membered heterocloalkyl, phenyl and 5- or 6-membered heteroaryl in their turn can in each case be substituted once or twice in an identical or different manner by fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl, (iii) $R^{10}$, $R^{11}$, $R^{13}$, $R^{14}$, $R^{17}$, $R^{19}$, $R^{21}$, $R^{24}$, $R^{28}$ and $R^{30}$ independently of one another for each individual occurrence represent a radical chosen from the series consisting of hydrogen, $(C_1-C_6)$-alkyl, $(C_3-C_6)$-cycloalkyl, 4- to 6-membered hetero-cycloalkyl, phenyl and 5- or 6-membered heteroaryl, wherein $(C_3-C_6)$-cycloalkyl, 4- to 6-membered heterocycloalkyl, phenyl and 5- or 6-membered heteroaryl in their turn can in each case be substituted up to three times in an identical or different manner by fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-($C_1$-$C_4$)-alkylamino, hydroxycarbonyl and/or ($C_1$-$C_4$)-alkoxycarbonyl,
and
($C_1$-$C_6$)-alkyl can be substituted once to three times in an identical or different manner by fluorine, chlorine, bromine, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and/or 5- or 6-membered heteroaryl, (iv) $R^{12}$, $R^{15}$, $R^{16}$, $R^{18}$, $R^{20}$, $R^{22}$, $R^{23}$ and $R^{31}$ independently of one another for each individual occurrence represent a radical chosen from the series consisting of hydrogen and ($C_1$-$C_6$)-alkyl,
wherein ($C_1$-$C_6$)-alkyl can be substituted once or twice in an identical or different manner by fluorine, chlorine, bromine, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and/or ($C_1$-$C_4$)-alkoxycarbonyl,
and/or wherein (v) $R^{11}$ and $R^{12}$, $R^{14}$ and $R^{15}$, $R^{16}$ and $R^{17}$, $R^{18}$ and $R^{19}$, $R^{20}$ and $R^{21}$, $R^{21}$ and $R^{22}$, $R^{23}$ and $R^{24}$ and $R^{30}$ and $R^{31}$ in each case paired together with the atoms to which they are bonded can form a 5- or 6-membered heterocycloalkyl ring, which can be substituted once or twice in an identical or different manner by fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and/or ($C_1$-$C_4$)-alkoxycarbonyl,
and
J denotes O or S,
and
$R^3$ represents hydrogen or methyl,
and their salts, solvates and solvates of the salts.

Compounds of the formula (I) which are preferred in the context of the present invention are also those in which $R^1$ represents a heteroaryl group of the formula

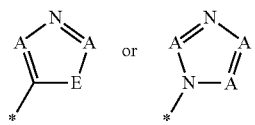

wherein
* denotes the linkage point with the dihydropyrazolone ring,
A in each individual occurrence denotes C—$R^4$ or N, wherein at most one of the ring members A represents N, wherein
$R^4$ in each individual case, independently of one another, represents hydrogen or a substituent chosen from the series consisting of fluorine, chlorine, bromine, cyano, nitro, ($C_1$-$C_6$)-alkyl, hydroxyl, ($C_1$-$C_6$)-alkoxy, trifluoromethoxy, amino, mono-($C_1$-$C_6$)-alkylamine, di-($C_1$-$C_6$)-alkylamino, hydroxycarbonyl and ($C_1$-$C_6$)-alkoxycarbonyl,
wherein the ($C_1$-$C_6$)-alkyl radical mentioned in its turn can be substituted up to three times in an identical or different manner by fluorine, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and/or ($C_1$-$C_4$)-alkoxycarbonyl,
and
E denotes O or S,
$R^2$ represents a heteroaryl group of the formula

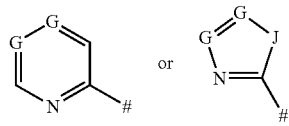

wherein
# denotes the linkage point with the dihydropyrazolone ring,
G in each case denotes C—$R^6$ or N, wherein not more than one of the two ring members G represents N, wherein
$R^6$ in each individual case, independently of one another, represents hydrogen or a substituent chosen from the series consisting of fluorine, chlorine, bromine, cyano, nitro, ($C_1$-$C_6$)-alkyl, ($C_3$-$C_6$)-cycloalkyl, 4- to 6-membered heterocycloalkyl, phenyl, 5- or 6-membered heteroaryl, —C(=O)—$OR^{10}$, —C(=O)—$NR^{11}R^{12}$, —$NR^{16}$—C(=O)—$R^{17}$, —$NR^{18}$—C(=O)—$ONR^{19}$, —$OR^{28}$ and —$NR^{30}R^{31}$, wherein (i) ($C_1$-$C_6$)-alkyl in its turn can be substituted once to three times in an identical or different manner by radicals chosen from the series consisting of fluorine, ($C_3$-$C_6$)-cycloalkyl, 4- to 6-membered heterocycloalkyl, 5- or 6-membered heteroaryl, —C(=O)—$OR^{10}$, —C(=O)—$NR^{11}R^{12}$, —$NR^{16}$—C(=O)—$R^{17}$, —$NR^{18}$—C(=O)—$OR^{19}$, —$OR^{28}$ and —$NR^{30}R^{31}$,
wherein the cycloalkyl, heterocycloalkyl and heteroaryl radicals mentioned last in their turn can in each case be substituted up to twice in an identical or different manner by fluorine, chlorine, bromine, cyano, ($C_1$-$C_4$)-alkyl, trifluoromethyl, hydroxyl, ($C_1$-$C_4$)-alkoxy, trifluoro-methoxy, oxo, amino, mono-($C_1$-$C_4$)-alkylamino, di-($C_1$-$C_4$)-alkylamino, hydroxycarbonyl and/or ($C_1$-$C_4$)-alkoxycarbonyl, (ii) ($C_3$-$C_6$)-cycloalkyl, 4- to 6-membered heterocycloalkyl, phenyl and 5- or 6-membered heteroaryl in their turn can in each case be substituted once or twice in an identical or different manner by fluorine, chlorine, bromine, cyano, ($C_1$-$C_6$)-alkyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and/or ($C_1$-$C_4$)-alkoxy-carbonyl,
wherein ($C_1$-$C_6$)-alkyl in its turn can be substituted up to three times in an identical or different manner by fluorine, hydroxyl, ($C_1$-$C_4$)-alkoxy, amino, mono-($C_1$-$C_4$)-alkyl-amino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and/or 5- or 6-membered heteroaryl, (iii) $R^{10}$, $R^{11}$, $R^{17}$, $R^{19}$, $R^{28}$ and $R^{30}$ independently of one another for each individual occurrence represent a radical chosen from the series consisting of hydrogen, ($C_1$-$C_6$)-alkyl, ($C_3$-$C_6$)-cycloalkyl and 4- to 6-membered heterocycloalkyl, wherein ($C_3$-$C_6$)-cycloalkyl and 4- to 6-membered heterocycloalkyl in their turn can in each case be substituted up to three times in an identical or different manner by fluorine, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino, hydroxycarbonyl and/or $(C_1-C_4)$-alkoxycarbonyl and $(C_1-C_6)$-alkyl can be substituted once to three times in an identical or different manner by fluorine, hydroxyl, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_6)$-cycloalkyl, 4- to 6-membered heterocycloalkyl, phenyl and/or 5- or 6-membered heteroaryl, (iv) $R^{12}$, $R^{16}$, $R^{18}$ and $R^{31}$ independently of one another for each individual occurrence represent a radical chosen from the series consisting of hydrogen and $(C_1-C_6)$-alkyl, wherein $(C_1-C_6)$-alkyl can be substituted once or twice in an identical or different manner by fluorine, hydroxyl, $(C_1-C_4)$-alkoxy, amino, mono-$(C_1-C_4)$-alkylamino, di-$(C_1-C_4)$-alkylamino, hydroxycarbonyl and/or $(C_1-C_4)$-alkoxy-carbonyl, and/or wherein (v) $R^{11}$ and $R^{12}$, $R^{16}$ and $R^{17}$, $R^{18}$ and $R^{19}$ and $R^{30}$ and $R^{31}$ in each case paired together with the atoms to which they are bonded can form a 5- or 6-membered heterocycloalkyl ring, which can be substituted once or twice in an identical or different manner by fluorine, $(C_1-C_4)$-alkyl, trifluoro-methyl, hydroxyl, $(C_1-C_4)$-alkoxy, oxo, amino, mono-$(C_1-C_4)$-alkylamino, di-$(C_1-C_4)$-alkylamino, hydroxycarbonyl and/or $(C_1-C_4)$-alkoxycarbonyl, and J denotes O or S, and $R^3$ represents hydrogen, and their salts, solvates and solvates of the salts.

Compounds of the formula (I) which are particularly preferred in the context of the present invention are those in which $R^1$ represents a heteroaryl group of the formula

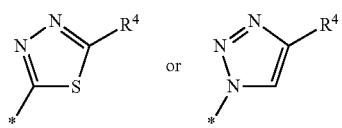

wherein

* denotes the linkage point with the dihydropyrazolone ring and $R^4$ denotes hydrogen, fluorine, chlorine, bromine, cyano, $(C_1-C_4)$-alkyl, trifluoromethyl, hydroxymethyl, $(C_1-C_4)$-alkoxy, trifluoromethoxy, hydroxycarbonyl or $(C_1-C_4)$-alkoxycarbonyl, $R^2$ represents a heteroaryl group of the formula

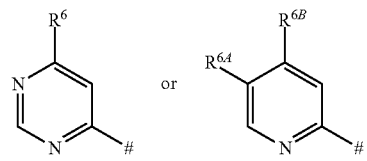

wherein # denotes the linkage point with the dihydropyrazolone ring and $R^6$, $R^{6A}$ and $R^{6B}$ are identical or different and independently of one another denote hydrogen or a substituent chosen from the series consisting of fluorine, chlorine, bromine, cyano, $(C_1-C_6)$-alkyl, trifluoromethyl, hydroxyl, $(C_1-C_6)$-alkoxy, trifluoromethoxy, amino, mono-$(C_1-C_4)$-alkylamino, di-$(C_1-C_4)$-alkylamino, hydroxycarbonyl, $(C_1-C_4)$-alkoxycarbonyl, 4- to 6-membered heterocycloalkyl, phenyl and 5- or 6-membered heteroaryl, wherein $(C_1-C_6)$-alkyl in its turn can be substituted by hydroxyl, $(C_1-C_4)$-alkoxy or amino and 4- to 6-membered heterocycloalkyl, phenyl and 5- or 6-membered heteroaryl in their turn can in each case be substituted once or twice in an identical or different manner by fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxy-carbonyl and/or $(C_1-C_4)$-alkoxycarbonyl, and $R^3$ represents hydrogen, and their salts, solvates and solvates of the salts.

Compounds of the formula (I) which are likewise particularly preferred in the context of the present invention are those in which $R^1$ represents a heteroaryl group of the formula

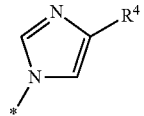

wherein

* denotes the linkage point with the dihydropyrazolone ring and $R^4$ denotes hydrogen, fluorine, chlorine, bromine, cyano, $(C_1-C_4)$-alkyl, trifluoromethyl, hydroxymethyl, $(C_1-C_4)$-alkoxy, trifluoromethoxy, hydroxycarbonyl or $(C_1-C_4)$-alkoxycarbonyl, $R^2$ represents a heteroaryl group of the formula

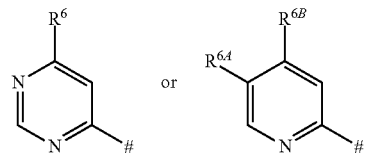

wherein
# denotes the linkage point with the dihydropyrazolone ring
and
$R^6$, $R^{6A}$ and $R^{6B}$ are identical or different and independently of one another denote hydrogen or a substituent chosen from the series consisting of fluorine, chlorine, bromine, cyano, $(C_1-C_6)$-alkyl, trifluoromethyl, hydroxyl, $(C_1-C_6)$-alkoxy, trifluoromethoxy, amino, mono-$(C_1-C_4)$-alkylamino, di-$(C_1-C_4)$-alkylamino, hydroxycarbonyl, $(C_1-C_4)$-alkoxycarbonyl and 4- to 6-membered heterocycloalkyl, wherein
$(C_1-C_6)$-alkyl in its turn can be substituted by hydroxyl, $(C_1-C_4)$-alkoxy or amino
and
4- to 6-membered heterocycloalkyl in its turn can be substituted once or twice in an identical or different manner by fluorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino, hydroxycarbonyl and/or $(C_1-C_4)$-alkoxycarbonyl,
and
$R^3$ represents hydrogen,
and their salts, solvates and solvates of the salts.

The radical definitions given in detail in the particular combinations or preferred combinations of radicals are also replaced as desired by radical definitions of other combinations, independently of the particular radical combinations given.

Combinations of two or more of the abovementioned preferred ranges are very particularly preferred.

The 1,2-dihydropyrazol-3-one derivatives of the formula (I) according to the invention can also be in the tautomeric 1H-pyrazol-5-ol form (I') (see following equation 1); the two tautomeric forms are expressly included in the present invention.

Equation 1

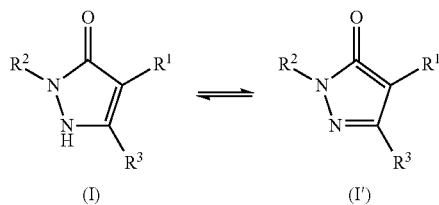

(I)   (I')

The invention also provides a process for the preparation of the compounds of the formula (I) according to the invention, characterized in that a compound of the formula (II)

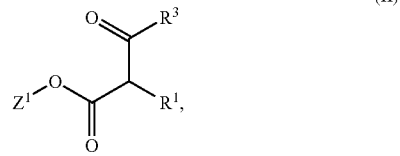

(II)

in which $R^1$ and $R^3$ have the abovementioned meanings and $Z^1$ represents methyl or ethyl,
is reacted in an inert solvent, optionally in the presence of an acid, with a compound of the formula (III)

(III)

in which $R^2$ has the abovementioned meaning,
to give compounds of the formula (IV)

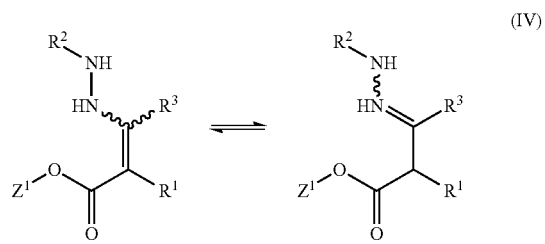

(IV)

in which $Z^1$, $R^1$, $R^2$ and $R^3$ have the abovementioned meanings,
which cyclize already under these reaction conditions or in a subsequent reaction step under the influence of a base to give the compounds of the formula (I),
and the compounds of the formula (I) are optionally converted with the corresponding (i) solvents and/or (ii) bases or acids into their solvates, salts and/or solvates of the salts.

The compounds of the formula (I) according to the invention in which $R^3$ denotes hydrogen can also be prepared by a process in which a compound of the formula (V)

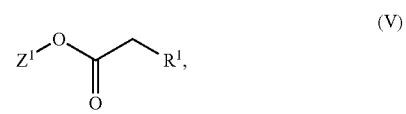

(V)

in which $Z^1$ and $R^1$ have the abovementioned meanings,
is first subjected to a condensation reaction with a compound of the formula (VI)

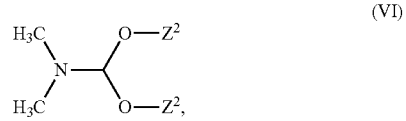

(VI)

in which
$Z^2$ represents methyl or ethyl,
to give compounds of the formula (VII)

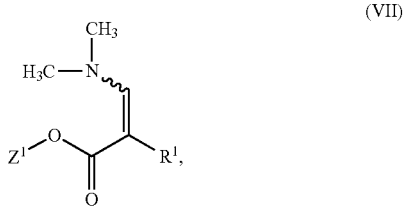

(VII)

in which $Z^1$ and $R^1$ have the abovementioned meanings,
which are then reacted in the presence of an acid with a compound of the formula (III) to give compounds of the formula (IV-A)

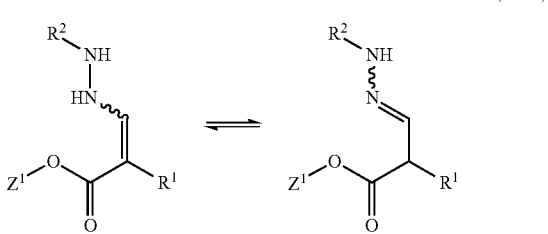

in which $Z^1$, $R^1$ and $R^2$ have the abovementioned meanings, which cyclize already under these reaction conditions or in a subsequent reaction step under the influence of a base to give the compounds of the formula (I) wherein $R^3$ represents hydrogen.

Further compounds according to the invention can optionally also be prepared by conversions of functional groups of individual substituents, in particular those listed under $R^1$ and $R^2$, starting from the compounds of the formula (I) obtained by the above processes. These conversions are carried out by conventional methods known to the person skilled in the art and include, for example, reactions such as nucleophilic or electrophilic substitution, oxidation, reduction, hydrogenation, transition metal-catalyzed coupling reactions, alkylation, acylation, amination, esterification, ester cleavage, etherification, ether cleavage, formation of carboxamides, sulfonamides, carbamates and ureas, and the introduction and removal of temporary protective groups.

Suitable inert solvents for the process steps (II)+(III)→(IV), (IV)→(I), (VII)+(III)→(IV-A) and (IV-A)→(I) are, in particular, ethers, such as diethyl ether, methyl tert-butyl ether, 1,2-dimethoxyethane, tetrahydrofuran and dioxane, or alcohols, such as methanol, ethanol, n-propanol, iso-propanol, n-butanol and tert-butanol. Methanol, ethanol tetrahydrofuran or mixtures of these solvents are preferably employed.

The process step (V)+(VI)→(VII) is preferably carried out in dimethylformamide as a solvent or also in the presence of an excess of (VI) without a further solvent. The reaction can also optionally be carried out under microwave irradiation. The reaction in general takes place in a temperature range of from +20° C. to +150° C., preferably at +80° C. to 120° C. [cf. also J. P. Bazureau et al., *Synthesis* 1998, 967; ibid. 2001 (4), 581].

Process steps (II)+(III)→(IV) and (VII)+(III)→(IV-A) can optionally advantageously be carried out with the addition of an acid. Conventional inorganic or organic acids are suitable for this, such as, for example, hydrogen chloride, acetic acid, trifluoroacetic acid, methanesulfonic acid, p-toluenesulfonic acid or camphor-10-sulfonic acid. Acetic acid or, in particular, camphor-10-sulfonic acid or p-toluenesulfonic acid are preferably used.

The reaction (II)+(III)→(IV) is in general carried out in a temperature range of from 0° C. to +100° C., preferably from +10° C. to +50° C. The reaction (VII)+(III)→(IVA) is in general carried out in a temperature range of from +20° C. to +120° C., preferably at +50° C. to +100° C.

The process sequences (II)+(III)→(IV)→(I) and (VII)+(III)→(IV-A)→(I) can be carried out under a two-stage reaction procedure or also as a one-pot reaction, without isolation of the intermediate stage (IV) or, respectively, (IV-A). For the latter variant, reaction of the components under microwave irradiation is suitable in particular; the reaction here is in general carried out in a temperature range of from +50° C. to +200° C., preferably at +100° C. to +180° C.

In some cases a cyclization to (I) also already occurs even during preparation of (IV) or, respectively, (IV-A); the cyclization can then optionally be brought to completion by in situ treatment of the reaction mixture with a base.

Conventional inorganic or organic bases are suitable as the base for such a separate cyclization step (IV)→(I) or (IV-a)→(I). These include, in particular, alkali metal hydroxides, such as, for example, sodium or potassium hydroxide, alkali metal or alkaline earth metal carbonates, such as sodium, potassium, calcium or cesium carbonate, alkali metal alcoholates, such as sodium or potassium methanolate, sodium or potassium ethanolate or sodium or potassium tert-butylate, or alkali metal hydrides, such as sodium hydride. Sodium methanolate or ethanolate are preferably used.

The base-induced reaction (IV)→(I) or (IV-A)→(I) is in general carried out in a temperature range of from 0° C. to +60° C., preferably at 0° C. to +30° C.

All the process steps can be carried out under normal, increased or reduced pressure (e.g. from 0.5 to 5 bar). In general, normal pressure is applied.

The compounds of the formula (II) can be prepared by conventional methods from the literature for C-acylation of carboxylic acid esters from compounds of the formula (V). The compounds of the formulae (III), (V) and (VI) are commercially obtainable or known from the literature or can be prepared analogously to processes described in the literature.

The preparation of the compounds according to the invention can be illustrated by the following reaction equation 2:

Equation 2

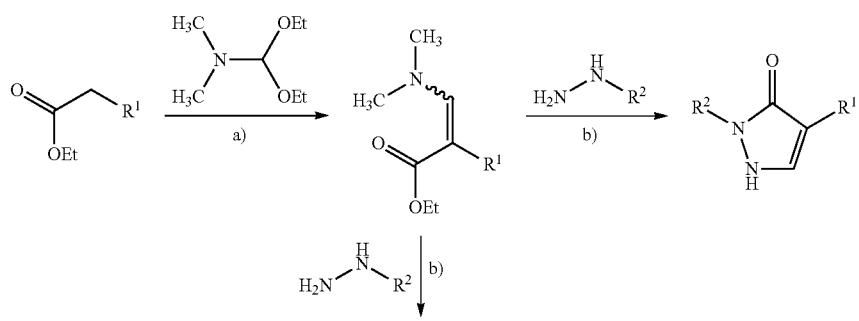

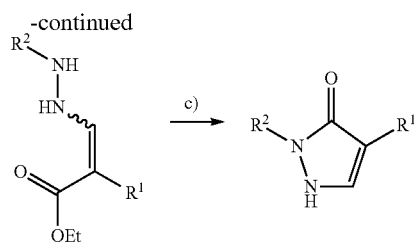

[a): DMF, 16 h, +100° C.; b): ethanol, cat. camphor-10-sulfonic acid, 78° C.; c): NaOEt, ethanol, 1 h, RT].

The compounds according to the invention show an unforeseeable, valuable pharmacological action spectrum. They are therefore suitable for use as medicaments for treatment and/or prophylaxis of diseases in humans and animals.

The compounds according to the invention are distinguished as specific inhibitors of HIF prolyl 4-hydroxylases.

On the basis of their pharmacological properties, the compounds according to the invention can be employed for treatment and/or prophylaxis of cardiovascular diseases, in particular cardiac insufficiency, coronary heart disease, angina pectoris, myocardial infarction, stroke, arteriosclerosis, essential, pulmonary and malignant hypertension and peripheral arterial occlusive disease.

The compounds according to the invention are furthermore suitable for treatment and/or prophylaxis of blood formation disorders, such as e.g. idiopathic anemias, renal anemia and anemias accompanying a tumor disease (in particular an anemia induced by chemotherapy), an infection (in particular HIV infection) or another inflammatory disease, such as e.g. rheumatoid arthritis. The compounds according to the invention are moreover suitable for supporting treatment of anemias as a result of blood loss, iron deficiency anemia, vitamin deficiency anemia (e.g. as a result of vitamin B12 deficiency or as a result of folic acid deficiency), hypoplastic and aplastic anemia or hemolytic anemia, or for supporting treatment of anemias as a result of iron utilization disorders (sideroachrestic anemia) or anemias as a result of other endocrine disorders (e.g. hypothyroidosis).

The compounds are furthermore suitable for increasing the hematocrit with the aim of obtaining blood for autodonation of blood before operations.

The compounds according to the invention can moreover be used for treatment and/or prophylaxis of operation-related states of ischaemia and consecutive symptoms thereof after surgical interventions, in particular interventions on the heart using a heart-lung machine (e.g. bypass operations, heart valve implants), interventions on the carotid arteries, interventions on the aorta and interventions with instrumental opening or penetration of the skull cap. The compounds are furthermore suitable for general treatment and/or prophylaxis in the event of surgical interventions with the aim of accelerating wound healing and shortening the reconvalescence time.

The compounds are moreover suitable for treatment and prophylaxis of consecutive symptoms of acute and protracted ischemic states of the brain (e.g. stroke, birth asphyxia).

The compounds can furthermore be employed for treatment and/or prophylaxis of cancer and for treatment and/or prophylaxis of an impairment in the state of health occurring in the course of treatment of cancer, in particular after therapy with cytostatics, antibiotics and irradiations.

The compounds are furthermore suitable for treatment and/or prophylaxis of diseases of the rheumatic type and other diseases forms to be counted as autoimmune diseases, and in particular for treatment and/or prophylaxis of an impairment in the state of health occurring in the course of medicamentous treatment of such diseases.

The compounds according to the invention can moreover be employed for treatment and/or prophylaxis of diseases of the eye (e.g. glaucoma), the brain (e.g. Parkinson's disease, Alzheimer's disease, dementia, chronic pain sensation), of chronic kidney diseases, renal insufficiency and acute renal failure and for promoting wound healing.

The compounds are moreover suitable for treatment and/or prophylaxis of general physical weakness, up to cachexia, in particular occurring to an increased extent at a more elderly age.

The compounds are furthermore suitable for treatment and/or prophylaxis of sexual dysfunction.

The compounds are moreover suitable for treatment and/or prophylaxis of diabetes mellitus and its consecutive symptoms, such as e.g. diabetic macro- and microangiopathy, diabetic nephropathy and neuropathy.

The compounds according to the invention are moreover suitable for treatment and/or prophylaxis of fibrotic diseases e.g. of the heart, the lungs and the liver.

In particular, the compounds according to the invention are also suitable for prophylaxis and treatment of retinopathy in premature babies (retinopathia prematurorum).

The present invention moreover provides the use of the compounds according to the invention for treatment and/or prevention of diseases, in particular the abovementioned diseases.

The present invention moreover provides the use of the compounds according to the invention for the preparation of a medicament for treatment and/or prevention of diseases, in particular the abovementioned diseases.

The present invention moreover provides a method for treatment and/or prevention of diseases, in particular the abovementioned diseases, using an active amount of at least one of the compounds according to the invention.

The compounds according to the invention can be employed by themselves or, if required, in combination with other active compounds. The present invention moreover provides medicaments comprising at least one of the compounds according to the invention and one or more further active compounds, in particular for treatment and/or prevention of the abovementioned diseases. Suitable active compounds in the combination which may be mentioned by way of example and preferably are: ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, digitalis (digoxin) derivatives, tumor chemotherapeutics and antibiotics.

In a preferred embodiment of the invention, the compounds according to the invention are administered in combination with an ACE inhibitor, such as, by way of example and preferably, enalapril, captopril, lisinopril, ramipril, delapril, fosinopril, quinoprol, perindopril or trandopril.

In a preferred embodiment of the invention, the compounds according to the invention are administered in combination with an angiotensin AII antagonist, such as, by way of example and preferably, losartan, candesartan, valsartan, telmisartan or embusartan.

In a preferred embodiment of the invention, the compounds according to the invention are administered in combination with a beta receptor blocker, such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a calcium antagonist, such as, by way of example and preferably, nifedipine, amlopidine, verapamil or diltiazem.

In a preferred embodiment of the invention, the compounds according to the invention are administered in combination with a phosphodiesteras (PDE) inhibitor, such as, by way of example and preferably, milrinone, amrinone, pimobendan, cilostazol, sildenafil, vardenafil or tadalafil.

In a preferred embodiment of the invention, the compounds according to the invention are administered in combination with a mineralocorticoid receptor antagonist, such as, by way of example and preferably, spironolactone, eplerenone, canrenone or potassium canrenone.

In a preferred embodiment of the invention the compounds according to the invention are administered in combination with a diuretic, such as, by way of example and preferably, furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerin, isosorbide, mannitol, amiloride or triamterene.

In a preferred embodiment of the invention, the compounds according to the invention are administered in combination with an HMG-CoA reductase inhibitor from the class of statins, such as, by way of example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a tumor chemotherapeutic, by way of example and preferably from the group consisting of platinum complexes, such as e.g. cisplatin and carboplatin, the alkylating agents, such as e.g. cyclophosphamide and chlorambucil, the antimetabolites, such as e.g. 5-fluorouracil and methotrexate, the topoisomerase inhibitors, such as e.g. etoposide and camptothecin, the antibiotics, such as e.g. doxorubicin and daunorubicin, or the kinase inhibitors, such as e.g. sorafenib and sunitinib.

In a preferred embodiment of the invention, the compounds according to the invention are administered in combination with an antibiotic, by way of example and preferably from the group consisting of penicillins, cephalosporins or quinolones, such as e.g. ciprofloxacin and moxifloxacin.

The present invention moreover provides medicaments which comprise at least one compound according to the invention, conventionally together with one or more inert, non-toxic, pharmaceutically suitable auxiliary substances, and the use thereof for the abovementioned purposes.

The compounds according to the invention can act systemically and/or locally. They can be administered in a suitable manner for this purpose, such as e.g. orally, parenterally, pulmonally, nasally, sublingually, lingually, buccally, rectally, dermally, transdermally, conjunctivally, otically or as an implant or stent.

The compounds according to the invention can be administered in suitable administration forms for these administration routes.

Administration forms which function according to the prior art, release the compounds according to the invention rapidly and/or in a modified manner and comprise the compounds according to the invention in crystalline and/or amorphized and/or dissolved form are suitable for oral administration, such as e.g. tablets (non-coated or coated tablets, for example coatings which are resistant to gastric juice or dissolve in a delayed manner or are insoluble and control the release of the compound according to the invention), tablets or films/oblates, films/lyophilisates or capsules which disintegrate rapidly in the oral cavity (for example hard or soft gelatin capsules), sugar-coated tablets, granules, pellets, powders, emulsions, suspensions, aerosols or solutions.

Parenteral administration route can be effected with bypassing of an absorption step (e.g. intravenously, intraarterially, intracardially, intraspinally or intralumbally) or with inclusion of an absorption (e.g. intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilisates or sterile powders.

For the other administration routes e.g. inhalation medicament forms (inter alia powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral and parenteral administration are preferred, in particular oral and intravenous administration.

The compounds according to the invention can be converted into the administration forms mentioned. This can be effected in a manner known per se by mixing with inert, non-toxic, pharmaceutically suitable auxiliary substances. These auxiliary substances include inter alia carrier substances (for example microcrystalline cellulose, lactose, mannitol), solvents (e.g. liquid polyethylene glycols), emulsifiers and dispersing or wetting agents (for example sodium dodecyl sulfate, polyoxysorbitan oleate), binders (for example polyvinylpyrrolidone), synthetic and natural polymers (for example albumin), stabilizers (e.g. antioxidants, such as, for example, ascorbic acid), dyestuffs (e.g. inorganic pigments, such as, for example, iron oxides) and flavor and/or smell correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behavior towards the active compound, nature of the formulation and point of time or interval at which administration takes place. Thus in some cases it may be sufficient to manage with less than the abovementioned minimum amount, while in other cases the upper limit mentioned must be exceeded. In the case where relatively large amounts are administered, it may be advisable to distribute these into several individual doses over the day.

The following embodiment examples illustrate the invention. The inventions is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

A. EXAMPLES

| Abbreviations and acronyms: | |
|---|---|
| aq. | aqueous solution |
| cat. | catalytic |
| d | day(s) |
| DCI | direct chemical ionization (in MS) |
| DMF | dimethylformamide |
| DMSO | dimethylsulfoxide |
| of th. | of theory (yield) |
| EI | electron impact ionization (in MS) |
| ESI | electrospray ionization (in MS) |
| Et | ethyl |
| GC-MS | gas chromatography-coupled mass spectroscopy |
| h | hour(s) |
| HPLC | high pressure, high performance liquid chromatography |
| conc. | concentrated |
| LC-MS | liquid chromatography-coupled mass spectroscopy |
| Meth. | method |
| min | minute(s) |
| MS | mass spectroscopy |
| NMR | nuclear magnetic resonance spectroscopy |
| $R_t$ | retention time (in HPLC) |
| RT | room temperature |
| TFA | trifluoroacetic acid |
| THF | tetrahydrofuran |

LC-MS, GC-MS and HPLC Methods:
Method 1 (LC-MS):
Instrument: Micromass Platform LCZ with HPLC Agilent Series 1100; column: Thermo Hypersil GOLD 3μ, 20 mm×4 mm; eluent A: 1 l water+0.5 ml 50% strength formic acid, eluent B: 1 l acetonitrile+0.5 ml 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 2 (LC-MS):
Apparatus type MS: Micromass ZQ; apparatus type HPLC: HP 1100 Series; UV DAD; column: Phenomenex Gemini 3μ 30 mm×3.00 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS):
Instrument: Micromass Quattro LCZ with HPLC Agilent Series 1100; column: Phenomenex Synergi 2μ Hydro-RP Mercury 20 mm×4 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 4 (LC-MS):
Apparatus type MS: Micromass ZQ; apparatus type HPLC: Waters Alliance 2795; column: Phenomenex Synergi 2μ Hydro-RP Mercury 20 mm×4 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (LC-MS):
Apparatus type MS: Micromass ZQ; apparatus type HPLC: HP 1100 Series; UV DAD; column: Phenomenex Synergi 2μ Hydro-RP Mercury 20 mm×4 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 6 (LC-MS):
Apparatus type MS: Waters ZQ; apparatus type HPLC: Agilent 1100 Series; UV DAD; column: Thermo Hypersil GOLD 3μ 20 mm×4 mm; eluent A: 1 l water+0.5 ml 50% strength formic acid, eluent B: 1 l acetonitrile+0.5 ml 50% strength formic acid; gradient: 0.0 min 100% A→3.0 min 10% A→4.0 min 10% A→4.1 min 100% A; flow rate: 2.5 ml/min; oven: 55° C.; UV detection: 210 nm.

Method 7 (LC-MS):
Apparatus type MS: Micromass ZQ; apparatus type HPLC: Waters Alliance 2795; column: Phenomenex Synergi 2.5μ MAX-RP 100A Mercury 20 mm×4 mm; eluent A: 1 l water+0.5 ml 50% strength formic acid, eluent B: 1 l acetonitrile+0.5 ml 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 8 (LC-MS):
Instrument: Micromass Quattro Micro MS with HPLC Agilent Series 1100; column: Thermo Hypersil GOLD 3μ 20 mm×4 mm; eluent A: 1 l water+0.5 ml 50% strength formic acid, eluent B: 1 l acetonitrile+0.5 ml 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 9 (LC-MS):
Instrument: Micromass Quattro LCZ with HPLC Agilent Series 1100; column: Phenomenex Synergi 2.5μ MAX-RP 100A Mercury 20 mm×4 mm; eluent A: 1 l water+0.5 ml 50% strength formic acid, eluent B: 1 l acetonitrile+0.5 ml 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 10 (LC-MS):
Instrument: Micromass QuattroPremier with Waters UPLC Acquity; column: Thermo Hypersil GOLD 1.9μ 50 mm×1 mm; eluent A: 1 l water+0.5 ml 50% strength formic acid, eluent B: 1 l acetonitrile+0.5 ml 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 11 (HPLC):
Instrument: HP 1100 Series with DAD detection; column: Kromasil 100 RP-18, 60 mm×2.1 mm, 3.5 μm; eluent A: 5 ml $HClO_4$ (70% strength)/liter water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 12 (HPLC):

Column: Kromasil 100 C18 5 μm, 250 mm×20 mm; eluent A: 0.2% strength trifluoroacetic acid, eluent B: acetonitrile; gradient: 0.0 min 95% A→10 min 5% A→15 min 5% A→15.1 min 95% A→20 min 95% A; oven: 30° C.; flow rate: 25 ml/min; UV detection: 240 nm.

Method 13 (LC-MS):

Instrument: Micromass Quattro LCZ with HPLC Agilent Series 1100; column: Phenomenex Onyx Monolithic C18, 100 mm×3 mm; eluent A: 1 l water+0.5 ml 50% strength formic acid, eluent B: 1 l acetonitrile+0.5 ml 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 14 (GC-MS):

Instrument: Micromass GCT, GC6890; column: Restek RTX-35, 15 m×200 μm×0.33 μm; constant flow rate with helium: 0.88 ml/min; oven: 70° C.; inlet: 250° C.; gradient: 70° C., 30° C./min→310° C. (hold for 3 min).

Method 15 (Preparative HPLC):

Column: Chromatorex C18 5 μm, 250 mm×20 mm; eluent A: aqueous 0.1% strength diisopropylethylamine solution, eluent B: acetonitrile; gradient: 0.0 min 60% A→4 min 60% A; oven: 30° C.; flow rate: 25 ml/min; UV detection: 260 nm.

Method 16 (Preparative LC-MS):

Instrument MS: Waters ZQ 2000; instrument HPLC: Agilent 1100, 2-column circuit; autosampler: HTC PAL; column: YMC-ODS-AQ, 50 mm×4.6 mm, 3.0 μm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Method 17 (Preparative HPLC):

Column: Kromasil 100 C18 5 μm, 250 mm×20 mm; eluent A: aqueous 0.1% strength diisopropylethylamine solution, eluent B: acetonitrile; gradient: 0.0 min 95% A→10 min 65% A→10.1 min 95% A→15 min 95% A; oven: 40° C.; flow rate: 25 ml/min; UV detection: 210 nm.

Starting Compounds and Intermediates

Example 1A

2-Hydrazino-4-methylpyridine

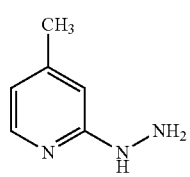

3.33 g (30.0 mmol) 2-fluoro-4-methylpyridine are initially introduced into 40 ml 2-ethoxyethanol, 14.6 ml (15.0 g, 300 mmol) hydrazine hydrate are added to the solution and the mixture is stirred at the boiling point (150° C. bath temperature) for 16 h. Thereafter, the reaction solution is concentrated on a rotary evaporator, the residue is added to 100 ml water and the mixture is extracted with ethyl acetate (three times with 100 ml each time). The combined organic phases are dried over sodium sulfate, filtered and concentrated. The residue obtained is dried in vacuo.

Yield: 1.90 g (51% of th.)

¹H-NMR (400 MHz, DMSO-d₆): δ=7.83 (d, 1H), 7.22 (s, 1H), 6.51 (s, 1H), 6.38 (d, 1H), 4.04 (s, 2H), 2.17 (s, 3H).

LC-MS (Method 1): R_t=0.80 min; MS (ESIpos): m/z=124 [M+H]⁺.

Example 2A 3-(Dimethylamino)-2-[5-(trifluoromethyl)-1,3,4-thiadiazol-2-yl]acrylic acid methyl ester

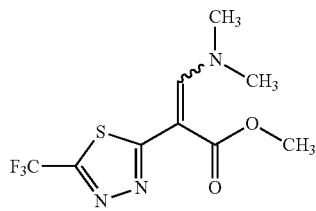 [SMILES: COC(=O)C(=CN(C)C)c1nnc(C(F)(F)F)s1]

3.05 g (13.5 mmol) 5-(trifluoromethyl)-1,3,4-thiadiazol-2-ylacetic acid ethyl ester [for preparation see DE 42 40 168-A1] are heated in 6.9 ml (40.5 mmol) dimethylformamide diethyl acetal overnight at 100° C. After cooling, the mixture is concentrated and the residue is purified by means of preparative HPLC (RP18 column; mobile phase: acetonitrile/water gradient).

Yield: 2.8 g (74% of th.)

¹H-NMR (400 MHz, DMSO-d₆): δ=8.28 (s, 1H), 3.74 (s, 3H), 3.32 (s, 6H).

LC-MS (Method 4): R_t=1.88 min; MS (ESIpos): m/z=282 [M+H]⁺.

Example 3A 3-(Dimethylamino)-2-(1H-1,2,3-triazol-1-yl)acrylic acid ethyl ester

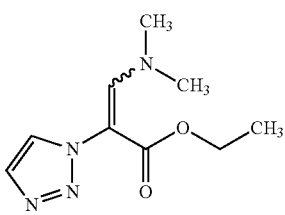

The preparation of the starting compound is carried out analogously to 2A starting from 1.00 g (6.45 mmol) 2-(1H-1,2,3-triazol-1-yl)acetic acid ethyl ester.

Yield: 1.4 g (100% of th.)

¹H-NMR (400 MHz, DMSO-d₆): δ=8.10 (d, 1H), 7.78 (d, 1H), 7.65 (s, 1H), 4.03 (q, 2H), 3.06 (br. s, 3H), 2.10 (br. s, 3H), 1.12 (t, 3H).

LC-MS (Method 5): R_t=1.40 min; MS (ESIpos): m/z=211 [M+H]⁺.

Example 4A (6-Hydrazinopyridin-3-yl)methanol

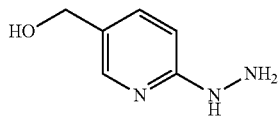

220.0 g (1.5 mol) (6-chloropyridin-3-yl)methanol [Evans et al., *Organic Letters* 2001, 19, 3009-3012] are initially introduced into 746 ml (767.1 g, 15.3 mol) hydrazine hydrate and the mixture is stirred at a bath temperature of 150° C. for 5 h. The reaction mixture is concentrated in vacuo, the residue is taken up in 500 ml water and 86.0 g (1.5 mol) potassium hydroxide are added. The mixture is stirred for 15 min, the water is then removed almost completely on a rotary evaporator and the residues of water are distilled off azeotropically with toluene several times. The oily residue is stirred in ethanol, the mixture is cooled to approx. 10° C., the potassium chloride which has precipitated out is filtered off, the filtrate is concentrated, diethyl ether is added to the residue and the mixture is stirred. Finally, the product is filtered off, the residue on the filter is washed with diethyl ether and the crystals are dried in vacuo.

Yield: 149.0 g (68% of th.)

LC-MS (Method 1): $R_t$=0.46 min; MS (ESIpos): m/z=140 [M+H]$^+$;

$^1$H-NMR (400 MHz, DMSO-d$_6$): δ=7.91 (d, 1H), 7.40 (dd, 1H), 7.29 (s, 1H), 6.66 (d, 1H), 4.94 (br. s, 1H), 4.34-4.28 (m, 2H), 4.04 (br. s, 2H).

Example 5A 1-(6-Hydrazinopyridin-3-yl)-N-methylmethanamine

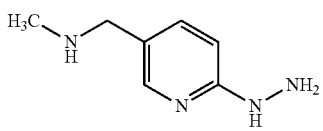

1.0 g (6.4 mmol) 1-(6-chloropyridin-3-yl)-N-methylmethanamine [for preparation see EP 0 556 684-A1] are initially introduced into 1.5 ml (1.6 g, 31.9 mmol) hydrazine hydrate and the mixture is stirred at the boiling point at a bath temperature of 150° C. for 12 h. The cooled reaction solution is concentrated and the residue is dried in vacuo. 1.1 g of the title compound, which is employed without further purification, are obtained.

LC-MS (Method 1): $R_t$=0.52 min; MS (ESIpos): m/z=153 [M+H]$^+$.

Example 6A

6-Hydrazinonicotinic acid

5.0 g (31.7 mmol) 6-chloronicotinic acid and 30.9 ml (31.8 g, 634.7 mmol) hydrazine hydrate are initially introduced into 10 ml ethanol and the mixture is stirred at the boiling point at a bath temperature of 100° C. for 16 h. The solvent and excess hydrazine hydrate are distilled off on a rotary evaporator, the residue is taken up in water, 1.8 g (31.7 mmol) potassium hydroxide are then added and the mixture is stirred for 15 min. The solvent is removed completely on a rotary evaporator, the residue is dried in vacuo and 7.5 g of crude product, which is reacted further as such, are obtained.

LC-MS (Method 1): $R_t$=0.48 min; MS (ESIpos): m/z=154 [M+H]$^+$;

$^1$H-NMR (400 MHz, DMSO-d$_6$): δ=8.49 (d, 1H), 7.89 (br. s, 1H), 7.84 (dd, 1H), 6.63 (d, 1H), 5.37 (br. s, 2H).

Example 7A

4-Chloro-6-hydrazinopyrimidine

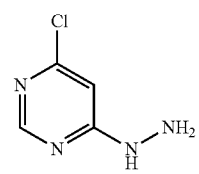

11.8 ml (12.1 g, 241.6 mmol) hydrazine hydrate are added dropwise to a solution of 20.0 g (134.3 mmol) 4,6-dichloropyrimidine in ethanol at RT, while stirring. If clouding of the solution occurs during metering in of the hydrazine hydrate, further ethanol (approx. 400 ml) is added. The reaction solution is subsequently stirred at RT for 12 h. For working up, the solid which has precipitated out is filtered off, the residue on the filter is washed twice with 150 ml water each time and twice with 100 ml diethyl ether each time and the product is dried in vacuo. A further crystalline product fraction is obtained from the concentrated mother liquor.

Yield: 16.8 g (87% of th.)

LC-MS (Method 1): $R_t$=1.17 min; MS (ESIpos): m/z=145 [M+H]$^+$;

$^1$H-NMR (400 MHz, DMSO-d$_6$): δ=8.81 (s, 1H), 8.17 (br. s, 1H), 6.75 (s, 1H), 4.48 (br. s, 2H).

Example 8A

4-Hydrazino-6-piperidin-1-ylpyrimidine

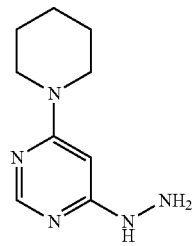 [SMILES: NNc1cc(N2CCCCC2)ncn1]

Stage a): 4-Chloro-6-piperidin-1-ylpyrimidine

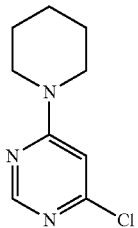 [SMILES: Clc1cc(N2CCCCC2)ncn1]

A mixture of 10.0 g (67.1 mmol) 4,6-dichloropyrimidine and 5.7 g (67.1 mmol) piperidine in 100 ml water is stirred at a bath temperature of 115° C. for 16 h. After cooling to RT, the precipitate is filtered off, washed with water and dried in vacuo.

Yield: 6.4 g (47% of th.)

LC-MS (Method 4): $R_t$=2.16 min; MS (ESIpos): m/z=198 [M+H]$^+$;

$^1$H-NMR (400 MHz, DMSO-d$_6$): δ=8.29 (s, 1H), 6.92 (s, 1H), 3.65-3.58 (m, 4H), 1.66-1.62 (m, 2H), 1.60-1.48 (m, 4H).

Stage b) 4-Hydrazino-6-piperidin-1-ylpyrimidine

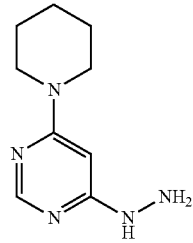 [SMILES: NNc1cc(N2CCCCC2)ncn1]

17.7 ml (18.2 g, 364.2 mmol) hydrazine hydrate are added dropwise to a solution of 6.0 g (30.4 mmol) 4-chloro-6-piperidin-1-ylpyrimidine in 50 ml ethanol at RT, while stirring. The reaction solution is subsequently stirred at 80° C. for 16 h. For working up, the mixture is concentrated in vacuo, the residue is stirred in water, the solid which has precipitated out is filtered off, the residue on the filter is washed twice with 150 ml water each time and twice with 100 ml diethyl ether each time and the product is dried in vacuo.

Yield: 4.0 g (69% of th.)

LC-MS (Method 1): $R_t$=2.06 min; MS (ESIpos): m/z=194 [M+H]$^+$;

$^1$H-NMR (400 MHz, DMSO-d$_6$): δ=7.91 (s, 1H), 7.54 (br. s, 1H), 5.89 (s, 1H), 4.11 (br. s, 2H), 3.50-3.47 (m, 4H), 1.61-1.58 (m, 2H), 1.51-1.46 (m, 4H).

Example 9A

2-Hydrazino-5-(methylsulfonyl)pyridine

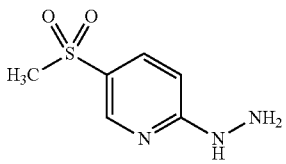

1.7 ml (1.7 g, 34.0 mmol) hydrazine hydrate are added to 2.0 g (8.5 mmol) 2,5-bis-(methylsulfonyl)pyridine [Woods et al., J. Heterocycl. Chem. 1984, 21, 97-101] in 15 ml ethanol and the mixture is stirred under reflux for 4 h. For working up, the reaction solution is cooled to 15° C., the solid which has precipitated out is filtered off, the residue on the filter is washed with ethanol and diethyl ether and the product is dried in vacuo.

Yield: 1.4 g (89% of th.)

LC-MS (Method 1): $R_t$=0.51 min; MS (ESIpos): m/z=188 [M+H]$^+$;

$^1$H-NMR (400 MHz, DMSO-d$_6$): δ=8.56 (s, 1H), 8.38 (d, 1H), 7.81 (dd, 1H), 6.79 (d, 1H), 4.42 (s, 2H), 3.11 (s, 3H).

Example 10A

5-Bromo-2-hydrazinopyridine

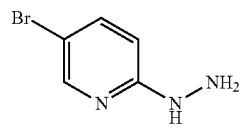

9.3 ml (9.5 g, 190.2 mmol) hydrazine hydrate are added to a solution of 1.8 g (9.5 mmol) 5-bromo-2-chloropyridine in 25 ml ethanol at RT, while stirring, and the mixture is then stirred at 90° C. for 46 h. After concentration of the reaction mixture in vacuo, the residue is stirred in water and the solid is filtered off, washed with water and diethyl ether and dried in vacuo.

Yield: 0.8 g (44% of th.)

LC-MS (Method 8): $R_t$=0.50 min; MS (ESIpos): m/z=188 [M+H]$^+$;

$^1$H-NMR (400 MHz, DMSO-d$_6$): δ=8.02 (d, 1H), 7.66 (s, 1H), 7.58 (dd, 1H), 6.69 (d, 1H), 4.16 (s, 2H).

Example 11A 1-(6-Hydrazinopyrimidin-4-yl)azetidin-3-ol

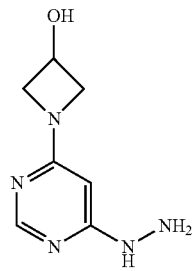 [SMILES: NNc1cc(N2CC(O)C2)ncn1]

Stage a): 1-(6-Chloropyrimidin-4-yl)azetidin-3-ol

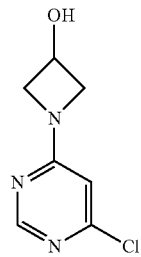

7.2 g (48.7 mmol) 2,4-dichloropyrimidine are initially introduced into 140 ml water. 5.3 g (48.7 mmol) 3-hydroxyazetidine hydrochloride and 48.7 ml 1 N sodium hydroxide solution are added and the mixture is heated at 90° C. for 72 h (the 2,4-dichloropyrimidine being detectably volatile and precipitating in crystalline form on the condenser). The solvent is removed in vacuo and the residue is dried to give 10.4 g of the crude product, which is reacted without further purification.

LC-MS (Method 10): $R_t$=0.36 min; MS (ESIpos): m/z=186 [M+H]$^+$;

$^1$H-NMR (400 MHz, DMSO-d$_6$): δ=8.29 (s, 1H), 6.50 (s, 1H), 4.63-4.57 (m, 1H), 4.26 (t, 2H), 3.82-3.75 (m, 2H).

Stage b) 1-(6-Hydrazinopyrimidin-4-yl)azetidin-3-ol

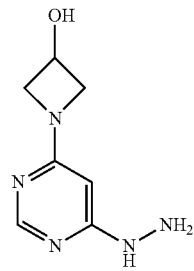 [SMILES: NNc1cc(N2CC(O)C2)ncn1]

960 mg (5.2 mmol) 1-(6-chloropyrimidin-4-yl)azetidin-3-ol and 2.5 ml (51.7 mmol) hydrazine hydrate are initially introduced into a mixture of 10 ml ethanol and 10 ml THF. The reaction is carried out at 130° C. for 1 h in a single mode microwave (CEM Explorer). The mixture is concentrated to approx. 20-50% of the original volume of liquid and is left to stand at RT for 48 h. The supernatant is decanted off from the solid formed and the solid is washed three times with 1.5 ml cold ethanol each time. It is dried under a high vacuum.

Yield: 300 mg (32% of th.)

LC-MS (Method 8): $R_t$=0.23 min; MS (ESIpos): m/z=182 [M+H]$^+$;

$^1$H-NMR (400 MHz, DMSO-d$_6$): δ=7.88 (s, 1H), 7.63 (s, 1H), 5.68 (br. s, 1H), 5.52 (s, 1H), 4.55 (br. s, 1H), 4.18-4.06 (m, 4H), 3.65-3.60 (m, 2H).

Example 12A 5-(2,2-Dimethylpropoxy)-2-hydrazinopyridine

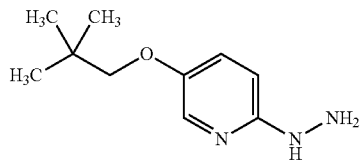

Stage a): 2-Chloro-5-(2,2-dimethylpropoxy)pyridine

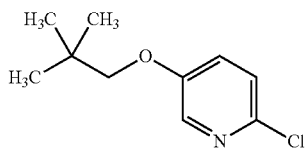

5.2 g (40.0 mmol) 6-chloropyridin-3-ol, 11.9 g (60.0 mmol) 1-iodo-2,2-dimethylpropane, 19.6 g (60.0 mmol) cesium carbonate and 120 ml diethylene glycol dimethyl ether are divided into five portions of equal size and are reacted in portions at 160° C. for 4 h in a single mode microwave (CEM Explorer). Thereafter, the five reaction mixtures obtained are combined, the solid is filtered off and rinsed with diethylene glycol dimethyl ether and the filtrate and wash solutions are combined. The majority of the solvent is removed and 300 ml water are added to the concentrated solution (approx. 50 ml). The mixture is stirred for 30 min and the solid obtained is filtered off, washed once with water and dried under a high vacuum.

Yield: 7.0 g (88% of th.)

LC-MS (Method 8): $R_t$=2.47 min; MS (ESIpos): m/z=200 [M+H]$^+$;

$^1$H-NMR (400 MHz, CDCl$_3$): δ=8.05 (d, 1H), 7.25-7.15 (m, 2H), 3.61 (s, 2H), 1.03 (s, 9H).

Stage b)

5-(2,2-Dimethylpropoxy)-2-hydrazinopyridine

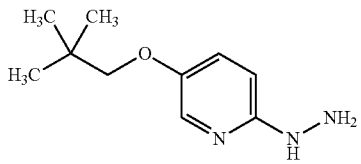

6.2 g (30.8 mmol) 2-chloro-5-(2,2-dimethylpropoxy)pyridine together with 60 ml (1.2 mol) hydrazine hydrate are divided into four portions of equal size and 10 ml ethanol are added to each portion. Each portion is reacted in a single mode microwave (CEM Explorer) at 170° C. (200 watt) for in each case 12 h. Thereafter, the four mixtures are combined and the solvent is removed. The residue is taken up in ethyl acetate and the mixture is washed in each case once with saturated sodium bicarbonate solution and saturated sodium chloride solution. The mixture is dried over magnesium sulfate and the solvent is removed in vacuo.

Yield: 6.0 g (76% of th.)

LC-MS (Method 8): $R_t$=1.28 min; MS (ESIpos): m/z=196 [M+H]$^+$;

$^1$H-NMR (400 MHz, CDCl$_3$): δ=7.84 (s, 1H), 7.17 (dd, 1H), 6.68 (d, 1H), 5.54 (br. s, 1H), 3.80 (br. s, 2H), 3.56 (s, 2H), 1.02 (s, 9H).

Example 13A

2-Chloro-5-(methoxymethyl)pyridine

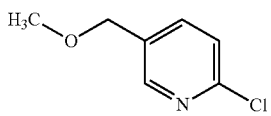

2.6 g (23.0 mmol) potassium tert-butylate are dissolved in 50 ml THF. 3.0 g (20.9 mmol) (6-chloropyridin-3-yl)methanol are added and the mixture is stirred at RT for 15 min. 4.4 g (31.3 mmol) iodomethane are then added and the mixture is stirred for approx. 30 min until the slightly exothermic reaction has subsided. The solvent is removed, the residue is taken up in methylene chloride and the mixture is washed twice with water. The mixture is dried over magnesium sulfate and concentrated and the residue is purified by column chromatography over silica gel (Biotage chromatography, mobile phase: cyclohexane/ethyl acetate 85:15).

Yield: 2.2 g (68% of th.)

LC-MS (Method 1): $R_t$=2.62 min; MS (ESIpos): m/z=158 [M+H]$^+$;

$^1$H-NMR (400 MHz, CDCl$_3$): δ=8.34 (d, 1H), 7.65 (dd, 1H), 7.32 (d, 1H), 4.45 (s, 2H), 3.41 (s, 3H).

Example 14A

2-Bromo-4,5-dimethylpyridine

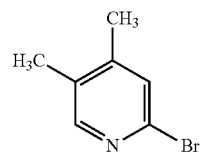

71.3 g (0.8 mol) 2-(dimethylamino)-ethanol are initially introduced into 500 ml n-hexane and the mixture is cooled to 0° C. 1.0 liter (1.6 mol) n-butyllithium solution (1.6 M in n-hexane) is slowly added and the mixture is stirred at 0° C. for 15 min. A solution of 17.9 g (166.7 mmol) 3,4-lutidine in 500 ml n-hexane is then added dropwise and the mixture is stirred at 0° C. for 1 h. It is subsequently cooled to −78° C. and a solution of 331.7 g (1.0 mol) tetrabromomethane in 1.0 liter THF is added. The reaction mixture is subsequently stirred at −78° C. for 1 h and is thereafter allowed to warm to RT. It is cooled again to 0° C. and 1.5 liters water are slowly added dropwise. The phases are separated and the organic phase is washed with water, dried over magnesium sulfate and concentrated in vacuo. The residue is first pre-purified over approx. 1 kg silica gel (mobile phase: cyclohexane/ethyl acetate 9:1, then 7:3). The product-containing fractions are combined and concentrated in vacuo. The residue is then purified again over silica gel (mobile phase: cyclohexane/ethyl acetate 9:1). The product obtained in this way contains approx. 10% of the regioisomeric 2-bromo-3,4-dimethylpyridine.

Yield: 6.7 g (20% of th.)

GC-MS (Method 14): $R_t$=4.24 min; MS (ESIpos): m/z=187 [M+H]$^+$;

$^1$H-NMR (400 MHz, CDCl$_3$): δ=8.07 (s, 1H), 7.25 (s, 1H), 2.24 (s, 3H), 2.18 (s, 3H).

Example 15A tert-Butyl [(6-chloropyridin-3-yl)methyl]carbamate

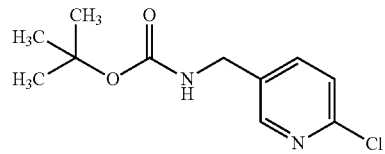 [SMILES: CC(C)(C)OC(=O)NCc1ccc(Cl)nc1]

25.0 g (175.3 mmol) 5-aminomethyl-2-chloropyrimidine are initially introduced into 175 ml methylene chloride. 175 ml 10% strength sodium hydroxide solution are added and a solution of 38.3 g (175.3 mmol) di-tert-butyl dicarbonate in 175 ml methylene chloride is added dropwise. The mixture is stirred at RT for 16 h. It is then diluted with 175 ml methylene chloride, the organic phase is separated off and the aqueous phase is extracted with 175 ml methylene chloride. The combined organic phases are dried over magnesium sulfate and concentrated in vacuo. The product is dried under a high vacuum.

Yield: 42.0 g (99% of th.)

LC-MS (Method 7): $R_t$=1.58 min; MS (ESIpos): m/z=243 [M+H]$^+$;

$^1$H-NMR (400 MHz, CDCl$_3$): δ=8.31 (d, 1H), 7.61 (dd, 1H), 7.30 (d, 1H), 4.99 (br. s, 1H), 4.30 (d, 2H), 1.46 (s, 9H).

Example 16A 4-(6-Hydrazinopyrimidin-4-yl)morpholine

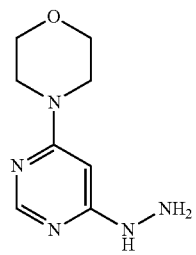 [SMILES: NNc1cc(N2CCOCC2)ncn1]

Stage a): 4-(6-Chloropyrimidin-4-yl)morpholine

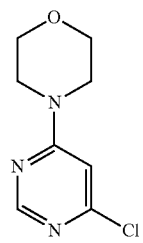

45.0 g (302.1 mmol) 4,6-dichloropyrimidine are initially introduced into 450 ml water. 26.3 g (302.1 mmol) morpholine are added and the mixture is stirred at 90° C. for 16 h. Thereafter, it is cooled to 0° C. and the precipitate formed is filtered off. The precipitate is washed once with 50 ml water and dried in air.

Yield: 51.0 g (85% of th.)
LC-MS (Method 4): R$_t$=1.09 min; MS (ESIpos): m/z=200 [M+H]$^+$;
$^1$H-NMR (400 MHz, DMSO-d$_6$): δ=8.35 (s, 1H), 6.95 (s, 1H), 3.62 (s, 8H).

Stage b) 4-(6-Hydrazinopyrimidin-4-yl)morpholine

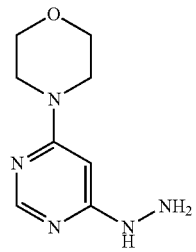 [SMILES: NNc1cc(N2CCOCC2)ncn1]

53.0 g (2.7 mmol) 4-(6-chloropyrimidin-4-yl)morpholine are initially introduced into 260 ml ethanol. 132.9 g (2.7 mol) hydrazine hydrate are added and the mixture is stirred under reflux for 16 h. Thereafter, it is cooled to RT and approx. half of the solvent is removed by distillation. The mixture is cooled to 0° C. and the solid formed is filtered off It is rinsed with cold ethanol and the solid is dried first in air and then in vacuo.

Yield: 35.0 g (68% of th.)
LC-MS (Method 1): R$_t$=0.17 min; MS (ESIpos): m/z=196 [M+H]$^+$;
$^1$H-NMR (400 MHz, DMSO-d$_6$): δ=7.94 (s, 1H), 7.70 (s, 1H), 5.91 (s, 1H), 4.15 (s, 2H), 3.66-3.60 (m, 4H), 3.45-3.37 (m, 4H).

Example 17A

2-Hydrazinopyrazine

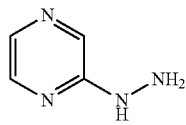

20.0 g (174.6 mmol) 2-chloropyrazine are added dropwise to 60.0 ml (61.7 g, 1.2 mol) hydrazine hydrate. The mixture is stirred at a bath temperature of 120° C. for 45 min. For working up, the cooled reaction mixture is left to stand at 2° C. for 12 h, the crystals which have precipitated out are filtered off and the residue on the filter is washed twice with petroleum ether. The residue is then recrystallized from toluene.

Yield: 6.5 g (34% of th.)
LC-MS (Method 1): R$_t$=0.49 min; MS (ESIpos): m/z=111 [M+H]$^+$;
$^1$H-NMR (400 MHz, DMSO-d$_6$): δ=8.11 (s, 1H), 7.94 (s, 1H), 7.90 (s, 1H), 7.70 (d, 1H), 4.29 (br. s, 2H).

Example 18A 5-(tert-Butoxymethyl)-2-hydrazinopyridine

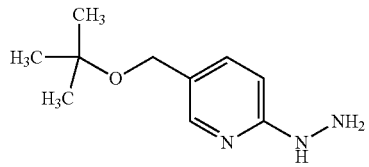

Stage a): 5-(tert-Butoxymethyl)-2-chloropyridine

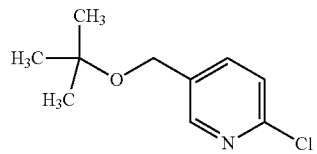

7.2 g (50.0 mmol) (6-chloropyridin-3-yl)methanol are initially introduced into 50 ml methylene chloride. 25.1 g (115.0 mmol) di-tert-butyl dicarbonate and 1.2 g (5.0 mmol) magnesium perchlorate are added and the mixture is stirred at 40° C. for 24 h. It is then cooled to RT, a further 12.5 g (87.1 mmol) di-tert-butyl dicarbonate and 600 mg (2.7 mmol) magnesium perchlorate are added and the mixture is stirred under reflux again for 2.5 h. 12.5 g (87.1 mol) di-tert-butyl dicarbonate are again added and the mixture is stirred under reflux for a further 3 h. Thereafter, it is diluted with methylene chloride and washed once with water and once with saturated sodium chloride solution. The mixture is dried over magnesium sulfate and concentrated and the residue is purified by column chromatography over silica gel (mobile phase: cyclohexane/ethyl acetate 85:15).

Yield: 7.9 g (79% of th.)

LC-MS (Method 10): $R_t$=1.12 min; MS (ESIpos): m/z=200 [M+H]$^+$;

$^1$H-NMR (400 MHz, DMSO-d$_6$): δ=8.36 (d, 1H), 7.78 (dd, 1H), 6.98 (d, 1H), 4.45 (s, 2H), 1.22 (s, 9H).

Stage b) 5-(tert-Butoxymethyl)-2-hydrazinopyridine

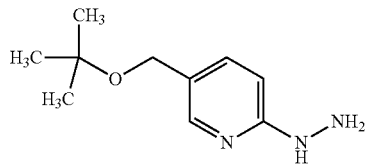

7.9 g (39.6 mmol) 5-(tert-butoxymethyl)-2-chloropyridine together with 19.8 g (395.6 mmol) hydrazine hydrate are divided into three portions of equal size and 15 ml ethanol are added to each portion. Each portion is reacted in a single mode microwave (CEM Explorer) at 170° C. for in each case 4 h. Thereafter, the three mixtures are combined and the solvent is removed. The residue is taken up in ethyl acetate and the mixture is washed once with saturated sodium bicarbonate solution. The aqueous phase is extracted once with ethyl acetate. The two ethyl acetate phases are combined and washed once with saturated sodium chloride solution. The mixture is dried over magnesium sulfate and the solvent is removed. The residue obtained is stirred in petroleum ether and the solid is filtered off.

Yield: 1.6 g (21% of th.)

LC-MS (Method 10): $R_t$=0.77 min; MS (ESIpos): m/z=196 [M+H]$^+$;

$^1$H-NMR (400 MHz, CDCl$_3$): δ=8.08 (s, 1H), 7.50 (dd, 1H), 6.68 (d, 1H), 5.77 (br. s, 1H), 4.32 (s, 2H), 3.80 (br. s, 2H), 1.28 (s, 9H).

Example 19A

6-Hydrazinopyridine-3-carbonitrile

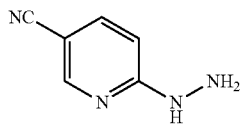

2.0 g (14.4 mmol) 6-chloronicotinic acid nitrile are stirred in 7.0 ml (7.3 g, 144.4 mmol) hydrazine hydrate at a bath temperature of 100° C. for 15 min. The reaction mixture, cooled to RT, is diluted with water and stirred at RT for 30 min. The precipitate which has separated out is filtered off, the residue on the filter is washed with water and the crystals are dried in air overnight and recrystallized from ethyl acetate.

Yield: 1.5 g (80% of th.)

LC-MS (Method 1): $R_t$=0.51 min; MS (ESIpos): m/z=135 [M+H]$^+$;

$^1$H-NMR (400 MHz, DMSO-d$_6$)=8.56 (s, 1H), 8.35 (s, 1H), 7.73 (d, 1H), 6.75 (m, 1H), 4.42 (s, 1H).

Example 20A

2-Hydrazino-5-methylpyridine

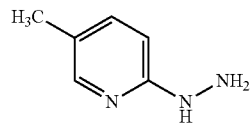

1.0 g (7.8 mmol) 2-chloro-5-methylpyridine are stirred under reflux in 5.7 ml (5.9 g, 117.6 mmol) hydrazine hydrate for 12 h. 10 ml ethylene glycol monoethyl ether are added to the cooled reaction mixture and the solvent is then removed completely on a rotary evaporator. This working step is repeated twice, methylene chloride is then added to the residue, the precipitate is filtered off, the filtrate is concentrated in vacuo and the residue is dried in vacuo.

Yield: 644 mg (67% of th.)

LC-MS (Method 8): $R_t$=0.35 min; MS (ESIpos): m/z=124 [M+H]$^+$.

Example 21A 4-Cyclopropyl-6-hydrazinopyrimidine

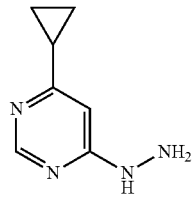 [SMILES: NNc1cc(C2CC2)ncn1]

1.6 g (6.9 mmol) 4-chloro-6-cyclopropylpyrimidine [FR 1 519 069 (1966); Chem. Abstr. 71, 49965y, 1969] and 3.4 ml (3.5 g, 69.0 mmol) hydrazine hydrate are stirred at a bath temperature of 90° C. for 16 h. Ethylene glycol monoethyl ether is added to the cooled reaction mixture and the mixture is concentrated in vacuo. This operation is repeated once. The residue is then chromatographed over silica gel 60 (mobile phase: acetonitrile/water 8:2).

Yield: 0.8 g (69% of th.)

GC-MS (Method 14): $R_t$=5.72 min; MS (ESIpos): m/z=151 [M+H]$^+$;

$^1$H-NMR (400 MHz, DMSO-d$_6$): δ=8.33 (br. s, 1H), 8.19 (s, 1H), 6.59 (s, 1H), 4.85 (br. s, 2H), 1.90-1.87 (m, 1H), 0.96-0.85 (m, 4H).

The compounds listed in the following Table 1 are prepared in an analogous manner from the stated educt in accordance with the following instructions:

Hydrazine hydrate or a 1 M solution of hydrazine in THF is used. The reaction can also be carried out in a single mode microwave (CEM Explore or Emrys Optimizer), typically in ethanol or THF at 150° C. over a period of about 15 min to 4 h. The purification is carried out as described in the preparation of Example 9A or in a similar manner, e.g. by washing the precipitated-out solid with water and recrystallization from ethyl acetate or by stirring with ethyl acetate or petroleum ether. Excess hydrazine hydrate can be removed by taking up the crude product in e.g. ethyl acetate and washing the mixture with saturated sodium bicarbonate solution.

TABLE 1

| Example no. | Structure | Educts; preparation analogously to [example]; yield (% of th.) | MS (ESI) [M + H]+; LC-MS/GC-MS (method) | 1H-NMR (400 MHz) |
|---|---|---|---|---|
| 22A | 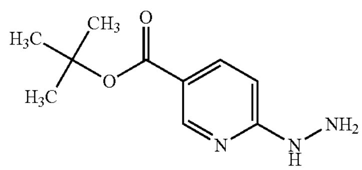 | 6-chloronicotinic acid tert-butyl ester [19A] 93% | m/z = 210; R_t = 2.28 min (1) | (DMSO-d_6): δ = 8.48 (d, 1H), 8.30 (s, 1H), 7.82 (dd, 1H), 6.70 (d, 1H), 4.35 (s, 2H), 1.50 (s, 9H). |
| 23A | 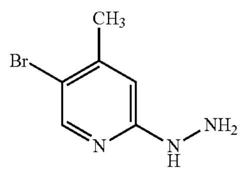 | 5-bromo-2-chloro-4-picoline [5A] 67% | m/z = 202; R_t = 0.86 min (8) | (DMSO-d_6): δ = 7.99 (s, 1H), 7.52 (s, 1H), 6.70 (s, 1H), 5.51 (br. s, 1H), 4.11 (br. s, 2H), 2.22 (s, 3H). |
| 24A | 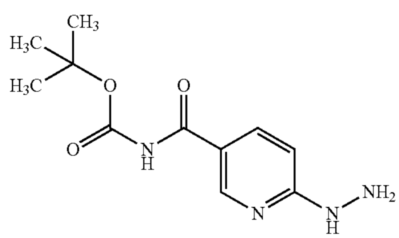 | 15A [19A] 37% | m/z = 239; R_t = 1.00 min (8) | |
| 25A | 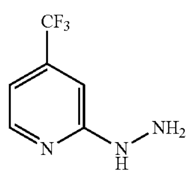 [SMILES: NNc1cc(C(F)(F)F)ccn1] | 2-chloro-4-(trifluoromethyl)pyridine [19A] 91% | m/z = 178; R_t = 0.27 min (10) | (CDCl_3): δ = 8.23 (d, 1H), 7.00 (s, 1H), 6.83 (dd, 1H), 6.30 (br. s, 1H), 3.75 (br. s, 2H). |
| 26A | 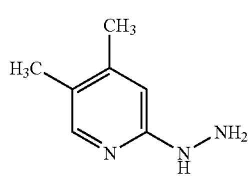 | 14A [19A] 65% | m/z = 138; R_t = 0.75 min (8) | (CDCl_3): δ = 7.86 (s, 1H), 6.51 (s, 1H), 5.61 (br. s, 1H), 3.72 (br. s, 2H), 2.20 (s, 3H), 2.12 (s, 3H). |
| 27A | 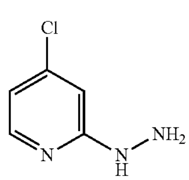 | 2,4-dichloropyridine [19A] 47% | m/z = 144; R_t = 0.23 min (8) | |

TABLE 1-continued

| Example no. | Structure | Educts; preparation analogously to [example]; yield (% of th.) | MS (ESI) [M + H]+; LC-MS/ GC-MS (method) | 1H-NMR (400 MHz) |
|---|---|---|---|---|
| 28A | 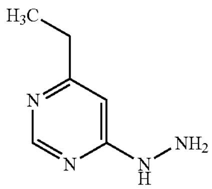 | 4-chloro-6-ethyl-pyrimidine [U.S. 5,468,751] [19A] | m/z = 139; $R_t$ = 4.94 min (14) | |
| 29A | 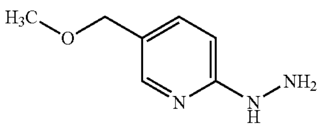 | 13A [19A] 45% | m/z = 154; $R_t$ = 0.20 min (6) | (CDCl$_3$): δ = 8.08 (d, 1H), 7.50 (dd, 1H), 6.70 (d, 1H), 5.98 (br. s, 1H), 4.33 (s, 2H), 3.72 (br. s, 2H), 3.35 (s, 3H). |

Example 30A

4-Hydrazino-6-(4-pyrrolidin-1-ylpiperidin-1-yl)pyrimidine

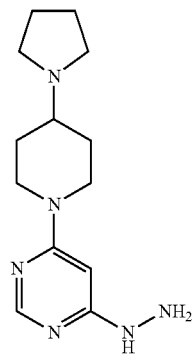 [SMILES: NNc1cc(N2CCC(N3CCCC3)CC2)ncn1]

A mixture of 2.0 g (13.8 mmol) of the compound from Example 7A and 4.3 g (27.7 mmol) 4-pyrrolidin-1-ylpyridine is stirred in 20 ml water at 100° C. for 16 h. The solid which has precipitated out is filtered off, washed first with ethanol and then with diethyl ether and dried in vacuo.

Yield: 3.0 g (82% of th.)

LC-MS (Method 8): $R_t$=0.21 min; MS (ESIpos): m/z=263 [M+H]+;

1H-NMR (400 MHz, DMSO-d$_6$): δ=7.92 (s, 1H), 7.58 (s, 1H), 5.91 (s, 1H), 4.17-4.07 (m, 4H), 2.95-2.85 (m, 2H), 2.54 (s, 2H), 2.52-2.46 (m, 2H), 2.24-2.15 (m, 1H), 1.90-1.80 (m, 2H), 1.71-1.61 (m, 4H), 1.39-1.24 (m, 2H).

Example 31A

4-Hydrazino-6-[4-(2-methoxyethyl)piperazin-1-yl]pyrimidine

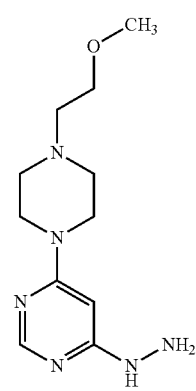 [SMILES: COCCN1CCN(c2cc(NN)ncn2)CC1]

A mixture of 1.0 g (6.9 mmol) of the compound from Example 7A and 1.1 g (7.6 mmol) 1-(2-methoxyethyl)piperazine in 10 ml water is stirred at 100° C. for 2 h. A further 0.9 g (6.2 mmol) 1-(2-methoxyethyl)piperazine is added and the reaction mixture is stirred further at 100° C. for 16 h. After concentration in vacuo, the residue is stirred in acetonitrile. The solid which has precipitated out is filtered off, washed first with ethanol and then with diethyl ether and dried in vacuo.

Yield: 0.8 g (42% of th.)

LC-MS (Method 8): $R_t$=0.22 min; MS (ESIpos): m/z=253 [M+H]+;

1H-NMR (400 MHz, DMSO-d$_6$): δ=7.93 (s, 1H), 7.64 (s, 1H), 5.91 (s, 1H), 4.14 (s, 2H), 3.50-3.40 (m, 6H), 3.24 (s, 3H), 2.47-2.39 (m, 4H).

Example 32A

[4-(Trifluoromethyl)-1H-imidazol-1-yl]acetic acid ethyl ester

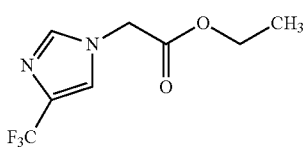

2.0 g (14.7 mmol) 4-(trifluoromethyl)-1H-imidazole are initially introduced into 5.5 ml (4.7 g, 14.7 mmol) 21% strength sodium ethylate solution in ethanol and 1.8 ml (2.7 g, 16.2 mmol) ethyl bromoacetate are added. The reaction mixture is stirred at RT for 16 h. For working up, the solid which has precipitated out is filtered off, the residue on the filter is washed with ethanol and the filtrate is concentrated in vacuo. Diisopropyl ether is added to the residue, the mixture is filtered again, the filtrate is concentrated again on a rotary evaporator and the residue is dried in vacuo. The product is obtained as a 9:1 mixture of the two regioisomers and is further reacted as such.

Yield: 3.3 g (95% of th.)

LC-MS (Method 1): $R_t$=1.75 min+1.80 min; MS (ESIpos): m/z=223 [M+H]$^+$;

$^1$H-NMR (400 MHz, DMSO-d$_6$): δ=7.93 (s, 1H), 7.82 (s, 1H), 5.04 (s, 2H), [5.07 (s, 2H)], 4.18 (q, 2H), [4.12 (q, 2H)], 1.22 (t, 3H), [1.19 (t, 3H)].

Example 33A

[4-Cyano-1H-imidazol-1-yl]acetic acid ethyl ester

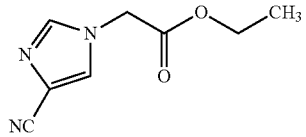

3.3 g (35.3 mmol) 1H-imidazole-4-carbonitrile [Matthews et al., *J. Org. Chem.* 1986, 51, 3228-3231] are initially introduced into 13.2 ml (11.5 g, 35.3 mmol) 21% strength sodium ethylate solution in ethanol and 4.3 ml (6.5 g, 38.9 mmol) ethyl bromoacetate are added. The reaction mixture is stirred at RT for 16 h. For working up, the solid which has precipitated out is filtered off, the residue on the filter is washed with ethanol and the filtrate is concentrated in vacuo. Diisopropyl ether is added to the residue, the mixture is filtered again, the filtrate is concentrated again on a rotary evaporator and the residue is dried in vacuo.

Yield: 3.8 g (60% of th.)

LC-MS (Method 1): $R_t$=1.17 min; MS (ESIpos): m/z=180 [M+H]$^+$;

$^1$H-NMR (400 MHz, DMSO-d$_6$): δ=8.12 (s, 1H), 7.88 (s, 1H), 5.06 (s, 2H), 4.18 (q, 2H), 1.22 (t, 3H).

Example 34A (4-Methyl-1H-imidazol-1-yl)acetic acid ethyl ester

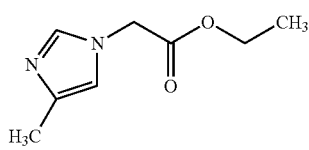

4.4 g (53.6 mmol) 4-methyl-1H-imidazole are initially introduced into 20.0 ml (17.4 g, 53.6 mmol) 21% strength sodium ethylate solution in ethanol and 6.5 ml (9.8 g, 58.9 mmol) ethyl bromoacetate are added. The reaction mixture is stirred at RT for 16 h. For working up, the solid which has precipitated out is filtered off, the residue on the filter is washed with ethanol and the filtrate is concentrated in vacuo. The residue is purified by column chromatography over silica gel (mobile phase: acetonitrile/water 9:1). The product is obtained as a 3:2 mixture of the two regioisomers and is further reacted as such.

Yield: 1.8 g (20% of th.)

LC-MS (Method 1): $R_t$=1.02 min; MS (ESIpos): m/z=169 [M+H]$^+$;

$^1$H-NMR (400 MHz, DMSO-d$_6$): δ=7.48 (s, 1H), [7.52 (s, 1H)], 6.82 (s, 1H), [6.64 (s, 1H)], 4.86 (s, 2H), [4.88 (s, 2H)], 4.22-4.11 (m, 2H), 2.07 (s, 3H), [2.06 (s, 3H)], 1.25-1.19 (m, 3H).

Example 35A

2-Methyl-1H-imidazol-1-yl)acetic acid ethyl ester

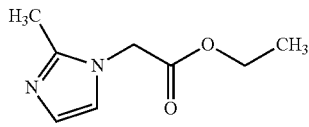

2.0 g (24.4 mmol) 2-methyl-1H-imidazole are initially introduced into 9.1 ml (7.9 g, 24.4 mmol) 21% strength sodium ethylate solution in ethanol and 2.9 ml (4.5 g, 26.8 mmol) ethyl bromoacetate are added. The reaction mixture is stirred at RT for 16 h. For working up, the solid which has precipitated out is filtered off, the residue on the filter is washed with ethanol and the filtrate is concentrated in vacuo. The residue is stirred in diisopropyl ether, the mixture is filtered again and the filtrate is concentrated in vacuo again.

Yield: 2.9 g (70% of th.)

LC-MS (Method 1): $R_t$=0.49 min; MS (ESIpos): m/z=169 [M+H]$^+$.

Example 36A (4-Methyl-1H-1,2,3-triazol-1-yl)acetic acid ethyl ester

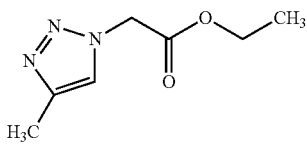

2.0 g (14.2 mmol) (4-methyl-1H-1,2,3-triazol-1-yl)acetic acid are dissolved in 30 ml ethanol and 10 drops of conc. sulfuric acid are added. The reaction mixture is stirred at RT for 16 h. For working up, the mixture is concentrated in vacuo, ethyl acetate is added to the residue and the suspension is washed with half-concentrated sodium bicarbonate solution. The organic phase is dried over magnesium sulfate, the solvent is removed completely on a rotary evaporator and the solid is dried in vacuo.

Yield: 1.5 g (61% of th.)

LC-MS (Method 1): $R_t$=2.33 min; MS (ESIpos): m/z=170 [M+H]$^+$;

$^1$H-NMR (400 MHz, DMSO-d$_6$): δ=7.82 (s, 1H), 5.31 (s, 2H), 4.17 (q, 2H), 2.25 (s, 3H), 1.21 (t, 3H).

The compounds listed in Table 2 are prepared analogously to Example 36A from the stated educt:

TABLE 2

| Example no. | Structure | Educt; yield (% of th.) | MS (ESI) [M + H]$^+$; LC-MS (method) | $^1$H-NMR (400 MHz, DMSO-d$_6$) |
|---|---|---|---|---|
| 37A | 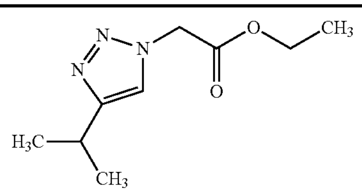 | (4-isopropyl-1H-1,2,3-triazol-1-yl)-acetic acid 100% | m/z = 198; $R_t$ = 1.68 min (4) | δ = 7.84 (s, 1H), 5.32 (s, 2H), 4.18 (q, 2H), 3.02-2.98 (m, 1H), 1.28-1.19 (m, 9H). |
| 38A | 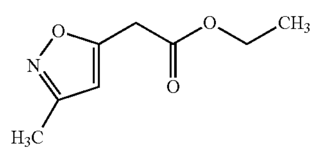 | (3-methyl-isoxazol-5-yl)-acetic acid 80% | m/z = 170; $R_t$ = 2.70 min (1) | δ = 6.28 (s, 1H), 4.12 (q, 2H), 3.95 (s, 2H), 2.21 (s, 3H), 1.21 (t, 3H). |

Example 39A 2-(1H-1,2,3-Triazol-1-yl)acetic acid ethyl ester

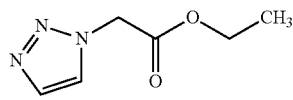

129.2 g (5.6 mol) sodium are slowly added to 4.0 liters ethanol. 400.0 g (5.6 mol) 1,2,3-1H-triazole are then added and 623 ml (938.2 g, 5.6 mol) ethyl bromoacetate are added dropwise at an internal temperature of 20-25° C. The mixture is stirred at RT for 48 h. The solid which has precipitated out is filtered off, the ethanol is removed in vacuo and the mixture is filtered again. The residue is taken up in ethyl acetate, the mixture is filtered and is concentrated in vacuo again and the residue is purified by distillation over a 30 cm column. The product is obtained at a bath temperature of 140° C., an overhead temperature of 60-115° C. and a pressure of 1 mbar.

Yield: 440.0 g (50% of th.)

HPLC (Method 11): $R_t$=1.58 min;

LC-MS (Method 1): $R_t$=0.71 min; MS (ESIpos): m/z=156 [M+H]$^+$.

Example 40A

1H-Imidazol-1-ylacetic acid ethyl ester

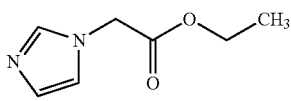

118.2 g (5.1 mol) sodium are slowly added to 2.5 liters ethanol. 350.0 g (5.1 mol) imidazole are then added and 570 ml (858.6 g, 5.1 mol) ethyl bromoacetate are added dropwise at an internal temperature of 20-25° C. The mixture is stirred at RT for 24 h. The solid which has precipitated out is filtered off, the ethanol is removed in vacuo and the mixture is filtered again. The residue is purified by column chromatography over silica gel (mobile phase: ethyl acetate).

Yield: 639.0 g (81% of th.)

GC-MS (Method 14): $R_t$=4.55 min; MS (ESIpos): m/z=155 [M+H]$^+$.

Example 41A (4-Cyano-1H-1,2,3-triazol-1-yl)acetic acid ethyl ester

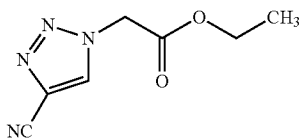

4.1 g (31.9 mmol) azidoacetic acid ethyl ester and 2.8 g (31.9 mmol) 2-chloroacrylonitrile are stirred in 32 ml water at a bath temperature of 80° C. for 16 h. After cooling to RT, the solution is rendered acid with 1 N hydrochloric acid and extracted with ethyl acetate. The organic phase is dried over sodium sulfate, filtered and concentrated in vacuo. 50 ml ethanol and 10 drops of conc. sulfuric acid are added to the residue and the mixture is stirred under reflux for 16 h. For working up, the reaction mixture is concentrated in vacuo, ethyl acetate is added to the residue, the suspension is washed with half-concentrated sodium bicarbonate solution and the organic phase is dried over sodium sulfate. The solvent is removed completely on a rotary evaporator and the solid is dried in vacuo.

Yield: 1.5 g (25% of th.)

LC-MS (Method 7): $R_t$=0.96 min; MS (ESIpos): m/z=181 [M+H]$^+$;

$^1$H-NMR (400 MHz, DMSO-$d_6$): δ=9.06 (s, 1H), 5.57 (s, 2H), 4.19 (q, 2H), 1.22 (t, 3H).

Example 42A 3-(Dimethylamino)-2-(1H-imidazol-1-yl)acrylic acid ethyl ester

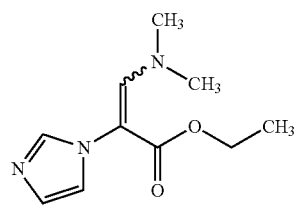

38.0 g (244.9 mmol) of the compound from Example 39A are stirred in 126 ml (108.1 g, 734.7 mmol) dimethylformamide diethyl acetal at a bath temperature of 90° C. for 16 h. After cooling, the mixture is concentrated in vacuo, the residue is stirred with diisopropyl ether and the solid is filtered off and finally washed with diisopropyl ether.

Yield: 49.0 g (95% of th.)

LC-MS (Method 4): $R_t$=2.42 min; MS (ESIpos): m/z=211 [M+H]$^+$;

$^1$H-NMR (400 MHz, DMSO-$d_6$): δ=7.52 (s, 1H), 7.49 (s, 1H), 7.05 (s, 1H), 6.91 (s, 1H), 4.02 (q, 2H), 2.63 (br. s, 6H), 1.12 (t, 3H).

Example 43A 3-(Dimethylamino)-2-(1H-1,2,4-triazol-1-yl)acrylic acid ethyl ester

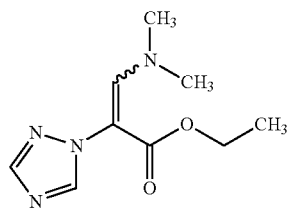

1.9 g (9.8 mmol) [1,2,4]-triazol-1-ylacetic acid ethyl ester [Ainsworth et al., *J. Am. Chem. Soc.* 1955, 77, 621-623] and 3.6 ml (2.9 g, 19.6 mmol) dimethylformamide diethyl acetal are stirred at a bath temperature of 100° C. for 12 h. For working up, the cooled reaction solution is concentrated on a rotary evaporator and the residue is dried in vacuo.

Yield: 2.3 g (90% purity, 100% of th.)

LC-MS (Method 1): $R_t$=2.32 min; MS (ESIpos): m/z=211 [M+H]$^+$;

$^1$H-NMR (400 MHz, DMSO-$d_6$): δ=8.48 (s, 1H), 8.04 (s, 1H), 7.61 (s, 1H), 4.03 (q, 2H), 3.04 (br. s, 3H), 2.25 (br. s, 3H), 1.12 (t, 3H).

Example 44A 3-(Dimethylamino)-2-[4-(trifluoromethyl)-1H-imidazol-1-yl]acrylic acid ethyl ester

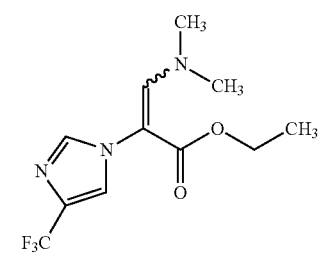 [SMILES: CCOC(=O)C(=CN(C)C)n1cnc(C(F)(F)F)c1]

38.0 g (170.8 mmol) of the compound from Example 32A and 58.5 ml (50.3 g, 341.6 mmol) dimethylformamide diethyl acetal are stirred at a bath temperature of 100° C. for 16 h. For working up, the cooled reaction solution is concentrated on a rotary evaporator and the residue is dried in vacuo.

Yield: 49.5 g (97% of th.)

LC-MS (Method 8): $R_t$=1.68 min; MS (ESIpos): m/z=278 [M+H]$^+$;

$^1$H-NMR (400 MHz, DMSO-$d_6$): δ=7.81 (s, 1H), 7.27 (s, 1H), 7.58 (s, 1H), 4.03 (q, 2H), 2.68 (br. s, 6H), 1.13 (t, 3H).

Example 45A

3-(Dimethylamino)-2-[4-cyano-1H-imidazol-1-yl] acrylic acid ethyl ester

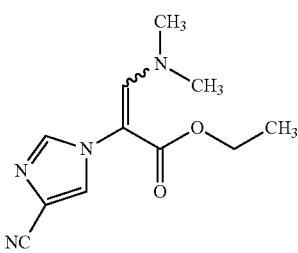

3.8 g (21.4 mmol) of the compound from Example 33A and 7.4 ml (6.3 g, 42.8 mmol) dimethylformamide diethyl acetal are stirred at a bath temperature of 100° C. for 16 h. For working up, the cooled reaction solution is concentrated on a rotary evaporator and the residue is dried in vacuo.

Yield: 5.0 g (73% purity, 73% of th.)

LC-MS (Method 1): $R_t$=2.69 min; MS (ESIpos): m/z=235 [M+H]$^+$;

$^1$H-NMR (400 MHz, DMSO-d$_6$): δ=8.13 (s, 1H), 7.85 (s, 1H), 7.58 (s, 1H), 4.03 (q, 2H), 2.69 (br. s, 6H), 1.12 (t, 3H).

Example 46A

3-(Dimethylamino)-2-[4-methyl-1H-imidazol-1-yl] acrylic acid ethyl ester

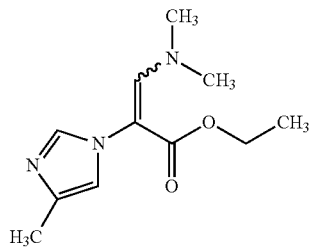 [SMILES: CCOC(=O)C(=CN(C)C)n1cnc(C)c1]

310 mg (1.5 mmol, 80% purity) of the compound from Example 34A and 0.5 ml (434 mg, 3.0 mmol) dimethylformamide diethyl acetal are stirred at a bath temperature of 100° C. for 16 h. For working up, the cooled reaction solution is concentrated on a rotary evaporator and the residue is dried in vacuo. The product is obtained as a 3:2 mixture of the two regioisomers and is further reacted as such.

Yield: 329 mg (99% of th.)

LC-MS (Method 1): $R_t$=2.05 min; MS (ESIpos): m/z=224 [M+H]$^+$;

$^1$H-NMR (400 MHz, DMSO-d$_6$): δ=7.50 (s, 1H), [7.58 (s, 1H)], 7.32 (d, 1H), [7.38 (d, 1H)], 6.73 (s, 1H), [6.66 (s, 1H)], 4.04-3.98 (m, 2H), 2.64 (br. s, 6H), 2.08 (s, 3H), [1.97 (s, 3H)], 1.12 (t, 3H).

The compounds listed in Table 3 are prepared analogously to Example 43A from the stated educt and dimethylformamide diethyl acetal:

TABLE 3

| Example no. | Structure | Educt; yield (% of th.) | LC-MS MS (ESI) [M + H]$^+$; (method) | $^1$H-NMR (400 MHz, DMSO-d$_6$) |
|---|---|---|---|---|
| 47A | (structure) | 36A | m/z = 225; $R_t$ = 2.59 min (1) | δ = 7.78 (s, 1H), 7.61 (s, 1H), 4.02 (q, 2H), 3.05 (br. s, 3H), 2.12 (br. s, 3H), 1.13 (t, 3H). |
| 48A | (structure) | 37A | m/z = 253; $R_t$ = 3.00 min (1) | δ = 7.79 (s, 1H), 7.62 (s, 1H), 4.03 (q, 2H), 3.08 (br. s, 3H), 3.00-2.97 (m, 1H), 2.09 (br. s, 3H), 1.23 (d, 6H), 1.13 (t, 3H). |

TABLE 3-continued

| Example no. | Structure | Educt; yield (% of th.) | MS (ESI) [M + H]+; LC-MS (method) | 1H-NMR (400 MHz, DMSO-d6) |
|---|---|---|---|---|
| 49A | 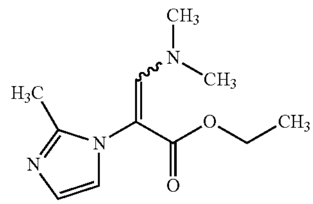 [SMILES: CCOC(=O)C(=CN(C)C)n1ccnc1C] | 35A | m/z = 224; $R_t$ = 2.03 min (1) | |
| 50A | 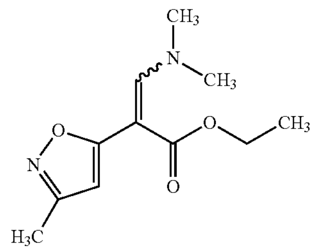 [SMILES: CCOC(=O)C(=CN(C)C)c1cc(C)no1] | 38A 75% | m/z = 225; $R_t$ = 2.91 min (1) | δ = 7.64 (s, 1H), 6.13 (s, 1H), 4.03 (q, 2H), 2.81 (br. s, 6H), 2.21 (s, 3H), 1.12 (t, 3H). |
| 51A | 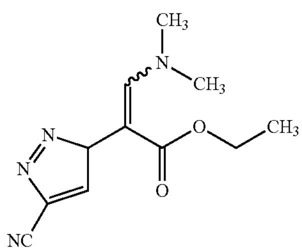 [SMILES: CCOC(=O)C(=CN(C)C)C1C=C(C#N)N=N1] | 41A | m/z = 236; $R_t$ = 1.34 min (8) | δ = 9.14 (s, 1H), 7.75 (s, 1H), 4.04 (q, 2H), 3.15 (br. s, 3H), 2.18 (br. s, 3H), 1.13 (t, 3h). |

Example 52A 2-(6-Chloropyrimidin-4-yl)-4-(1H-1,2,3-triazol-1-yl)-1,2-dihydro-3H-pyrazol-3-one hydrochloride

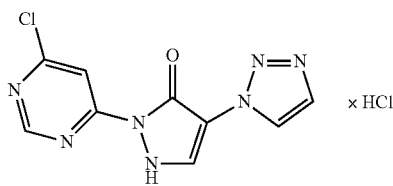 [SMILES: O=c1c(-n2ccnn2)c[nH]n1-c1cc(Cl)ncn1]

10.0 g (47.7 mmol) of the compound from Example 3A and 8.3 g (57.1 mmol) of the compound from Example 7A are initially introduced into 100 ml ethanol and 1.5 ml (2.2 g, 19.0 mmol) TFA are added. The mixture is stirred under reflux for 12 h. A 4 M solution of hydrogen chloride in dioxane is then added in excess to the cooled reaction mixture, the mixture is extracted by stirring for approx. 1 h, the crystals which have precipitated out are filtered off and the residue on the filter is washed with dioxane and ethanol. The intermediate product obtained in this way is dissolved in 150 ml ethanol, 50 ml of a 25% strength methanolic sodium methylate solution are added and the mixture is stirred at RT for 2 h. The reaction mixture is then adjusted to pH 5 with 1 N hydrochloric acid and extracted by stirring at RT for a further 2 h, the solid is filtered off, the residue on the filter is washed with ethanol and the product is dried in vacuo.

Yield: 7.0 g (49% of th.)
LC-MS (Method 10): $R_t$=1.20 min; MS (ESIpos): m/z=264 [M+H]+.

Example 53A 2-(6-Chloropyrimidin-4-yl)-4-(1H-imidazol-1-yl)-1,2-dihydro-3H-pyrazol-3-one hydrochloride

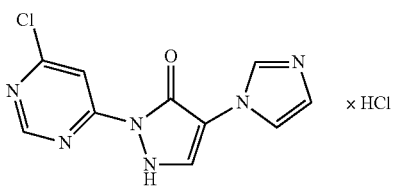

10.0 g (47.8 mmol) of the compound from Example 42A and 8.3 g (57.3 mmol) of the compound from Example 7A are initially introduced into 100 ml ethanol and 1.5 ml (2.2 g, 19.0 mmol) TFA are added. The mixture is stirred under reflux for 12 h. The crystals which have precipitated out are filtered off, the residue on the filter is rinsed with ethanol and the intermediate product is dried overnight in vacuo. This is then suspended in 20 ml methanol, 100 ml of a 4 M solution of hydrogen chloride in dioxane are added and the mixture is subsequently stirred at RT for 1 h. The solid is filtered off, the residue is washed with dioxane, ethyl acetate and diisopropyl ether and the product is dried in vacuo.

Yield: 4.6 g (32% of th.)

HPLC (Method 11): $R_t$=2.81 min; MS (ESIpos): m/z=263 [M+H]$^+$;

$^1$H-NMR (400 MHz, DMSO-d$_6$): δ=9.46 (s, 1H), 8.96 (s, 1H), 8.56 (s, 1H), 8.51 (d, 1H), 8.07-8.04 (m, 1H), 7.85-7.82 (m, 1H).

Example 54A 2-(6-Morpholin-4-ylpyrimidin-4-yl)-3-oxo-2,3-dihydro-1H-pyrazole 4-ethyl ester

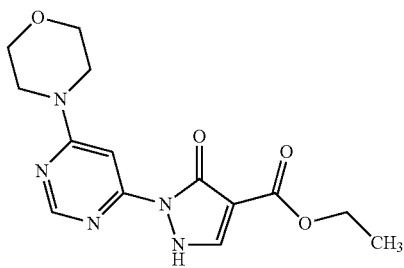 [SMILES: CCOC(=O)c1c[nH]n(-c2cc(N3CCOCC3)ncn2)c1=O]

1.4 g (10.0 mmol) potassium carbonate are dissolved in 50 ml water. 2.0 g (10.0 mmol) of the compound from Example 16A and then 2.2 g (10.0 mmol) ethoxymethylenemalonic acid diethyl ester are added to this solution and the mixture is then stirred at 100° C. for 2 h. It is allowed to cool to RT and the solid is filtered off, washed twice with water and dried under a high vacuum.

Yield: 2.4 g (75% of th.)

LC-MS (Method 8): $R_t$=1.31 min; MS (ESIpos): m/z=320 [M+H]$^+$;

$^1$H-NMR (400 MHz, DMSO-d$_6$): δ=8.30 (s, 1H), 7.97 (s, 1H), 7.48 (s, 1H), 4.00 (q, 2H), 3.75-3.61 (m, 4H), 3.55-3.45 (m, 4H), 1.18 (t, 3H).

Embodiment Examples

Example 1

2-Pyridin-2-yl-4-(1H-1,2,3-triazol-1-yl)-1,2-dihydro-3H-pyrazol-3-one

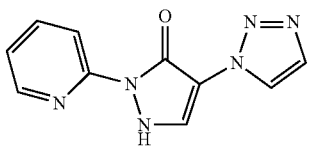 [SMILES: O=c1c(-n2ccnn2)c[nH]n1-c1ccccn1]

250 mg (1.19 mmol) of the compound from Example 3A, 108 mg (0.99 mmol) 2-hydrazinopyridine and 23 mg (99 μmol) camphor-10-sulfonic acid are dissolved in 5 ml anhydrous ethanol and the mixture is heated under reflux overnight. In each case 108 mg (0.99 mmol) 2-hydrazinopyridine are added again a total of four times and the mixture is heated further under reflux until the conversion of the compound from Example 3A is complete. After cooling, the reaction mixture is purified by preparative HPLC several times (RP18 column; mobile phase: acetonitrile/water gradient with addition of 0.1% conc. hydrochloric acid) and 6 mg (2% of th.) of the title compound are obtained.

$^1$H-NMR (400 MHz, DMSO-d$_6$): δ=8.52 (d, 1H), 8.44 (s, 1H), 8.37 (s, 1H), 8.29-8.23 (m, 1H), 8.11-8.06 (m, 1H), 7.90 (s, 1H), 7.43-7.38 (m, 1H).

LC-MS (Method 2): $R_t$=1.17 min; MS (ESIpos): m/z=229 [M+H]$^+$.

Example 2

2-(4-Methylpyridin-2-yl)-4-(1H-1,2,3-triazol-1-yl)-1,2-dihydro-3H-pyrazol-3-one

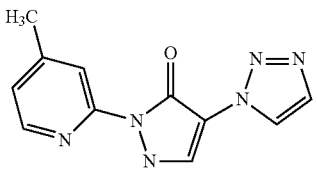

250 mg (1.19 mmol) of the compound from Example 3A, 122 mg (0.99 mmol) of the compound from Example 1A and 23 mg (99 μmol) camphor-10-sulfonic acid are dissolved in 5 ml anhydrous ethanol and the mixture is heated under reflux overnight.

Thereafter, the reaction mixture is allowed to cool and is pre-purified by means of preparative HPLC (RP18 column; mobile phase: acetonitrile/water gradient) and subsequent flash chromatography over silica gel (mobile phase: methylene chloride/methanol gradient). Renewed purification by means of preparative HPLC (RP18 column; mobile phase: acetonitrile/water gradient) finally gives 21 mg (9% of th.) of the title compound.

$^1$H-NMR (400 MHz, DMSO-d$_6$): δ=8.42 (s, 1H), 8.38 (d, 1H), 8.29 (s, 1H), 8.09 (s, 1H), 7.90 (s, 1H), 7.27 (d, 1H), 2.46 (s, 3H).

LC-MS (Method 4): $R_t$=1.05 min; MS (ESIpos): m/z=243 [M+H]$^+$.

Example 3

2-(6-Morpholin-4-yl-pyrimidin-4-yl)-4-[5-(trifluoromethyl)-1,3,4-thiadiazol-2-yl]-1,2-dihydro-3H-pyrazol-3-one

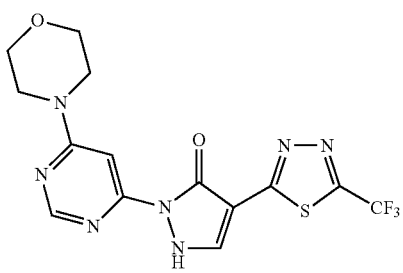 [SMILES: O=c1c(-c2nnc(C(F)(F)F)s2)c[nH]n1-c1cc(N2CCOCC2)ncn1]

2.43 g (8.62 mmol) of the compound from Example 2A, 1.53 g of the compound from Example 16A and 182 mg (784 μmol) camphor-10-sulfonic acid are dissolved in 35 ml anhydrous methanol and the mixture is heated under reflux overnight. After cooling, the mixture is concentrated, the residue is taken up again in 325 ml methanol, 0.5 ml (8.62 mmol) of a 25% strength methanolic sodium methylate solution is added and the mixture is heated again under reflux overnight. After cooling, the precipitate formed is filtered off with suction, washed with diethyl ether and suspended in a little water, an excess of 1 M hydrochloric acid is added and the suspension is concentrated again. The residue is washed with water and diethyl ether and dried. 1.34 g (43% of th.) of the title compound are obtained.

$^1$H-NMR (400 MHz, DMSO-d$_6$): δ=8.55 (s, 1H), 8.26 (s, 1H), 7.49 (s, 1H), 3.84-3.70 (m, 8H).

under reflux overnight. After cooling, the reaction mixture is purified by means of preparative HPLC (RP18 column; mobile phase: acetonitrile/water gradient) and 26 mg (8% of th.) of the title compound are obtained.

$^1$H-NMR (400 MHz, DMSO-d$_6$): δ=8.33 (s, 1H), 7.87 (s, 1H), 7.76 (s, 1H), 3.63-3.58 (m, 4H), 1.68-1.51 (m, 6H).

LC-MS (Method 3): R$_t$=2.23 min; MS (ESIpos): m/z=398 [M+H]$^+$.

The compounds listed in Table 4 are prepared analogously to Example 4 from the corresponding educts:

TABLE 4

| Example no. | Structure | Educts; yield (% of th.) | MS (ESI) [M + H]$^+$; LC-MS: R$_t$ (meth.) | $^1$H-NMR (400 MHz, DMSO-d$_6$) |
|---|---|---|---|---|
| 1 | 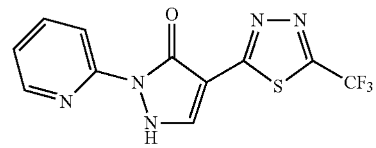 [SMILES: O=c1c(-c2nnc(C(F)(F)F)s2)c[nH]n1-c1ccccn1] | 2A; 33% | m/z = 314; 1.60 min (4) | δ = 8.38 (d, 1H), 8.27 (d, 1H), 7.86 (s, 1H), 7.83-7.77 (m, 1H), 7.10 (dd, 1H). |
| 2 | 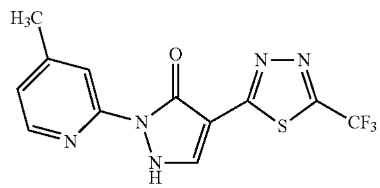 [SMILES: Cc1ccnc(-n2[nH]cc(-c3nnc(C(F)(F)F)s3)c2=O)c1] | 2A, 1A; 36% | m/z = 328; 1.71 min (4) | δ = 8.21 (d, 1H), 8.12 (s, 1H), 7.84 (s, 1H), 6.95 (d, 1H), 2.35 (s, 3H). |

LC-MS (Method 4): R$_t$=1.68 min; MS (ESIpos): m/z=400 [M+H]$^+$.

Example 4

2-(6-Piperidin-1-yl-pyrimidin-4-yl)-4-[5-(trifluoromethyl)-1,3,4-thiadiazol-2-yl]-1,2-dihydro-3H-pyrazol-3-one

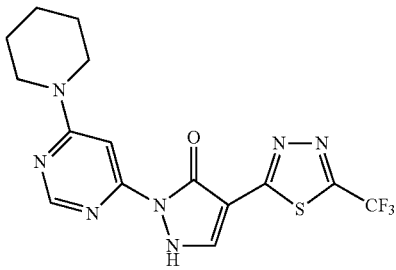

240 mg (854 μmol) of the compound from Example 2A, 150 mg (776 mmol) of the compound from Example 8A and 18 mg (78 μmol) camphor-10-sulfonic acid are dissolved in 3 ml anhydrous ethanol and the mixture is heated under reflux overnight. After cooling, 64 mg (931 μmol) sodium ethylate are added and the mixture is further stirred overnight at RT. The precipitate formed is filtered off with suction, washed with ethanol and diethyl ether and dried. The filtrate is concentrated and the residue is purified by means of preparative HPLC (RP18 column; mobile phase: acetonitrile/water gradient). The two intermediate product fractions obtained in this way are suspended together in 5 ml methanol, 15 mg (278 μmol) sodium methylate are added and the mixture is heated Example 7

2-(4-Methylpyridin-2-yl)-4-(1H-1,2,3-triazol-1-yl)-1,2-dihydro-3H-pyrazol-3-one hydrochloride

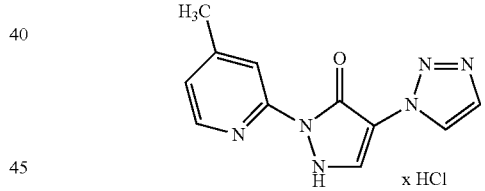

3.7 g (17.6 mmol) of the compound from Example 3A and 2.6 g (21.1 mmol) of the compound from Example 1A are dissolved in 100 ml anhydrous ethanol and 0.7 ml (1.0 g, 8.8 mmol) TFA are added. The mixture is stirred at a bath temperature of 100° C. for 16 h. Thereafter, the mixture is allowed to cool to RT and is concentrated in vacuo. The residue is dissolved in 35 ml acetonitrile and 9 ml (35.2 mmol) of a 4 N solution of hydrogen chloride in dioxane are added at RT. The precipitate is separated off and washed with 35 ml acetonitrile. The solid is washed with diisopropyl ether and then heated to 40° C. in 10 ml methanol, 10 ml ethyl acetate are added, the mixture is filtered and the product is washed with 5 ml of a 1:1 mixture of methanol and ethyl acetate as well as 2 ml ethyl acetate.

Yield: 2.0 g (40% of th.)

LC-MS (Method 2): R$_t$=1.05 min; MS (ESIpos): m/z=243 [M+H]$^+$;

$^1$H-NMR (400 MHz, DMSO-d$_6$): δ=8.42-8.40 (m, 1H), 8.37 (d, 1H), 8.29 (s, 1H), 8.09 (s, 1H), 7.89 (d, 1H), 7.27 (d, 1H), 2.46 (s, 3H).

Example 8

6-[5-Oxo-4-(1H-1,2,3-triazol-1-yl)-2,5-dihydro-1H-pyrazol-1-yl]nicotinic acid ethyl ester hydrochloride

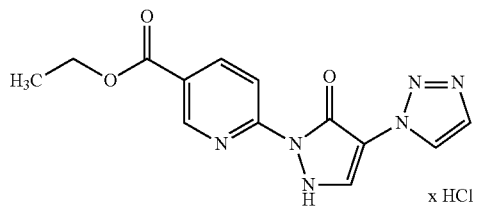 [SMILES: CCOC(=O)c1ccc(-n2[nH]cc(-n3ccnn3)c2=O)nc1]

227 mg (1.1 mmol) of the compound from Example 3A, 245 mg (1.1 mmol) 6-hydrazinonicotinic acid ethyl ester [for the preparation see WO 2006/114213] and 50 mg (0.2 mmol) camphor-10-sulfonic acid are stirred in 6 ml ethanol under reflux for 3 h. Thereafter, a further 490 mg (2.2 mmol) 6-hydrazinonicotinic acid ethyl ester and 37 mg (0.2 mmol) p-toluenesulfonic acid are added to the cooled reaction mixture and the mixture is stirred at the boiling point for 1 d. For working up, the reaction mixture is concentrated in vacuo and the residue is chromatographed by means of preparative HPLC (Method 12). 4 ml of a 4 N solution of hydrogen chloride in dioxane is added to the lyophilized trifluoroacetate salt obtained from the HPLC separation, the suspension is partly concentrated, the solid is filtered off, the residue on the filter is washed with diethyl ether and the product is dried in vacuo.

Yield: 139 mg (38% of th.)

LC-MS (Method 1): $R_t$=2.88 min; MS (ESIpos): m/z=301 $[M+H]^+$;

$^1$H-NMR (400 MHz, DMSO-$d_6$): δ=9.00 (s, 1H), 8.60-8.57 (m, 1H), 8.53-8.46 (m, 2H), 8.45 (s, 1H), 7.91 (s, 1H), 4.38 (q, 2H), 1.35 (t, 3H).

Example 9

2-(6-Piperidin-1-ylpyrimidin-4-yl)-4-(1H-1,2,3-triazol-1-yl)-1,2-dihydro-3H-pyrazol-3-one hydrochloride

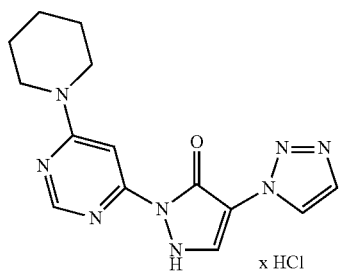 [SMILES: O=c1c(-n2ccnn2)c[nH]n1-c1cc(N2CCCCC2)ncn1]

400 mg (1.8 mmol) of the compound from Example 3A, 338 mg (1.8 mmol) of the compound from Example 8A and 60 mg (0.4 mmol) p-toluenesulfonic acid are initially introduced into a mixture of 2 ml THF and 2 ml ethanol and the mixture is reacted in a single mode microwave (Emrys Optimizer) at 140° C. for 1 h. The cooled reaction mixture is concentrated in vacuo and 2 ml of a 4 N solution of hydrogen chloride in dioxane, diethyl ether and acetonitrile are added to the residue. The precipitate which has separated out is filtered off and the residue on the filter is chromatographed by means of preparative HPLC (RP18 column; mobile phase: acetonitrile/water gradient with addition of 0.1% formic acid in the water). 4 ml of a 4 N solution of hydrogen chloride in dioxane is added to the lyophilized formate salt obtained therefrom, the suspension is partly concentrated, the solid is filtered off, the residue on the filter is washed with diethyl ether and the product is dried in vacuo.

Yield: 75 mg (12% of th.)

LC-MS (Method 1): $R_t$=2.75 min; MS (ESIpos): m/z=313 $[M+H]^+$;

$^1$H-NMR (400 MHz, DMSO-$d_6$): δ=8.51 (s, 1H), 8.38 (s, 1H), 8.21 (s, 1H), 7.85 (s, 1H), 7.38 (s, 1H), 3.76-3.72 (m, 4H), 1.74-1.63 (m, 2H), 1.59 (s, 9H).

Example 10

4-(1H-Imidazol-1-yl)-2-(6-piperidin-1-ylpyrimidin-4-yl)-1,2-dihydro-3H-pyrazol-3-one

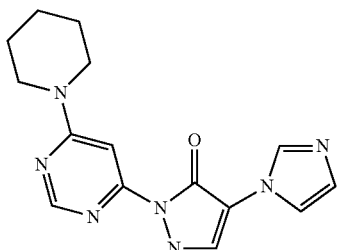

5.5 g (26.3 mmol) of the compound from Example 42A and 6.1 g (31.5 mmol) of the compound from Example 8A are dissolved in 55 ml ethyl acetate and 1.2 g (10.5 mmol) p-toluenesulfonic acid are added. The mixture is heated to the reflux and is stirred at this temperature for 16 h. After cooling to RT, the precipitate is filtered off and washed with ethyl acetate. The solid is dissolved in 50 ml water and the solution is adjusted to pH 7 with 1 N hydrochloric acid. The precipitate is filtered off, washed with water and diisopropyl ether and finally dried over phosphorus pentoxide.

Yield: 7.8 g (95% of th.)

LC-MS (Method 1): $R_t$=2.32 min; MS (ESIpos): m/z=312 $[M+H]^+$;

$^1$H-NMR (400 MHz, DMSO-$d_6$): δ=9.42 (s, 1H), 8.53 (s, 1H), 8.28 (s, 1H), 8.04 (s, 1H), 7.82 (s, 1H), 7.45 (s, 1H), 3.76-3.72 (m, 4H), 1.74-1.52 (m, 6H).

Example 11

4-(1H-Imidazol-1-yl)-2-(4-methylpyridin-2-yl)-1,2-dihydro-3H-pyrazol-3-one

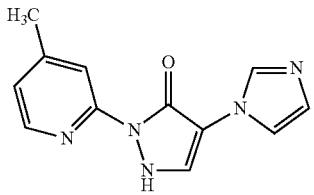 [SMILES: Cc1ccnc(-n2[nH]cc(-n3ccnc3)c2=O)c1]

200 mg (1.0 mmol) of the compound from Example 42A and 118 mg (1.0 mmol) of the compound from Example 1A are dissolved in 2 ml ethanol and 44 mg (0.2 mmol) camphor-10-sulfonic acid are added. The mixture is heated under reflux for 16 h and then concentrated and the residue is purified by means of preparative HPLC (RP18 column; mobile phase: acetonitrile/water gradient with addition of 0.1% formic acid in the water).

Yield: 4 mg (2% of th.)

LC-MS (Method 1): $R_t$=1.94 min; MS (ESIpos): m/z=242 [M+H]$^+$;

$^1$H-NMR (400 MHz, DMSO-d$_6$): δ=8.34 (d, 1H), 8.18 (s, 1H), 8.12-8.09 (m, 2H), 7.53 (s, 1H), 7.19 (d, 1H), 7.09 (s, 1H), 2.42 (s, 3H).

Example 12

2-[5-(Hydroxymethyl)pyridin-2-yl]-4-[4-(trifluoromethyl)-1H-imidazol-1-yl]-1,2-dihydro-3H-pyrazol-3-one

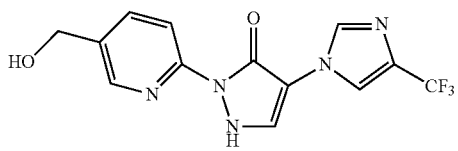 [SMILES: O=c1c(-n2cnc(C(F)(F)F)c2)c[nH]n1-c1ccc(CO)cn1]

1.0 g (3.6 mmol) of the compound from Example 44A and 502 mg (3.6 mmol) of the compound from Example 4A are dissolved in 1 ml glacial acetic acid and the mixture is stirred at RT for 16 h. Thereafter, 200 mg (1.4 mmol) of the compound from Example 4A are again added and the mixture is stirred at RT for a further 20 h. The reaction mixture is taken up in 5 ml ethyl acetate and the mixture is adjusted to pH 7 with dilute aqueous sodium bicarbonate solution. The aqueous phase is concentrated in vacuo, 1.5 ml (4.0 mmol) 21% strength ethanolic sodium ethylate solution are added to the residue and the mixture is stirred at RT for 4 h. The precipitate is filtered off and washed with ethanol.

Yield: 111 mg (9% of th.)

LC-MS (Method 4): $R_t$=1.70 min; MS (ESIpos): m/z=326 [M+H]$^+$;

$^1$H-NMR (400 MHz, DMSO-d$_6$): δ=8.44 (s, 1H), 8.39-8.21 (m, 2H), 8.19 (s, 1H), 8.14 (s, 1H), 7.98 (dd, 1H), 5.41 (t, 1H), 4.58 (d, 2H).

Example 13

2-[5-(Hydroxymethyl)pyridin-2-yl]-4-[4-(trifluoromethyl)-1H-imidazol-1-yl]-1,2-dihydro-3H-pyrazol-3-one hydrochloride

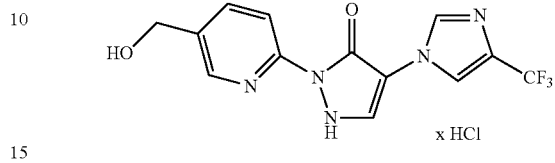

7.5 g (27.0 mmol) of the compound from Example 44A and 3.9 g (27.0 mmol) of the compound from Example 4A are dissolved in 50 ml ethanol, 1.3 g (5.4 mmol) camphor-10-sulfonic acid are added and the mixture is stirred at RT for 16 h. 1.5 g (5.4 mmol) of the compound from Example 44A and 0.8 g (5.4 mmol) of the compound from Example 4A are furthermore dissolved in 10 ml ethanol, 0.2 g (1.1 mmol) p-toluenesulfonic acid are added and the mixture is stirred at RT for 16 h. Thereafter, the two mixtures are combined, the mixture is concentrated in vacuo and the residue is purified by column chromatography over silica gel (mobile phase: acetonitrile/water 4:1). After removal of the solvent, 2 ml of a 4 N solution of hydrogen chloride in dioxane are added, the mixture is concentrated in vacuo and the residue is dried.

Yield: 1.5 g (14% of th.)

HPLC (Method 11): $R_t$=3.38 min; MS (ESIpos): m/z=326 [M+H]$^+$;

$^1$H-NMR (400 MHz, DMSO-d$_6$): δ=8.43 (s, 1H), 8.39-8.21 (m, 2H), 8.19 (s, 1H), 8.15 (s, 1H), 7.98 (dd, 1H), 5.48-5.38 (m, 1H), 4.57 (d, 2H).

Example 14

2-(4-Methylpyridin-2-yl)-4-[4-(trifluoromethyl)-1H-imidazol-1-yl]-1,2-dihydro-3H-pyrazol-3-one hydrochloride

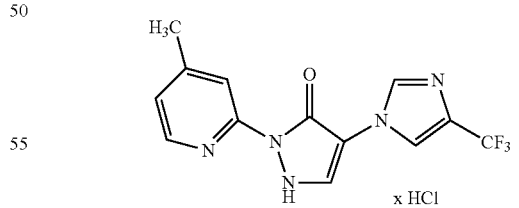

4.1 g (13.4 mmol) of the compound from Example 44A, 1.9 g (15.7 mmol) of the compound from Example 1A and 0.5 g (2.7 mmol) p-toluenesulfonic acid are reacted in a mixture of 8 ml THF and 12 ml ethanol in a single mode microwave (Emrys Optimizer) at 160° C. for 1 h. After removal of all the volatile constituents in vacuo, ethyl acetate and water are added to the residue. The organic phase separated off is washed with saturated sodium chloride solution and dried over sodium sulfate and the desiccant is filtered off. The filtrate is concentrated in vacuo and the crude product is chromatographed by means of preparative HPLC (Method 15). 5 ml of a 4 N solution of hydrogen chloride in dioxane is added to the lyophilisate obtained, the mixture is partly concentrated in vacuo, the suspension is stirred in acetonitrile and diethyl ether, the crystals are filtered off, the residue on the filter is washed with n-pentane and the product is dried in vacuo.

Yield: 0.4 g (9% of th.)

LC-MS (Method 1): $R_t$=3.11 min; MS (ESIpos): m/z=310 [M+H]$^+$;

$^1$H-NMR (400 MHz, DMSO-d$_6$): δ=8.37 (d, 1H), 8.31 (s, 1H), 8.19 (s, 1H), 8.19 (s, 1H), 8.16 (s, 1H), 8.12 (s, 1H), 7.23 (d, 1H), 2.44 (s, 3H).

Example 15

2-(6-Piperidin-1-ylpyrimidin-4-yl)-4-[4-(trifluoromethyl)-1H-imidazol-1-yl]-1,2-dihydro-3H-pyrazol-3-one hydrochloride

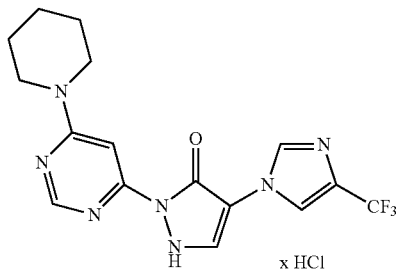 [SMILES: O=c1c(-n2cnc(C(F)(F)F)c2)c[nH]n1-c1cc(N2CCCCC2)ncn1]

200 mg (0.7 mmol) of the compound from Example 44A, 139 mg (0.7 mmol) of the compound from Example 8A and 24 mg (0.1 mmol) p-toluenesulfonic acid are reacted in 3 ml THF in a single mode microwave (Emrys Optimizer) at 160° C. for 1 h. After removal of all the volatile constituents in vacuo, the residue is chromatographed by means of preparative HPLC (RP-18 column; eluent: acetonitrile/water gradient with addition of 0.1% formic acid in the water). 2 ml of a 4 N solution of hydrogen chloride in dioxane and diethyl ether is added to the concentrated product fraction, the crystals which have precipitated out are filtered off, the residue on the filter is washed with diethyl ether and the product is dried in vacuo.

Yield: 72 mg (24% of th.)

LC-MS (Method 1): $R_t$=3.29 min; MS (ESIpos): m/z=380 [M+H]$^+$;

$^1$H-NMR (400 MHz, DMSO-d$_6$): δ=8.49 (s, 1H), 8.25 (s, 1H), 8.15 (s, 1H), 8.11 (s, 1H), 7.43 (s, 1H), 3.69 (s, 4H), 1.69-1.66 (m, 2H), 1.58 (s, 9H).

Example 16

1-[3-Oxo-2-(6-piperidin-1-ylpyrimidin-4-yl)-2,3-dihydro-1H-pyrazol-4-yl]-1H-imidazole-4-carbonitrile hydrochloride

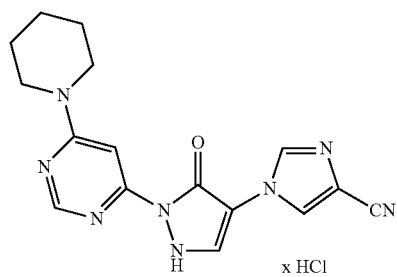 [SMILES: N#Cc1cn(-c2c[nH]n(-c3cc(N4CCCCC4)ncn3)c2=O)cn1]

200 mg (0.9 mmol) of the compound from Example 45A and 165 mg (0.9 mmol) of the compound from Example 8A are dissolved in 2 ml ethanol and 29 mg (0.2 mmol) p-toluenesulfonic acid are added. The mixture is stirred at 90° C. for 48 h. After cooling to RT, the reaction mixture is concentrated and the residue is purified by means of preparative HPLC (RP18 column; mobile phase: acetonitrile/water gradient with addition of 0.1% formic acid). An excess of a 4 N solution of hydrogen chloride in dioxane and diethyl ether is added to the concentrated product fraction, the crystals which have precipitated out are filtered off, the residue on the filter is washed with diethyl ether and the product is dried in vacuo.

Yield: 18 mg (6% of th.)

HPLC (Method 11): $R_t$=3.64 min; MS (ESIpos): m/z=337 [M+H]$^+$;

$^1$H-NMR (400 MHz, DMSO-d$_6$): δ=8.49 (s, 1H), 8.40 (s, 1H), 8.21 (s, 1H), 8.18 (s, 1H), 7.42 (s, 1H), 3.75-3.65 (m, 4H), 1.73-1.51 (m, 6H).

Example 17

2-(6-Cyclopropylpyrimidin-4-yl)-4-(1H-1,2,3-triazol-1-yl)-1,2-dihydro-3H-pyrazol-3-one hydrochloride 280 mg (1.3 mmol) of the compound from Example 3A and 200 mg (1.3 mmol) of the compound from Example 37A are dissolved in 2 ml ethanol and 21 μl (30 g, 0.3 mmol) TFA are added. The mixture is stirred under reflux for 12 h. After cooling to RT, the reaction solution is chromatographed directly by means of preparative HPLC (RP18 column; mobile phase: acetonitrile/water gradient with addition of 0.1% formic acid). The title compound (as the free base) thereby partly precipitates out in the product fractions. The precipitate is filtered off, the residue on the filter is washed with diethyl ether and an excess of a 4 N solution of hydrogen chloride in dioxane is added to the filtrate. The mixture is extracted by stirring at RT, the solid which has precipitated out is filtered off, the residue on the filter is washed with diethyl ether and the product is dried in vacuo.

Yield: 16 mg (4% of th.)
HPLC (Method 11): $R_t$=3.11 min;
$^1$H-NMR (400 MHz, DMSO-$d_6$): δ=8.90 (s, 1H), 8.59 (m, 1H), 8.44 (s, 1H), 8.29 (s, 1H), 7.91 (s, 1H), 2.26-2.24 (m, 1H), 1.17-1.05 (m, 4H).

Example 18

2-(6-Cyclopropylpyrimidin-4-yl)-4-(1H-1,2,3-triazol-1-yl)-1,2-dihydro-3H-pyrazol-3-one

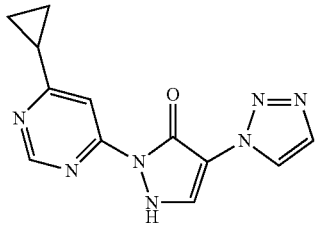 [SMILES: O=c1c(-n2ccnn2)c[nH]n1-c1cc(C2CC2)ncn1]

280 mg (1.3 mmol) of the compound from Example 3A and 200 mg (1.3 mmol) of the compound from Example 37A are dissolved in 2 ml ethanol and 21 µl (30 g, 0.3 mmol) TFA are added. The mixture is stirred under reflux for 12 h. After cooling to RT, the reaction solution is chromatographed directly by means of preparative HPLC (RP18 column; mobile phase: acetonitrile/water gradient with addition of 0.1% formic acid). The title compound thereby partly precipitates out in the product fractions. The solid is filtered off and dried in vacuo.

Yield: 5 mg (1.3% of th.)
HPLC (Method 11): $R_t$=3.10 min;
$^1$H-NMR (400 MHz, DMSO-$d_6$): δ=8.89 (s, 1H), 8.59-8.55 (m, 1H), 8.44 (s, 1H), 8.29 (s, 1H), 7.91 (s, 1H), 2.25-2.23 (m, 1H), 1.17-1.05 (m, 4H).

Example 19

2-[5-(Hydroxymethyl)pyridin-2-yl]-4-(1H-1,2,3-triazol-1-yl)-1,2-dihydro-3H-pyrazol-3-one

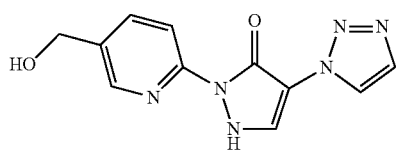 [SMILES: O=c1c(-n2ccnn2)c[nH]n1-c1ccc(CO)cn1]

15.1 g (71.9 mmol) of the compound from Example 3A and 10.0 g (71.9 mmol) of the compound from Example 4A are dissolved in 375 ml ethanol and 1.7 g (7.2 mmol) camphor-10-sulfonic acid are added. The mixture is heated under reflux for 16 h. After cooling to RT, the reaction mixture is concentrated and the residue is purified by column chromatography over silica gel (mobile phase: methylene chloride/methanol 9:1, then 1:1). The product fraction is concentrated in vacuo and the residue is stirred in diisopropyl ether, filtered off and dried in vacuo.

Yield: 1.0 g (5% of th.)
LC-MS (Method 1): $R_t$=2.14 min; MS (ESIpos): m/z=259 [M+H]$^+$;
$^1$H-NMR (400 MHz, DMSO-$d_6$): δ=8.46 (d, 1H), 8.43 (s, 1H), 8.34 (s, 1H), 8.23 (d, 1H), 8.01 (dd, 1H), 7.90 (s, 1H), 5.43 (br. s, 1H), 4.58 (s, 2H).

Example 20

1-[3-Oxo-2-(6-piperidin-1-ylpyrimidin-4-yl)-2,3-dihydro-1H-pyrazol-4-yl]-1H-1,2,3-triazole-4-carbonitrile hydrochloride

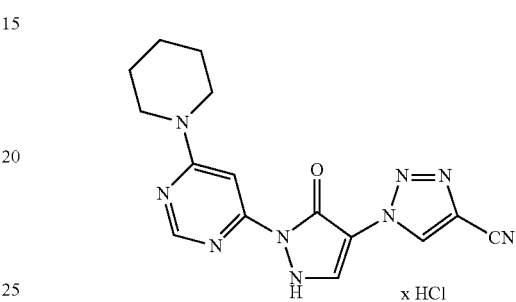

400 mg (1.7 mmol) of the compound from Example 51A and 328 mg (1.7 mmol) of the compound from Example 8A are dissolved in 4 ml ethanol and 59 mg (0.3 mmol) p-toluenesulfonic acid are added. The mixture is reacted in a single mode microwave (Emrys Optimizer) at 120° C. for 1 h. After cooling to RT, the reaction mixture is concentrated and the residue is purified by means of preparative HPLC (RP18 column; mobile phase: acetonitrile/water gradient with addition of 0.1% formic acid in the water). The formate salt thereby obtained is converted into the hydrochloride by addition of 0.2 ml of a 4 N solution of hydrogen chloride in dioxane.

Yield: 4 mg (1% of th.)
LC-MS (Method 8): $R_t$=1.73 min; MS (ESIpos): m/z=338 [M+H]$^+$;
$^1$H-NMR (400 MHz, DMSO-$d_6$): δ=9.35 (s, 1H), 8.47 (s, 1H), 8.47 (s, 1H), 8.33 (s, 1H), 7.05 (s, 1H), 3.75-3.65 (m, 4H), 1.67-1.64 (m, 2H), 1.57-1.55 (m, 4H).

Example 21

2-[6-(Dimethylamino)pyrimidin-4-yl]-4-(1H-1,2,3-triazol-1-yl)-1,2-dihydro-3H-pyrazol-3-one

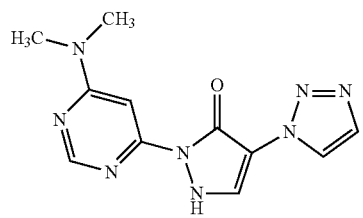 [SMILES: CN(C)c1cc(-n2[nH]cc(-n3ccnn3)c2=O)ncn1]

3.7 g (16.5 mmol) of the compound from Example 3A, 2.4 g of the compound from Example 7A and 0.6 g (3.3 mmol) p-toluenesulfonic acid are reacted in a mixture of 10 ml ethanol and 5 ml THF in a single mode microwave (Emrys Optimizer) at 140° C. for 1 h. The precipitate which thereby separates out is filtered off, the residue on the filter is washed with a mixture of ethanol and diethyl ether and the product is dried in vacuo.

Yield: 0.8 g (17% of th.)

LC-MS (Method 10): $R_t$=0.47 min; MS (ESIpos): m/z=273 $[M+H]^+$;

$^1$H-NMR (400 MHz, DMSO-$d_6$): δ=8.53 (s, 1H), 8.38 (s, 1H), 8.20 (s, 1H), 7.85 (s, 1H), 7.22 (s, 1H), 3.21 (s, 6H).

Example 22

2-(5-Bromopyridin-2-yl)-4-(1H-1,2,3-triazol-1-yl)-1,2-dihydro-3H-pyrazol-3-one hydrochloride

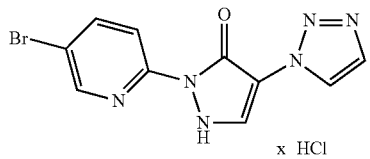 [SMILES: O=c1c(-n2ccnn2)c[nH]n1-c1ccc(Br)cn1 ; Cl]

A mixture of 280 mg (1.3 mmol) of the compound from Example 3A, 250 mg (1.3 mmol) of the compound from Example 10A and 46 mg (0.3 mmol) p-toluenesulfonic acid in 5 ml THF is reacted in a single mode microwave (Emrys Optimizer) at 170° C. for 30 min. After addition of 2 ml formic acid to the reaction solution, the solid which has precipitated out is filtered off, stirred with 3 ml of a 4 N solution of hydrogen chloride in dioxane, filtered off again, washed with diethyl ether and dried in vacuo.

Yield: 181 mg (40% of th.)

LC-MS (Method 8): $R_t$=1.50 min; MS (ESIpos): m/z=306 $[M+H]^+$;

$^1$H-NMR (400 MHz, DMSO-$d_6$): δ=8.66 (s, 1H), 8.48 (s, 1H), 8.44 (s, 1H), 8.33-8.25 (m, 2H), 7.90 (s, 1H).

Example 23

2-(5-Bromopyridin-2-yl)-4-(1H-imidazol-1-yl)-1,2-dihydro-3H-pyrazol-3-one hydrochloride

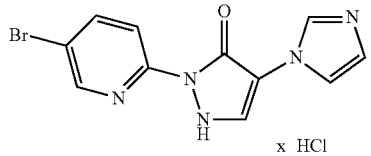

A mixture of 278 mg (1.3 mmol) of the compound from Example 42A, 250 mg (1.3 mmol) of the compound from Example 8A and 46 mg (0.3 mmol) p-toluenesulfonic acid in 5 ml THF is reacted in a single mode microwave (Emrys Optimizer) at 170° C. for 30 min. After cooling to RT, the reaction mixture is concentrated and the residue is purified by means of preparative HPLC (RP18 column; mobile phase: acetonitrile/water gradient with addition of 0.1% formic acid in the water). The formate salt thereby obtained is converted into the hydrochloride by addition of 2 ml of a 4 N solution of hydrogen chloride in dioxane. The product is washed with diethyl ether and dried in vacuo.

Yield: 60 mg (13% of th.)

LC-MS (Method 8): $R_t$=1.04 min; MS (ESIpos): m/z=307 $[M+H]^+$;

$^1$H-NMR (400 MHz, DMSO-$d_6$): δ=9.49 (s, 1H), 8.67 (s, 1H), 8.60 (s, 1H), 8.39-8.25 (m, 2H), 8.06 (s, 1H), 7.85 (s, 1H).

Example 24

2-(6-Chloropyrimidin-4-yl)-4-(1H-1,2,3-triazol-1-yl)-1,2-dihydro-3H-pyrazol-3-one hydrochloride

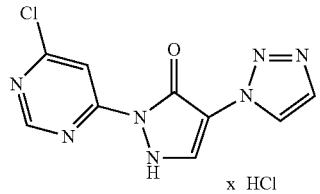 [SMILES: O=c1c(-n2ccnn2)c[nH]n1-c1cc(Cl)ncn1 ; Cl]

1.1 ml (1.6 g, 13.8 mmol) TFA are added to a mixture of 7.3 g (34.6 mmol) of the compound from Example 3A and 6.0 g (41.5 mmol) of the compound from Example 7A in 70 ml ethanol and the mixture is stirred at 100° C. for 20 h. The solid which has precipitated out is filtered off and the filtrate is concentrated in vacuo. The residue is suspended in 100 ml ethanol, 30 ml of a 30% strength sodium methanolate solution in methanol are added and the mixture is stirred at RT for 1.5 h. After addition of 42 ml of a 4 N solution of hydrogen chloride in dioxane (pH=5-6) and after stirring for 30 min, the solid is filtered off, washed first with ethanol and then with diethyl ether and dried in vacuo. Further purification is carried out by stirring in ethanol and acetonitrile several times. 10 ml of a 4 N solution of hydrogen chloride in dioxane are then added and the mixture is stirred at RT for 16 h. The product is filtered off, washed first with acetonitrile and then with diethyl ether and dried in vacuo.

Yield: 7.9 g (76% of th.)

LC-MS (Method 8): $R_t$=1.20 min; MS (ESIpos): m/z=264 $[M+H]^+$;

$^1$H-NMR (400 MHz, DMSO-$d_6$): δ=8.97 (s, 1H), 8.59 (s, 1H), 8.47 (s, 1H), 8.43 (s, 1H), 7.89 (s, 1H).

Example 25

2-[6-(4-Pyrrolidin-1-ylpiperidin-1-yl)pyrimidin-4-yl]-4-[4-(trifluoromethyl)-1H-imidazol-1-yl]-1,2-dihydro-3H-pyrazol-3-one hydrochloride

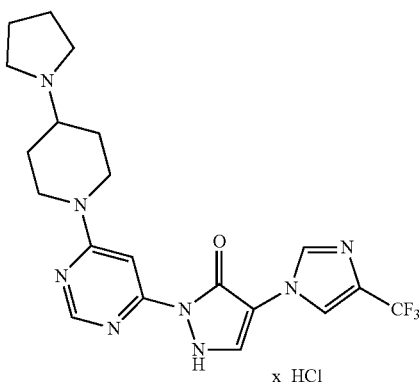 [SMILES: O=c1c(-n2cnc(C(F)(F)F)c2)c[nH]n1-c1cc(N2CCC(N3CCCC3)CC2)ncn1 ; Cl]

x HCl

76 µl (112 mg, 1.0 mmol) TFA are added to a mixture of 683 mg (2.5 mmol) of the compound from Example 44A and 711 mg (2.7 mmol) of the compound from Example 30A in 10 ml ethanol and the mixture is stirred at 100° C. for 16 h. After addition of 10 ml formic acid, the reaction solution is purified by means of preparative HPLC (RP18 column; mobile phase: acetonitrile/water gradient with addition of 0.1% formic acid in the water). The formate salt obtained is converted into the hydrochloride by addition of 2 ml of a 4 N solution of hydrogen chloride in dioxane. This is washed with diethyl ether and dried in vacuo.

Yield: 315 mg (25% of th.)

LC-MS (Method 10): $R_t$=0.65 min; MS (ESIpos): m/z=449 [M+H]$^+$;

$^1$H-NMR (400 MHz, DMSO-d$_6$): δ=11.42 (br. s, 1H), 8.54 (s, 1H), 8.35 (s, 1H), 8.19 (s, 1H), 8.14 (s, 1H), 7.56 (s, 1H), 4.51 (br. s, 2H), 3.53-3.37 (m, 4H), 3.13-2.97 (m, 4H), 2.24-2.14 (m, 2H), 2.03-1.68 (m, 5H).

Example 26

2-(5-Bromopyridin-2-yl)-4-[4-(trifluoromethyl)-1H-imidazol-1-yl]-1,2-dihydro-3H-pyrazol-3-one hydrochloride

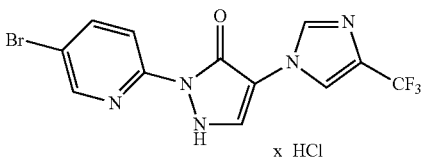 [SMILES: O=c1c(-n2cnc(C(F)(F)F)c2)c[nH]n1-c1ccc(Br)cn1 ; Cl]

x HCl

A mixture of 369 mg (1.3 mmol) of the compound from Example 44A, 250 mg (1.3 mmol) of the compound from Example 10A and 46 mg (0.3 mmol) p-toluenesulfonic acid in 5 ml THF is reacted in a single mode microwave (Emrys Optimizer) at 170° C. for 30 min. After addition of 2 ml formic acid to the reaction solution, the solid which has precipitated out is filtered off, stirred with 3 ml of a 4 N solution of hydrogen chloride in dioxane, filtered off again, washed first with acetonitrile and then with diethyl ether and dried in vacuo.

Yield: 163 mg (30% of th.)

LC-MS (Method 10): $R_t$=1.06 min; MS (ESIpos): m/z=374 [M+H]$^+$;

$^1$H-NMR (400 MHz, DMSO-d$_6$): δ=8.65 (s, 1H), 8.45 (s, 1H), 8.38-8.23 (m, 2H), 8.19 (s, 1H), 8.15 (s, 1H).

Example 27

2-[5-(Hydroxymethyl)pyridin-2-yl]-4-(1H-imidazol-1-yl)-1,2-dihydro-3H-pyrazol-3-one hydrochloride

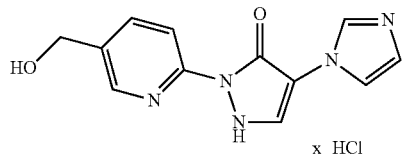 [SMILES: O=c1c(-n2ccnc2)c[nH]n1-c1ccc(CO)cn1 ; Cl]

x HCl 200 mg (1.0 mmol) of the compound from Example 42A and 133 mg (1.0 mmol) of the compound from Example 4A are dissolved in 2 ml ethanol and 44 mg (0.2 mmol) camphor-10-sulfonic acid are added. The mixture is stirred under reflux for 12 h. The cooled reaction mixture is concentrated in vacuo. After purification twice by means of preparative HPLC (RP18 column; mobile phase: acetonitrile/water gradient with addition of 0.1% formic acid), 1 ml of a 4 N solution of hydrogen chloride in dioxane is added to the product fraction, the mixture is stirred for 1 h, the solvent is removed completely on a rotary evaporator and the residue is dried in vacuo.

Yield: 86 mg (31% of th.)

LC-MS (Method 1): $R_t$=1.77 min; MS (ESIpos): m/z=258 [M+H]$^+$;

$^1$H-NMR (400 MHz, DMSO-d$_6$): δ=9.50 (s, 1H), 8.51 (s, 1H), 8.47 (s, 1H), 8.29 (d, 1H), 8.09-8.01 (m, 2H), 7.87 (s, 1H), 3.58 (s, 2H).

Example 28

2-[6-(Dimethylamino)pyrimidin-4-yl]-4-[4-(trifluoromethyl)-1H-imidazol-1-yl]-1,2-dihydro-3H-pyrazol-3-one

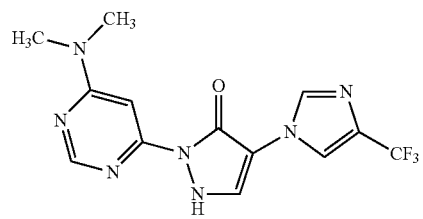 [SMILES: CN(C)c1cc(-n2[nH]cc(-n3cnc(C(F)(F)F)c3)c2=O)ncn1]

8.3 g (27.7 mmol) of the compound from Example 44A, 4.0 g (27.7 mmol) of the compound from Example 7A and 1.0 g (5.5 mmol) p-toluenesulfonic acid are reacted in a mixture of 10 ml ethanol and 5 ml THF in a single mode microwave (Emrys Optimizer) at 140° C. for 1 h. The precipitate which has separated out is filtered off, the residue on the filter is washed with a mixture of ethanol and diethyl ether and the product is dried in vacuo.

Yield: 1.3 mg (14% of th.)

LC-MS (Method 10): $R_t$=0.84 min; MS (ESIpos): m/z=340 [M+H]$^+$;

¹H-NMR (400 MHz, DMSO-d₆): δ=8.50 (s, 1H), 8.24 (s, 1H), 8.15 (s, 1H), 8.11 (s, 1H), 7.28 (s, 1H), 2.54 (s, 6H).

The compounds listed in Table 5 are prepared analogously to the examples given from the corresponding educts:

TABLE 5

| Example no. | Structure | Educts; preparation analogously to [example]; yield (% of th.) | MS (ESI) [M + H]⁺; LC-MS/HPLC: R$_t$ (method) | ¹H-NMR (400 MHz, DMSO-d₆) |
|---|---|---|---|---|
| 29 | (structure) x HCl | 3A, 19A [16] 11% | m/z = 254; 2.41 min (Method 1) | δ = 9.00 (s, 1H), 8.62 (s, 1H), 8.58-8.41 (m, 3H), 7.91 (s, 1H). |
| 30 | (structure) x HCl | 3A, 5A [16] 1% | m/z = 272; 1.77 min (Method 1) | δ = 9.45-9.21 (m, 2H), 8.67 (s, 1H), 8.52-8.41 (m, 2H), 8.35 (d, 1H), 8.21 (s, 1H), 8.41 (s, 1H), 4.23-4.20 (m, 2H), 2.61-2.56 (m, 3H). |
| 31 | (structure) x HCl | 3A, 9A [16] 70% | m/z = 307; 2.30 min (Method 1) | δ = 8.98 (d, 1H), 8.70-8.55 (m, 2H), 8.52 (dd, 1H), 8.45 (s, 1H), 7.92 (s, 1H), 3.36 (s, 3H). |
| 32 | (structure) | 3A, 24A [16] 3% | m/z = 358; 0.91 min (Method 10) | δ = 8.43 (s, 1H), 8.38 (d, 1H), 8.34 (s, 1H), 8.22 (d, 1H), 7.92 (d, 1H), 7.89 (s, 1H), 7.51 (t, 1H), 4.19 (d, 2H), 1.39 (s, 9H). |
| 33 | (structure) x HCl | 42A [27] 34% | m/z = 228; 1.76 min (Method 1) | δ = 8.49 (d, 1H), 8.31 (d, 1H), 8.23 (s, 2H), 8.03 (dt, 1H), 7.59 (s, 1H), 7.35 (dt, 1H), 7.16 (s, 1H). |
| 34 | (structure) x HCl | 42A, 17A [27] 3% | m/z = 229; 0.53 min (Method 1) | δ = 9.55 (s, 1H), 8.75-8.55 (m, 3H), 8.09 (s, 1H), 7.88 (s, 1H). |
| 35 | (structure) | 42A, 9A [16] 48% | m/z = 306; 1.90 min (Method 1) | δ = 8.85 (s, 1H), 8.72 (s, 1H), 8.58 (s, 1H), 8.38 (s, 1H), 7.82 (dd, 2H), 6.81 (s, 1H), 3.12 (s, 3H). |
| 36 | (structure) | 42A [27] 10% | m/z = 262; 2.08 min (Method 1) | δ = 9.48 (s, 1H), 8.48 (s, 1H), 8.04 (s, 1H), 7.83 (s, 1H), 2.32 (s, 3H), 2.27 (s, 3H). |

TABLE 5-continued

| Example no. | Structure | Educts; preparation analogously to [example]; yield (% of th.) | MS (ESI) [M + H]+; LC-MS/ HPLC: R, (method) | 1H-NMR (400 MHz, DMSO-d6) |
|---|---|---|---|---|
| 37 | (pyridin-2-yl pyrazolone with triazole) x HCl | 43A [27] 35% | m/z = 229; 2.20 min (Method 1) | δ = 8.88 (s, 1H), 8.52 (d, 1H), 8.32-8.23 (m, 2H), 8.08 (t, 1H), 7.39 (t, 1H). |
| 38 | (hydroxymethyl-pyridinyl pyrazolone with triazole) x HCl | 43A, 4A [27] 8% | m/z = 259; 2.09 min (Method 1) | δ = 8.86 (s, 1H), 8.43 (s, 1H), 8.32-8.11 (m, 3H), 8.07-7.92 (m, 1H), 4.58 (s, 2H). |
| 39 | (piperidinyl-pyrimidinyl pyrazolone with triazole) x HCl | 43A, 8A [27] 8% | m/z = 313; 2.70 min (Method 1) | δ = 8.92 (s, 1H), 8.51 (s, 1H), 8.23 (s, 1H), 8.11 (s, 1H), 7.50 (s, 3H), 3.75-3.70 (m, 4H), 1.73-1.64 (m, 2H), 1.60-1.55 (m, 4H). |
| 40 | (pyridin-2-yl pyrazolone with CF3-imidazole) x HCl | 44A [27] 5% | m/z = 296; 1.96 min (Method 4) | δ = 8.52 (d, 1H), 8.42-8.22 (m, 2H), 8.19 (s, 1H), 8.16 (s, 1H), 8.06 (t, 1H), 7.39 (t, 1H). |
| 41 | (hydroxymethyl-pyridinyl pyrazolone with methyl-triazole) x HCl | 20A, 4A [27] 9% | m/z = 273; 2.33 min (Method 1) | δ = 8.44 (s, 1H), 8.29 (s, 1H), 8.21 (s, 1H), 8.14 (s, 1H), 7.99 (s, 1H), 4.58 (s, 2H), 2.32 (s, 3H). |
| 42 | (pyridin-2-yl pyrazolone with methyl-triazole) x HCl | 20A [27] 6% | m/z = 243; 2.50 min (Method 1) | δ = 8.52 (d, 1H), 8.32 (s, 1H), 8.25 (d, 1H), 8.15 (s, 1H), 8.09 (t, 1H), 7.40 (dd, 1H), 2.31 (s, 3H). |
| 43 | (pyrazinyl pyrazolone with methyl-triazole) x HCl | 20A [27] 23% | m/z = 244; 2.25 min (Method 1) | δ = 9.54 (s, 1H), 8.65-8.61 (m, 2H), 8.51 (s, 1H), 8.18 (s, 1H), 2.32 (s, 3H). |
| 44 | (piperidinyl-pyrimidinyl pyrazolone with isopropyl-triazole) x HCl | 48A, 8A [27] 12% | m/z = 355; 3.88 min (Method 11) | δ = 8.52 (s, 1H), 8.20 (s, 1H), 8.14 (s, 1H), 7.42 (s, 1H), 3.75-3.71 (m, 4H), 3.07-3.03 (m, 1H), 1.73-1.52 (m, 6H), 1.28 (d, 6H). |

TABLE 5-continued

| Example no. | Structure | Educts; preparation analogously to [example]; yield (% of th.) | MS (ESI) [M + H]+; LC-MS/HPLC: $R_t$ (method) | $^1$H-NMR (400 MHz, DMSO-$d_6$) |
|---|---|---|---|---|
| 45 | (pyridine with CH2OH, pyrazolone, triazole with isopropyl) × HCl | 48A, 4A [27] 15% | m/z = 301; 2.71 min (Method 1) | δ = 8.45 (s, 1H), 8.32 (s, 1H), 8.21 (d, 1H), 8.16 (s, 1H), 8.01 (s, 1H), 4.58 (s, 2H), 3.09-3.06 (m, 1H), 1.28 (d, 6H). |
| 46 | (pyridine, pyrazolone, triazole with isopropyl) × HCl | 48A [27] 11% | m/z = 271; 2.70 min (Method 1) | δ = 8.52 (d, 1H), 8.33 (s, 1H), 8.26 (d, 1H), 8.15 (s, 1H), 8.07 (t, 1H), 7.41 (dd, 1H), 3.10-3.07 (m, 1H), 1.28 (d, 6H). |
| 47 | (pyridine, pyrazolone, 2-methylimidazole) × HCl | 49A [27] 5% | m/z = 242; 1.85 min (Method 1) | δ = 8.52 (d, 1H), 8.30 (s, 1H), 8.27 (d, 1H), 8.09 (t, 1H), 8.73 (d, 1H), 7.41 (t, 1H), 2.58 (s, 3H). |
| 48 | (pyridine with CH2OH, pyrazolone, 2-methylimidazole) × CF3COOH | 49A, 4A [27] 1% | m/z = 272; 0.47 min (Method 1) | |
| 49 | (pyridine with CH2OH, pyrazolone, methylisoxazole) × HCl | 50A, 4A [27] 5% | m/z = 273; 2.63 min (Method 1) | δ = 8.43 (s, 1H), 8.27-8.17 (m, 2H), 8.03 (dd, 1H), 6.39 (s, 1H), 4.58 (s, 2H), 2.23 (s, 3H). |
| 50 | (pyridine, pyrazolone, methylisoxazole) × HCl | 50A [27] 19% | m/z = 243; 2.88 min (Method 1) | δ = 8.49 (d, 1H), 8.29-8.18 (m, 2H), 8.09 (t, 1H), 7.38 (dd, 1H), 6.40 (s, 1H), 2.26 (s, 3H). |
| 51 | (4-methylpyridine, pyrazolone, methylisoxazole) × HCl | 50A, 1A [27] 14% | m/z = 257; 2.95 min (Method 1) | δ = 8.24 (d, 1H), 8.14 (s, 1H), 8.05 (s, 1H), 7.25 (d, 1H), 6.33 (s, 1H), 2.47 (s, 3H), 2.23 (s, 3H). |

TABLE 5-continued

| Example no. | Structure | Educts; preparation analogously to [example]; yield (% of th.) | MS (ESI) [M + H]+; LC-MS/HPLC: R$_t$ (method) | $^1$H-NMR (400 MHz, DMSO-d$_6$) |
|---|---|---|---|---|
| 52 | (piperidine-pyrimidine-pyrazolone-3-methylisoxazole) × HCl | 50A, 8A [27] 1% | m/z = 327; 1.82 min (Method 8) | δ = 8.49 (s, 1H), 8.05 (s, 1H), 7.29 (s, 1H), 6.21 (s, 1H), 3.76-3.72 (m, 4H), 2.21 (s, 3H), 1.72-1.53 (m, 6H). |
| 53 | (pyridine-pyrazolone-imidazole-CN) × HCl | 45A [27] 3% | m/z = 253; 2.51 min (Method 1) | δ = 8.52 (d, 1H), 8.48 (s, 1H), 8.35 (s, 1H), 8.30 (d, 1H), 8.23 (s, 1H), 8.07 (s, 1H), 7.39 (t, 1H). |
| 54 | (HOCH$_2$-pyridine-pyrazolone-methylimidazole) × HCl | 46A, 4A [27] 7% | m/z = 272; 1.92 min (Method 1) |  |
| 55 | (pyridine-pyrazolone-methylimidazole) × HCl | 46A [27] 9% | m/z = 242; 1.91 min (Method 1) | δ = 9.42 (s, 1H), 8.53 (d, 1H), 8.50 (s, 1H), 8.32 (d, 1H), 8.10 (dd, 1H), 7.80 (s, 1H), 7.41 (dd, 1H), 2.36 (s, 3H). |
| 56 | (H$_3$C-pyridine-pyrazolone-imidazole-CF$_3$) × HCl | 44A, 20A [16] 35% | m/z = 310; 1.87 min (Method 8) | δ = 8.34 (d, 2H), 8.19-8.15 (m, 3H), 7.88 (d, 1H), 2.35 (s, 3H). |
| 57 | (H$_3$C-pyridine-pyrazolone-triazole) × HCl | 3A, 20A [16] 26% | m/z = 243; 1.27 min (Method 8) | δ = 8.43 (s, 1H), 8.34 (d, 2H), 8.14 (d, 1H), 7.92-7.90 (m, 2H), 2.36 (s, 3H). |
| 58 | (H$_3$C, Br-pyridine-pyrazolone-triazole) × HCl | 3A, 23A [16] 10% | m/z = 321; 0.93 min (Method 10) | δ = 8.61 (s, 1H), 8.44-8.41 (m, 2H), 8.30 (s, 1H), 7.90 (s, 1H), 2.47 (s, 3H). |
| 59 | (H$_3$CH$_2$C-pyrimidine-pyrazolone-triazole) × HCl | 3A, 28A [16] 7% | m/z = 258; 1.15 min (Method 10) | δ = 9.05 (s, 1H), 8.63 (s, 1H), 8.45 (d, 1H), 8.30 (s, 1H), 7.91 (d, 1H), 2.85 (q, 2H), 1.27 (t, 3H). |

TABLE 5-continued

| Example no. | Structure | Educts; preparation analogously to [example]; yield (% of th.) | MS (ESI) [M + H]+; LC-MS/ HPLC: $R_t$ (method) | 1H-NMR (400 MHz, DMSO-$d_6$) |
|---|---|---|---|---|
| 60 | 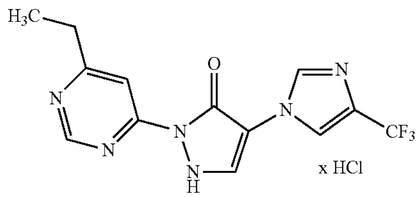 [SMILES: CCc1cc(-n2[nH]cc(-n3cnc(C(F)(F)F)c3)c2=O)ncn1] | 44A, 28A [16] 7% | m/z = 325; 1.62 min (Method 10) | δ = 9.03 (s, 1H), 8.58 (s, 1H), 8.30 (s, 1H), 8.21 (s, 1H), 8.17 (s, 1H), 2.85 (q, 2H), 1.28 (t, 3H). |
| 61 | 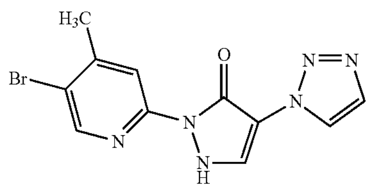 [SMILES: Cc1cc(-n2[nH]cc(-n3ccnn3)c2=O)ncc1Br] | 3A, 23A [16] 17% | m/z = 321; 0.92 min (Method 10) | δ = 8.61 (s, 1H), 8.48-8.42 (m, 2H), 8.31 (s, 1H), 7.91 (s, 1H), 2.47 (s, 3H). |

Example 62

6-[5-Oxo-4-(1H-1,2,3-triazol-1-yl)-2,5-dihydro-1H-pyrazol-1-yl]pyridine-3-carboxylic acid tert-butyl ester hydrochloride

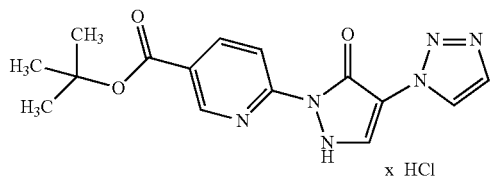 [SMILES: CC(C)(C)OC(=O)c1ccc(-n2[nH]cc(-n3ccnn3)c2=O)nc1 ; Cl]

3.2 g (15.0 mmol) of the compound from Example 3A are initially introduced into 100 ml ethanol. 3.1 g (15.0 mmol) of the compound from Example 22A and 571 mg (3.0 mmol) p-toluenesulfonic acid monohydrate are added and the mixture is stirred under reflux for 16 h. The mixture is then concentrated and the residue is purified by means of preparative HPLC (RP18 column; mobile phase: acetonitrile/water gradient with addition of 0.1% TFA). The product-containing fractions are combined, the majority of the solvent is removed and the solid formed is filtered off. This is dried under a high vacuum and a 4 N solution of hydrogen chloride in dioxane is then added. The mixture is stirred at RT for 1 h and the solid is filtered off and dried under a high vacuum.

Yield: 1.6 g (28% of th.)

LC-MS (Method 1): $R_t$=3.32 min; MS (ESIpos): m/z=329 [M+H]+;

1H-NMR (400 MHz, DMSO-$d_6$): δ=8.94 (s, 1H), 8.53 (s, 1H), 8.50-8.40 (m, 3H), 7.91 (s, 1H), 1.58 (s, 9H).

Example 63

6-[4-(1H-Imidazol-1-yl)-5-oxo-2,5-dihydro-1H-pyrazol-1-yl]pyridine-3-carboxylic acid tert-butyl ester hydrochloride

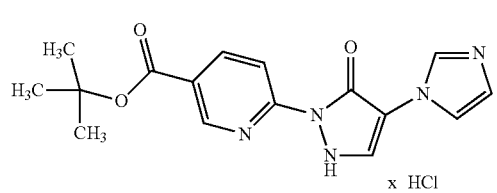 [SMILES: CC(C)(C)OC(=O)c1ccc(-n2[nH]cc(-n3ccnc3)c2=O)nc1 ; Cl]

3.1 g (15.0 mmol) of the compound from Example 42A are initially introduced into 100 ml ethanol. 3.1 g (15.0 mmol) of the compound from Example 22A and 571 mg (3.0 mmol) p-toluenesulfonic acid monohydrate are added and the mixture is first stirred at RT for 16 h. It is subsequently stirred under reflux for a further 24 h and the solvent is then removed. The residue is purified by means of preparative HPLC (RP18 column; mobile phase: acetonitrile/water gradient with addition of 0.1% TFA). The product fractions are combined and the majority of the acetonitrile contained therein is removed. The solution which remains is lyophilized. A 4 N solution of hydrogen chloride in dioxane is added to the lyophilisate and the mixture is stirred at RT for 1 h. The solid is filtered off and dried under a high vacuum.

Yield: 1.3 g (23% of th.)

LC-MS (Method 7): $R_t$=0.99 min; MS (ESIpos): m/z=328 [M+H]+;

1H-NMR (400 MHz, DMSO-$d_6$): δ=9.55 (s, 1H), 8.94 (s, 1H), 8.70 (s, 1H), 8.53-8.42 (m, 2H), 8.10 (s, 1H), 7.88 (s, 1H), 1.58 (s, 9H).

Example 64

6-{5-Oxo-4-[4-(trifluoromethyl)-1H-imidazol-1-yl]-2,5-dihydro-1H-pyrazol-1-yl}pyridine-3-carboxylic acid tert-butyl ester hydrochloride

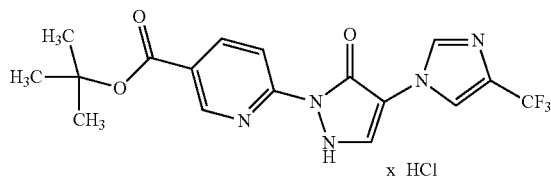 [SMILES: CC(C)(C)OC(=O)c1ccc(-n2[nH]cc(-n3cnc(C(F)(F)F)c3)c2=O)nc1 ; Cl]

4.2 g (15.0 mmol) of the compound from Example 44A are initially introduced into 100 ml ethanol. 3.1 g (15.0 mmol) of the compound from Example 22A and 571 mg (3.0 mmol) p-toluenesulfonic acid monohydrate are added and the mixture is stirred at RT for 16 h. The solvent is then removed and the residue is purified by means of preparative HPLC (RP18 column; mobile phase: acetonitrile/water gradient with addition of 0.1% TFA). The product fractions are combined and the majority of the acetonitrile contained therein and some of the water are removed. The solid formed is filtered off and is dried in air. 20 ml of a 4 N solution of hydrogen chloride in dioxane are then added and the mixture is stirred at RT for 1 h. The solid is filtered off and purified again via preparative HPLC (RP18 column; mobile phase: acetonitrile/water gradient with addition of 0.1% TFA). The product fractions are combined, 1 N hydrochloric acid is added and the mixture is lyophilized.

Yield: 750 mg (12% of th.)

LC-MS (Method 7): $R_t$=2.10 min; MS (ESIpos): m/z=396 [M+H]$^+$;

$^1$H-NMR (400 MHz, DMSO-d$_6$): δ=8.93 (s, 1H), 8.59-8.38 (m, 3H), 8.19 (s, 1H), 8.14 (s, 1H), 1.59 (s, 9H).

Example 65

6-[5-Oxo-4-(1H-1,2,3-triazol-1-yl)-2,5-dihydro-1H-pyrazol-1-yl]pyridine-3-carboxylic acid hydrochloride

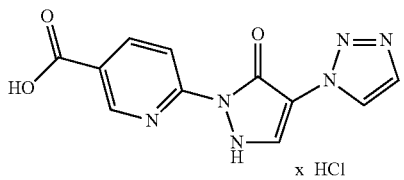 [SMILES: O=C(O)c1ccc(-n2[nH]cc(-n3ccnn3)c2=O)nc1 ; Cl]

50 mg (0.1 mmol) of the compound from Example 62 are dissolved in 1 ml of a 1:1 mixture of methylene chloride and TFA and the mixture is stirred at RT for 1 h. The reaction solution is concentrated in vacuo, the residue is suspended in 2 ml 1 N hydrochloric acid and the suspension is then lyophilized.

Yield: 42 mg (99% of th.)

LC-MS (Method 9): $R_t$=0.82 min; MS (ESIpos): m/z=273 [M+H]$^+$;

$^1$H-NMR (400 MHz, DMSO-d$_6$): δ=8.99 (s, 1H), 8.53 (s, 1H), 8.51-8.41 (m, 3H), 7.91 (s, 1H).

The preparation of the target compounds listed in Table 6 is carried out analogously to Example Compound 65:

TABLE 6

| Example no. | Structure | Educt; yield (% of th.) | MS (ESI) [M + H]$^+$; LC-MS: $R_t$ (method) | $^1$H-NMR (400 MHz, DMSO-d$_6$) |
|---|---|---|---|---|
| 66 | ![structure] | 63 98% | m/z = 272; 1.87 min (Method 1) | δ = 13.50 (br. s, 1H), 9.52 (s, 1H), 8.98 (s, 1H), 8.68 (s, 1H), 8.49 (s, 1H), 8.09 (s, 1H), 7.87 (s, 1H). |
| 67 | ![structure] | 64 92% | m/z = 340; 1.90 min (Method 4) | δ = 8.98 (s, 1H), 8.51 (s, 1H), 8.48 (s, 2H), 8.21 (s, 1H), 8.18 (s, 1H). |

Example 68

6-[5-Oxo-4-(1H-1,2,3-triazol-1-yl)-2,5-dihydro-1H-pyrazol-1-yl]pyridine-3-carboxylic acid

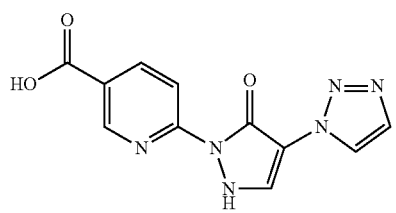 [SMILES: O=C(O)c1ccc(-n2[nH]cc(-n3ccnn3)c2=O)nc1]

491 mg (1.8 mmol, 80% purity) of the compound from Example 3A and 289 mg (1.6 mmol) 6-hydrazinonicotinic acid ethyl ester [for the preparation see WO 2006/114213] are stirred in 10 ml acetic acid at RT for 12 h. Thereafter, 120 mg (0.7 mmol) 6-hydrazinonicotinic acid ethyl ester are again added to the reaction mixture and the mixture is stirred again at RT for 13 h. After standing at RT for a further two days, the reaction solution is concentrated in vacuo, the residue is taken up in ethyl acetate, the mixture is washed neutral with saturated sodium bicarbonate solution and the organic phase is dried over sodium sulfate, filtered and concentrated on a rotary evaporator. The intermediate product obtained in this way is dissolved in 10 ml ethanol, 0.3 ml (1.8 mmol) of a 30% strength sodium methylate solution in methanol are added and the mixture is stirred at RT for 17 h. The reaction solution is adjusted to pH 5 with 1 N hydrochloric acid and is subsequently stirred at RT for a further 2 h. It is concentrated in vacuo, acetonitrile is added to the residue, the precipitate which has separated out is filtered off and the residue on the filter is washed with diethyl ether and dried in vacuo. 9.4 ml 0.1 M ethanolic potassium hydroxide solution are added to the ester obtained in this way and the mixture is stirred at RT for 16 h. The reaction solution is adjusted to pH 2 with 1 N hydrochloric acid, the solvent is removed on a rotary evaporator, the residue is taken up in water and the mixture is extracted with ethyl acetate. The crystals which have precipitated out from the aqueous phase are filtered off, the residue on the filter is washed with diethyl ether and the product is dried in vacuo.

Yield: 32 mg (7% of th.)

LC-MS (Method 1): $R_t$=2.31 min; MS (ESIpos): m/z=273 [M+H]$^+$;

$^1$H-NMR (400 MHz, DMSO-$d_6$): δ=13.49 (br. s, 1H), 9.00 (s, 1H), 8.71-8.33 (m, 4H), 8.41 (s, 1H).

Example 69

6-[5-Oxo-4-(1H-1,2,3-triazol-1-yl)-2,5-dihydro-1H-pyrazol-1-yl]nicotinic acid ethyl ester

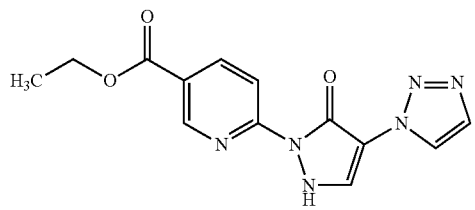 [SMILES: CCOC(=O)c1ccc(-n2[nH]cc(-n3ccnn3)c2=O)nc1]

2.7 g (13.1 mmol) Example Compound 3A, 2.0 g (13.1 mmol) Example Compound 6A and 1.1 g (6.5 mmol) p-toluenesulfonic acid are stirred under reflux in 50 ml ethanol for 16 h. 50 ml DMF are added to the cooled reaction mixture and the mixture is then stirred at a bath temperature of 130° C. for a further 10 h. The reaction solution is concentrated in vacuo and 10 ml ethanol and 1 ml conc. sulfuric acid are added to the residue. The mixture is subsequently stirred at the boiling point for 12 h. Water is added to the cooled reaction mixture, the solid is filtered off, the residue on the filter is rinsed with ethanol and the product is dried in vacuo.

Yield: 0.14 g (3% of th.)

LC-MS (Method 9): $R_t$=2.89 min; MS (ESIpos): m/z=300 [M+H]$^+$;

$^1$H-NMR (400 MHz, DMSO-$d_6$): δ=9.00 (s, 1H), 8.57-8.54 (m, 1H), 8.53-8.46 (m, 2H), 8.45 (s, 1H), 7.91 (s, 1H), 4.38 (q, 2H), 1.35 (t, 3H).

Example 70

2-[5-(Aminomethyl)pyridin-2-yl]-4-(1H-1,2,3-triazol-1-yl)-1,2-dihydro-3H-pyrazol-3-one hydrochloride

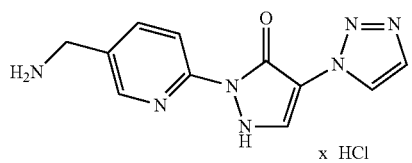 [SMILES: NCc1ccc(-n2[nH]cc(-n3ccnn3)c2=O)nc1 ; Cl]

x HCl 83 mg (0.2 mmol) Example Compound 32 are stirred in 5 ml of a 4 M solution of hydrogen chloride in dioxane at RT for 2 h. Thereafter, the mixture is concentrated in vacuo and the residue is chromatographed by means of preparative HPLC (RP18 column; gradient: acetonitrile/water with addition of 0.1% TFA). The combined product fractions are concentrated and 2 ml 1 N hydrochloric acid are added to the residue. The resulting suspension is freeze-dried. The lyophilisate is stirred in ethanol, the solid is filtered off and the crystals are dried in vacuo.

Yield: 10 mg (14% of th.)

LC-MS (Method 8): $R_t$=0.76 min; MS (ESIpos): m/z=258 [M+H]$^+$;

$^1$H-NMR (400 MHz, DMSO-$d_6$): δ=8.64 (s, 1H), 8.53 (s, 3H), 8.47 (s, 2H), 8.31 (s, 1H), 8.18 (s, 1H), 7.91 (s, 1H), 4.12-4.10 (m, 2H).

Example 71

2-(6-Morpholin-4-ylpyrimidin-4-yl)-4-(1H-1,2,3-triazol-1-yl)-1,2-dihydro-3H-pyrazol-3-one

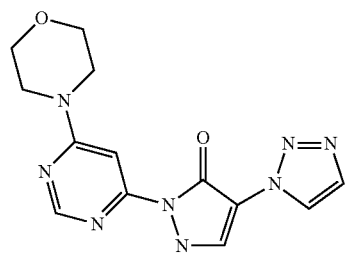

1.9 g (8.8 mmol) of the compound from Example 3A and 1.9 g (9.7 mmol) of the compound from Example 16A are initially introduced into 25 ml ethyl acetate and 504 mg (4.4 mmol) TFA are added at RT. The mixture is stirred under reflux for 16 h, then cooled to 5° C. and subsequently stirred for a further 2 h. The solid formed is filtered off, washed with ethyl acetate and dried first in air and thereafter under a high vacuum. 1.7 g of product are obtained.

The mother liquor is combined with the wash solution and the solvent is removed. According to LC-MS, the residue (2.4 g) still contains the intermediate 3-[2-(6-morpholin-4-ylpyrimidin-4-yl)hydrazino]-2-(1H-1,2,3-triazol-1-yl)prop-2-enoic acid ethyl ester (intermediate stage of the cyclization), which is used directly for the preparation of Example 72 (see there).

Yield: 1.7 g (61% of th.)

Example 72

2-(6-Morpholin-4-ylpyrimidin-4-yl)-4-(1H-1,2,3-triazol-1-yl)-1,2-dihydro-3H-pyrazol-3-one hydrochloride

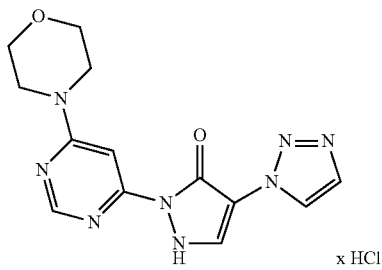 [SMILES: O=c1c(-n2ccnn2)c[nH]n1-c1cc(N2CCOCC2)ncn1]

Batch 1: 7.5 ml of a 4 N solution of hydrogen chloride in dioxane are added to 1.7 g (5.4 mmol) of the compound from Example 71. The mixture is stirred at RT, 5 ml dioxane are added and the mixture is stirred at RT for 16 h. The solid is filtered off and washed with 5 ml dioxane. The mixture is dried under a high vacuum for 16 h, 10 ml methanol are then added and the mixture is stirred at RT for 1 h. The solid is filtered off, washed with 4 ml methanol and dried under a high vacuum. 1.6 g of the title compound are obtained.

Batch 2: A further amount of the title compound is obtained as follows: The residue (2.4 g) obtained from the mother liquor during the synthesis of Example Compound 71, which contains the open-ring intermediate state of the cyclization, 3-[2-(6-morpholin-4-ylpyrimidin-4-yl)hydrazino]-2-(1H-1,2,3-triazol-1-yl)prop-2-enoic acid ethyl ester, is dissolved in 12 ml ethanol and 1.5 ml 30% strength sodium methylate solution in methanol are added at RT, while stirring. The mixture is subsequently stirred at RT for 45 min, then adjusted to pH 5 with 2 N hydrochloric acid and subsequently stirred at RT for a further 16 h. The mixture is cooled to 10° C. and the solid is filtered off and washed with 3.5 ml dioxane. The mixture is dried under a high vacuum for 16 h, 5 ml methanol are then added and the mixture is subsequently stirred at RT for 1 h. The solid is filtered off, washed with 2 ml methanol and dried under a high vacuum to give a further 997 mg of the title compound in this way.

Yield: together 2.6 g (83% of th.)

LC-MS (Method 6): $R_t$=0.89 min; MS (ESIpos): m/z=315 [M+H]$^+$;

$^1$H-NMR (400 MHz, DMSO-d$_6$): δ=8.54 (s, 1H), 8.39 (s, 1H), 8.28 (s, 1H), 7.88 (s, 1H), 7.42 (s, 1H), 3.71 (s, 8H).

Example 73

4-(1H-Imidazol-1-yl)-2-(6-morpholin-4-ylpyrimidin-4-yl)-1,2-dihydro-3H-pyrazol-3-one trifluoroacetate

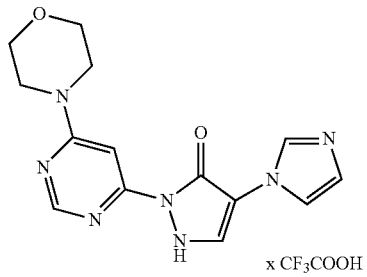 [SMILES: O=c1c(-n2ccnc2)c[nH]n1-c1cc(N2CCOCC2)ncn1]

209 mg (1.0 mmol) of the compound from Example 42A are dissolved in 7 ml THF. 195 mg (1.0 mmol) of the compound from Example 16A and 38 mg (0.2 mmol) p-toluenesulfonic acid monohydrate are added at RT and the mixture is then reacted in a single mode microwave (CEM Explorer) at 150° C. for 1 h. The mixture obtained is then purified directly by means of preparative HPLC (RP18 column; mobile phase: acetonitrile/water gradient with addition of 0.1% TFA).

Yield: 71 mg (17% of th.)

LC-MS (Method 1): $R_t$=2.03 min; MS (ESIpos): m/z=314 [M+H]$^+$;

$^1$H-NMR (400 MHz, DMSO-d$_6$): δ=9.38 (s, 1H), 8.57 (s, 1H), 8.31 (s, 1H), 8.02 (s, 1H), 7.79 (s, 1H), 7.47 (s, 1H), 3.72 (s, 8H).

Example 74

4-(1H-Imidazol-1-yl)-2-(6-morpholin-4-ylpyrimidin-4-yl)-1,2-dihydro-3H-pyrazol-3-one hydrochloride

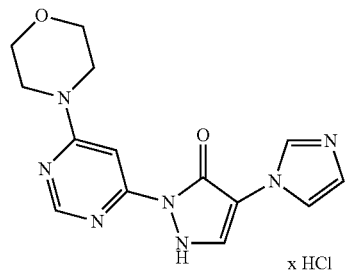 [SMILES: O=c1c(-n2ccnc2)c[nH]n1-c1cc(N2CCOCC2)ncn1]

0.5 ml of a 4 N solution of hydrogen chloride in dioxane are added to 60 mg (0.1 mmol) of the compound from Example 73 and the mixture is stirred at RT for 1 h. The solid is filtered off, washed twice with 0.5 ml dioxane each time and subsequently dried in vacuo.

Yield: 46 mg (94% of th.)

LC-MS (Method 1): $R_t$=0.91 min; MS (ESIpos): m/z=314 [M+H]$^+$;

$^1$H-NMR (400 MHz, DMSO-d$_6$): δ=9.46 (s, 1H), 8.57 (s, 1H), 8.35 (s, 1H), 8.06 (s, 1H), 7.82 (s, 1H), 7.46 (s, 1H), 3.73 (s, 8H).

---

At top of page (continuation from Example 71):

LC-MS (Method 9): $R_t$=0.90 min; MS (ESIpos): m/z=315 [M+H]$^+$;

$^1$H-NMR (400 MHz, DMSO-d$_6$): δ=8.42 (s, 1H), 8.38 (s, 1H), 8.01 (s, 1H), 7.73 (s, 1H), 7.70 (s, 1H), 3.71-3.65 (m, 4H), 3.57-3.51 (m, 4H).

Example 75

2-(6-Morpholin-4-ylpyrimidin-4-yl)-4-[4-(trifluoromethyl)-1H-imidazol-1-yl]-1,2-dihydro-3H-pyrazol-3-one hydrochloride

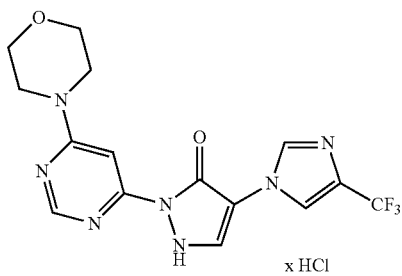 [SMILES: O=c1c(-n2cnc(C(F)(F)F)c2)c[nH]n1-c1cc(N2CCOCC2)ncn1]

309 mg (1.0 mmol) of the compound from Example 44A are dissolved in 7 ml THF. 195 mg (1.0 mmol) of the compound from Example 16A and 38 mg (0.2 mmol) p-toluenesulfonic acid monohydrate are added at RT and the mixture is then reacted in a single mode microwave (CEM Explorer) at 150° C. for 1 h. The mixture obtained is subsequently purified directly by means of preparative HPLC (RP18 column; mobile phase: acetonitrile/water gradient with addition of 0.1% TFA). The product fractions obtained are combined and the solvent is removed. A 4 N solution of hydrogen chloride in dioxane is added to the residue. The mixture is stirred at RT for 1 h and the solid is filtered off and dried under a high vacuum.

Yield: 77 mg (19% of th.)

LC-MS (Method 7): $R_t$=1.31 min; MS (ESIpos): m/z=382 [M+H]$^+$;

$^1$H-NMR (400 MHz, DMSO-d$_6$): δ=8.53 (s, 1H), 8.33 (s, 1H), 8.18 (s, 1H), 8.13 (s, 1H), 7.49 (s, 1H), 3.67 (s, 8H).

Example 76

1-[2-(6-Morpholin-4-ylpyrimidin-4-yl)-3-oxo-2,3-dihydro-1H-pyrazol-4-yl]-1H-imidazole-4-carbonitrile trifluoroacetate

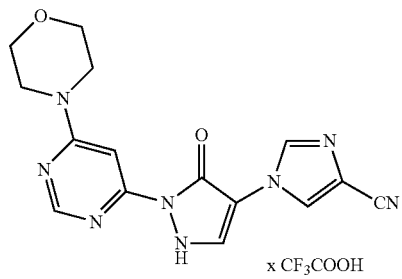 [SMILES: N#Cc1cn(-c2c[nH]n(-c3cc(N4CCOCC4)ncn3)c2=O)cn1]

976 mg (purity 72%, 3.0 mmol) of the compound from Example 45A are initially introduced into 20 ml THF. 586 mg (3.0 mmol) of the compound from Example 16A and 114 mg (0.6 mmol) p-toluenesulfonic acid monohydrate are added and the mixture is then reacted in a single mode microwave (CEM Explorer) at 150° C. for 1 h. The reaction mixture is first pre-purified chromatographically over silica gel (Biotage chromatography; mobile phase: methylene chloride/methanol 10:1 with addition of a little aqueous ammonia solution). The crude product obtained in this way is then purified further by means of preparative HPLC twice (RP18 column; mobile phase: acetonitrile/water gradient with addition of 0.1% TFA). The product fractions of the HPLC chromatography are combined, the same volume of water is added and lyophilization is carried out.

Yield: 11 mg (1% of th.)

LC-MS (Method 4): $R_t$=1.54 min; MS (ESIpos): m/z=339 [M+H]$^+$;

$^1$H-NMR (400 MHz, DMSO-d$_6$): δ=8.53 (s, 1H), 8.42 (s, 1H), 8.29 (s, 1H), 8.19 (s, 1H), 7.46 (s, 1H), 3.70-3.64 (m, 8H).

Example 77

1-[2-(6-Morpholin-4-ylpyrimidin-4-yl)-3-oxo-2,3-dihydro-1H-pyrazol-4-yl]-1H-imidazol-4-carboxamide hydrochloride

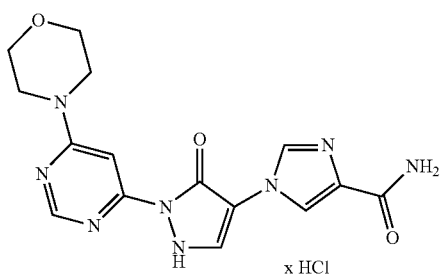 [SMILES: NC(=O)c1cn(-c2c[nH]n(-c3cc(N4CCOCC4)ncn3)c2=O)cn1]

976 mg (purity 72%, 3.0 mmol) of the compound from Example 45A are initially introduced into 20 ml THF. 586 mg (3.0 mmol) of the compound from Example 16A and 114 mg (0.6 mmol) p-toluenesulfonic acid monohydrate are added and the mixture is then reacted in a single mode microwave (CEM Explorer) at 150° C. for 1 h. The reaction mixture is first pre-purified chromatographically over silica gel (Biotage chromatography; mobile phase: methylene chloride/methanol 10:1 with addition of a little aqueous ammonia solution). The crude product obtained in this way is then purified further by means of preparative HPLC twice (RP18 column; mobile phase: acetonitrile/water gradient with addition of 0.1% TFA). The product fractions of the HPLC chromatography are combined, the mixture is concentrated in vacuo, the residue is taken up in 1 M hydrochloric acid and the solution is lyophilized.

Yield: 14 mg (1.2% of th.)

LC-MS (Method 10): $R_t$=0.47 min; MS (ESIpos): m/z=357 [M+H]$^+$;

$^1$H-NMR (400 MHz, DMSO-d$_6$): δ=9.20 (s, 1H), 8.57 (s, 1H), 8.53 (s, 1H), 8.29 (s, 1H), 8.23 (br. s, 1H), 7.80 (br. s, 1H), 7.49 (s, 1H), 3.72 (s, 8H).

Example 78

6-[4-(4-Cyano-1H-imidazol-1-yl)-5-oxo-2,5-dihydro-1H-pyrazol-1-yl]pyridine-3-carboxylic acid tert-butyl ester hydrochloride

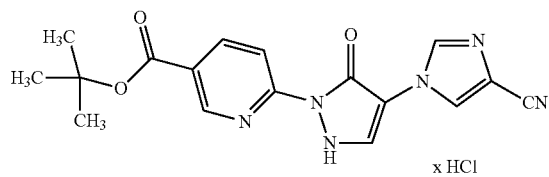 [SMILES: CC(C)(C)OC(=O)c1ccc(-n2[nH]cc(-n3cnc(C#N)c3)c2=O)nc1]

500 mg (purity 72%, 1.5 mmol) of the compound from Example 45A are initially introduced into 11 ml THF. 322 mg (1.5 mmol) of the compound from Example 22A and 58 mg (0.3 mmol) p-toluenesulfonic acid monohydrate are added and the mixture is reacted in a single mode microwave (CEM Explorer) at 150° C. for 3 h. Thereafter, the mixture is purified directly by means of preparative HPLC (RP18 column; mobile phase: acetonitrile/water gradient with addition of 0.1% TFA). The product fractions are combined and concentrated, a 1 N solution of hydrogen chloride in dioxane is added and the mixture is stirred at RT for 1 h. The precipitate is filtered off, washed twice with 0.5 ml dioxane each time and dried under a high vacuum.

Yield: 144 mg (24% of th.)

LC-MS (Method 8): $R_t$=2.10 min; MS (ESIpos): m/z=353 [M+H]$^+$;

$^1$H-NMR (400 MHz, DMSO-d$_6$): δ=8.94 (s, 1H), 8.54-8.42 (m, 4H), 8.20 (s, 1H), 1.58 (s, 9H).

The compounds listed in Table 7 are prepared analogously to the examples given from the corresponding educts. Instead of camphor-10-sulfonic acid, toluene-4-sulfonic acid monohydrate can also be employed.

TABLE 7

| Example no. | Structure | Educts; preparation analogously to [example]; yield (% of th.) | MS (ESI) [M + H]$^+$; LC-MS/ HPLC: $R_t$ (method) | $^1$H-NMR (DMSO-d$_6$) |
|---|---|---|---|---|
| 79 | F$_3$C-pyridine-pyrazolone-imidazole × HCl | 42A, 25A [16] 64% | m/z = 296; 0.92 min (Method 4) | (400 MHz): δ = 9.55 (s, 1H), 8.82 (d, 1H), 8.70 (d, 2H), 8.10 (d, 1H), 7.88 (d, 1H), 7.77 (dd, 1H). |
| 80 | H$_3$C, H$_3$C-pyridine-pyrazolone-triazole × HCl | 44A, 26A [16] 27% | m/z = 257; 1.32 min (Method 8) | (400 MHz): δ = 8.42 (s, 1H), 8.25 (s, 2H), 8.05 (s, 1H), 7.89 (s, 1H), 2.38 (s, 3H), 2.27 (s, 3H). |
| 81 | CH$_3$O-CH$_2$-pyridine-pyrazolone-triazole × HCl | 3A, 29A [16] 85% | m/z = 273; 0.64 min (Method 10) | (500 MHz): δ = 8.48 (s, 1H), 8.44 (s, 1H), 8.37 (s, 1H), 8.27 (s, 1H), 8.02 (d, 1H), 7.90 (s, 1H), 4.50 (s, 2H), 3.35 (s, 3H). |

Example 82

2-[5-(tert-Butoxymethyl)pyridin-2-yl]-4-(1H-1,2,3-triazol-1-yl)-1,2-dihydro-3H-pyrazol-3-one hydrochloride

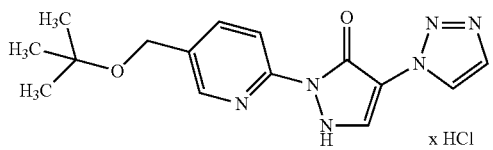 [SMILES: CC(C)(C)OCc1ccc(-n2[nH]cc(-n3ccnn3)c2=O)nc1]

631 mg (3.0 mmol) of the compound from Example 3A and 586 mg (3.0 mmol) of the compound from Example 18A are initially introduced into 10 ml ethanol. 114 mg (0.6 mmol) p-toluenesulfonic acid monohydrate are added and the mixture is stirred at RT for 16 h. The solvent is then removed and the residue is purified by means of preparative HPLC (RP18 column; mobile phase: acetonitrile/water gradient with addition of 0.1% TFA). The product fractions are combined and concentrated and the residue is dried under a high vacuum. 10 ml of a 4 N solution of hydrogen chloride in dioxane are added and the mixture is stirred at RT for 1 h. The solid is filtered off, washed with tert-butyl methyl ether and dried under a high vacuum.

Yield: 260 mg (25% of th.)

LC-MS (Method 8): $R_t$=1.77 min; MS (ESIpos): m/z=315 [M+H]$^+$;

$^1$H-NMR (400 MHz, DMSO-d$_6$): δ=8.47-8.42 (m, 2H), 8.35 (s, 1H), 8.22 (d, 1H), 7.99 (dd, 1H), 7.90 (s, 1H), 4.50 (s, 2H), 1.25 (s, 9H).

Example 83

4-(1H-1,2,3-Triazol-1-yl)-2-[4-(trifluoromethyl)pyridin-2-yl]-1,2-dihydro-3H-pyrazol-3-one hydrochloride

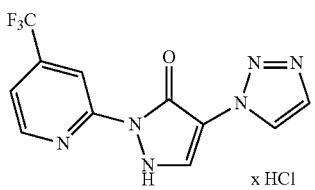 [SMILES: O=c1c(-n2ccnn2)c[nH]n1-c1cc(C(F)(F)F)ccn1]

631 mg (3.0 mmol) of the compound from Example 3A and 531 mg (3.0 mmol) of the compound from Example 25A are initially introduced into 10 ml ethanol. 114 mg (0.6 mmol) p-toluenesulfonic acid monohydrate are added and the mixture is stirred under reflux for 16 h. It is then concentrated and the residue is purified by means of preparative HPLC (RP18 column; mobile phase: acetonitrile/water gradient with addition of 0.1% TFA). The product fractions are combined, the solvent is removed and the residue is dried under a high vacuum. 20 ml of a 4 N solution of hydrogen chloride in dioxane are added and the mixture is stirred at RT for 1 h. The solid is filtered off, washed twice with tert-butyl methyl ether and dried under a high vacuum.

Yield: 231 mg (23% of th.)

LC-MS (Method 8): $R_t$=1.65 min; MS (ESIpos): m/z=297 [M+H]$^+$;

$^1$H-NMR (400 MHz, DMSO-d$_6$): δ=8.81 (d, 1H), 8.70 (s, 1H), 8.59 (s, 1H), 8.47 (s, 1H), 7.92 (s, 1H), 7.77 (d, 1H).

Example 84

2-[5-(2,2-Dimethylpropoxy)pyridin-2-yl]-4-(1H-1,2,3-triazol-1-yl)-1,2-dihydro-3H-pyrazol-3-one

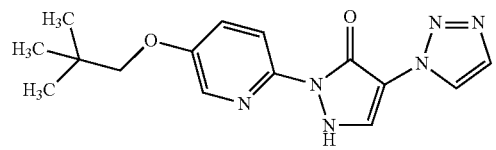 [SMILES: CC(C)(C)COc1ccc(-n2[nH]cc(-n3ccnn3)c2=O)nc1]

171 mg (0.8 mmol) of the compound from Example 3A and 455 mg (purity 35%, 0.8 mmol) of the compound from Example 12A are initially introduced into 7 ml ethanol. 31 mg (0.2 mmol) p-toluenesulfonic acid monohydrate are added and the mixture is stirred under reflux for 64 h. Thereafter, it is concentrated and the residue is purified by means of preparative HPLC (RP18 column; mobile phase: acetonitrile/water gradient with addition of 0.1% TFA). The product fractions are combined, the solvent is removed and the residue is dried under a high vacuum.

Yield: 28 mg (11% of th.)

LC-MS (Method 10): $R_t$=1.17 min; MS (ESIpos): m/z=315 [M+H]$^+$;

$^1$H-NMR (500 MHz, DMSO-d$_6$): δ=8.42 (s, 1H), 8.29 (s, 1H), 8.23 (s, 1H), 8.18-8.08 (m, 1H), 7.90 (s, 1H), 7.69 (dd, 1H), 3.78 (s, 2H), 1.02 (s, 9H).

Example 85

2-[5-(2,2-Dimethylpropoxy)pyridin-2-yl]-4-(1H-1,2,3-triazol-1-yl)-1,2-dihydro-3H-pyrazol-3-one hydrochloride

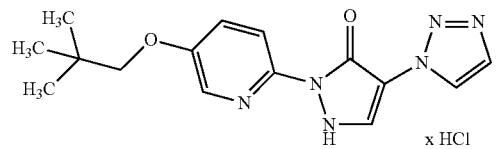 [SMILES: CC(C)(C)COc1ccc(-n2[nH]cc(-n3ccnn3)c2=O)nc1]

2 ml of a 4 N solution of hydrogen chloride in dioxane are added to 22 mg (0.1 mmol) of the compound from Example 84 and the mixture is stirred at RT for 1 h. The solid is filtered off and dried under a high vacuum.

Yield: 17 mg (97% of th.)

LC-MS (Method 10): $R_t$=1.17 min; MS (ESIpos): m/z=315 [M+H]$^+$;

$^1$H-NMR (500 MHz, DMSO-d$_6$): δ=8.42 (s, 1H), 8.29 (s, 1H), 8.23 (s, 1H), 8.18-8.08 (m, 1H), 7.90 (s, 1H), 7.69 (dd, 1H), 3.78 (s, 2H), 1.02 (s, 9H).

Example 86

1-[2-(6-Morpholin-4-ylpyrimidin-4-yl)-3-oxo-2,3-dihydro-1H-pyrazol-4-yl]-1H-1,2,3-triazole-4-carbonitrile trifluoroacetate

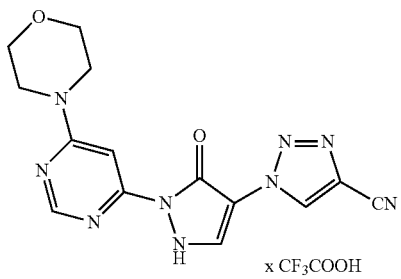 [SMILES: N#Cc1cn(-c2c[nH]n(-c3cc(N4CCOCC4)ncn3)c2=O)nn1]

250 mg (1.1 mmol) of the compound from Example 41A, 207 mg (1.1 mmol) of the compound from Example 16A and 40 mg (0.2 mmol) p-toluenesulfonic acid monohydrate are initially introduced into 10 ml THF. The mixture is reacted in a single mode microwave (CEM Explorer) first at 120° C. for 3.5 h and then at 130° C. for 4 h. The mixture is allowed to cool to RT, 5 ml acetonitrile are added and the mixture is left to stand for 24 h. The supernatant is decanted off and the precipitate is washed once with acetonitrile. The wash solution is combined with the supernatant decanted off and the mixture is concentrated. The residue obtained in this way is purified by means of preparative HPLC (RP18 column; mobile phase: acetonitrile/water gradient with addition of 0.1% TFA). The product-containing fractions are combined and concentrated. The solid residue is stirred twice in a mixture of a little tert-butyl methyl ether and a few drops of acetonitrile. The supernatant is decanted off each time and the solid is finally dried under a high vacuum.

Yield: 15 mg (3% of th.)

LC-MS (Method 4): $R_t$=1.57 min; MS (ESIpos): m/z=340 [M+H]$^+$;

$^1$H-NMR (400 MHz, DMSO-d$_6$): δ=8.58 (s, 1H), 8.24 (s, 1H), 7.42 (s, 1H), 3.80-3.63 (m, 8H).

Example 87

1-[2-(6-Morpholin-4-ylpyrimidin-4-yl)-3-oxo-2,3-dihydro-1H-pyrazol-4-yl]-1H-1,2,3-triazole-4-carbonitrile hydrochloride

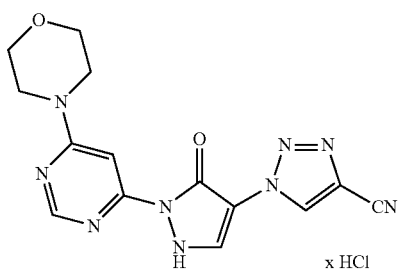 [SMILES: N#Cc1cn(-c2c[nH]n(-c3cc(N4CCOCC4)ncn3)c2=O)nn1]

3 ml of a 4 N solution of hydrogen chloride in dioxane are added to 18 mg (0.04 mmol) of the compound from Example 86 and the mixture is stirred at RT for 1 h. The solid is filtered off, washed with tert-butyl methyl ether and dried under a high vacuum.

Yield: 15 mg (97% of th.)

LC-MS (Method 8): $R_t$=1.38 min; MS (ESIpos): m/z=340 [M+H]$^+$;

$^1$H-NMR (400 MHz, DMSO-d$_6$): δ=8.58 (s, 1H), 8.25 (s, 1H), 7.41 (s, 1H), 3.82-3.57 (m, 8H).

Example 88

2-[6-(3-Hydroxyazetidin-1-yl)pyrimidin-4-yl]-4-(1H-1,2,3-triazol-1-yl)-1,2-dihydro-3H-pyrazol-3-one

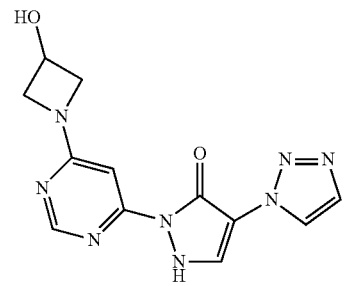 [SMILES: O=c1c(-n2ccnn2)c[nH]n1-c1cc(N2CC(O)C2)ncn1]

348 mg (1.7 mmol) of the compound from Example 3A and 300 mg (1.7 mmol) of the compound from Example 11A are initially introduced into a mixture of 6 ml THF and 6 ml ethanol. 63 mg (0.3 mmol) p-toluenesulfonic acid monohydrate are added and the mixture is reacted in a single mode microwave (CEM Explorer) at 130° C. for 1.5 h. The mixture is allowed to cool to RT, a further 50 mg of the compound from Example 3A and a spatula-tip of p-toluenesulfonic acid monohydrate are added and the mixture is heated at 150° C. for 1 h. It is allowed to cool to room temperature and is decanted off from the solid and the solid is washed several times with THF (solid batch 1). The supernatant decanted off and the wash solution are combined, the mixture is concentrated and 5 ml ethanol and 5 ml THF and a spatula-tip of p-toluenesulfonic acid monohydrate are added to the residue obtained. The mixture is reacted again in a single mode microwave (CEM Explorer) at 150° C. for 2 h. It is allowed to cool to RT and the solid formed is filtered off (solid batch 2). The filtrate is concentrated, 3 ml DMSO are added to the residue and purification is carried out by means of preparative HPLC (RP18 column; mobile phase: acetonitrile/water gradient with addition of 0.1% TFA). The product-containing fractions are combined and concentrated. The residue is dissolved in ethanol, a little THF is added and the mixture is concentrated, with formation of a precipitate. The solid is filtered off and washed with THF (solid batch 3). The three solid batches obtained are combined and the mixture is dried under a high vacuum.

Yield: 108 mg (22% of th.)

LC-MS (Method 8): $R_t$=1.00 min; MS (ESIpos): m/z=301 [M+H]$^+$;

$^1$H-NMR (400 MHz, DMSO-d$_6$): δ=8.47 (s, 1H), 8.36 (s, 1H), 8.18 (s, 1H), 7.84 (s, 1H), 6.97 (s, 1H), 5.92 (d, 1H), 4.69-4.49 (m, 1H), 4.41-4.33 (m, 2H), 3.95-3.86 (m, 2H).

Example 89

2-[6-(3-Hydroxyazetidin-1-yl)pyrimidin-4-yl]-4-(1H-1,2,3-triazol-1-yl)-1,2-dihydro-3H-pyrazol-3-one hydrochloride

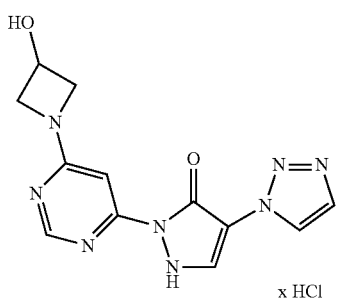 [SMILES: O=c1c(-n2ccnn2)c[nH]n1-c1cc(N2CC(O)C2)ncn1]

3 ml of a 4 N solution of hydrogen chloride in dioxane are added to 105 mg (0.4 mmol) of the compound from Example 88 and the mixture is stirred at RT for 1 h. The solid is filtered off, washed with tert-butyl methyl ether and dried under a high vacuum.

Yield: 117 mg (99% of th.)

LC-MS (Method 8): $R_t$=0.99 min; MS (ESIpos): m/z=301 [M+H]$^+$;

$^1$H-NMR (400 MHz, DMSO-d$_6$): δ=8.50 (s, 1H), 8.38 (s, 1H), 8.22 (s, 1H), 7.87 (s, 1H), 6.95 (s, 1H), 4.68-4.60 (m, 1H), 4.43-4.35 (m, 2H), 3.97-3.88 (m, 2H).

Example 90

2-(4,5-Dimethylpyridin-2-yl)-4-(1H-imidazol-1-yl)-1,2-dihydro-3H-pyrazol-3-one

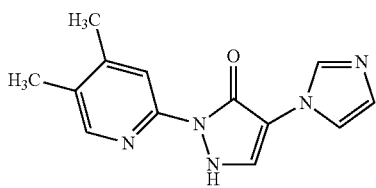 [SMILES: Cc1cnc(-n2[nH]cc(-n3ccnc3)c2=O)cc1C]

262 mg (1.3 mmol) of the compound from Example 42A and 172 mg (1.3 mmol) of the compound from Example 26A are initially introduced into 5 ml ethanol. 48 mg (0.3 mmol) p-toluenesulfonic acid monohydrate are added and the mixture is stirred under reflux for 24 h. The mixture is then cooled to RT, during which the product crystallizes out. The crystals are filtered off and rinsed in each case once with ethanol and petroleum ether. The product is subsequently dried under a high vacuum.

Yield: 65 mg (20% of th.)

LC-MS (Method 8): $R_t$=0.92 min; MS (ESIpos): m/z=256 [M+H]$^+$;

$^1$H-NMR (400 MHz, DMSO-d$_6$): δ=8.23 (s, 1H), 8.15 (s, 1H), 8.07 (s, 2H), 7.52 (s, 1H), 7.08 (s, 1H), 2.36 (s, 3H), 2.26 (s, 3H).

Example 91

2-(4,5-Dimethylpyridin-2-yl)-4-(1H-imidazol-1-yl)-1,2-dihydro-3H-pyrazol-3-one hydrochloride

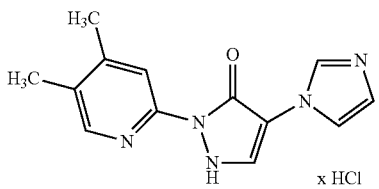 [SMILES: Cc1cnc(-n2[nH]cc(-n3ccnc3)c2=O)cc1C]

5 ml of a 4 N solution of hydrogen chloride in dioxane are added to 200 mg (0.5 mmol) of the compound from Example 90 and the mixture is stirred at RT for 1 h. The solid is then filtered off, washed in each case once with dioxane and tert-butyl methyl ether and dried under a high vacuum.

Yield: 117 mg (74% of th.)

LC-MS (Method 10): $R_t$=0.28 min; MS (ESIpos): m/z=256 [M+H]$^+$;

$^1$H-NMR (400 MHz, DMSO-d$_6$): δ=9.50 (s, 1H), 8.40 (s, 1H), 8.26 (s, 1H), 8.13 (s, 1H), 8.08 (s, 1H), 7.87 (s, 1H), 2.40 (s, 3H), 2.28 (s, 3H).

Example 92

2-[5-(2,2-Dimethylpropoxy)pyridin-2-yl]-4-(1H-imidazol-1-yl)-1,2-dihydro-3H-pyrazol-3-one

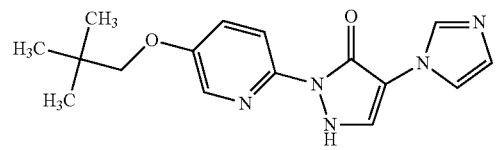 [SMILES: CC(C)(C)COc1ccc(-n2[nH]cc(-n3ccnc3)c2=O)nc1]

233 mg (1.0 mmol, purity 90%) of the compound from Example 42A are initially introduced into 4 ml ethanol. 260 mg (1.0 mmol, purity 75%) of the compound from Example 12A and 38 mg (0.2 mmol) p-toluenesulfonic acid monohydrate are added and the mixture is stirred under reflux for 16 h. The mixture is then allowed to cool to RT, the solid which has precipitated out is filtered off and washed with a little ethanol and the solid is dried under a high vacuum. A further amount of the target compound is obtained by purifying the mother liquor of the filtration via preparative HPLC (RP18 column; mobile phase: acetonitrile/water gradient with addition of 0.1% TFA).

Yield: 264 mg (78% of th.)

LC-MS (Method 10): $R_t$=0.88 min; MS (ESIpos): m/z=314 [M+H]$^+$;

$^1$H-NMR (400 MHz, DMSO-d$_6$): δ=8.22-8.08 (m, 4H), 7.67-7.62 (dd, 1H), 7.52 (s, 1H), 7.10 (s, 1H), 3.75 (s, 2H), 1.02 (s, 9H).

Example 93

2-[5-(2,2-Dimethylpropoxy)pyridin-2-yl]-4-(1H-imidazol-1-yl)-1,2-dihydro-3H-pyrazol-3-one hydrochloride

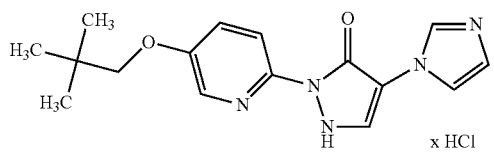 [SMILES: CC(C)(C)COc1ccc(-n2[nH]cc(-n3ccnc3)c2=O)nc1]

5 ml of a 4 N solution of hydrogen chloride in dioxane are added to 200 mg (0.638 mmol) of the compound from Example 92 and the mixture is stirred at RT for 30 min. The solid is subsequently filtered off, washed once with dioxane and twice with tert-butyl methyl ether and subsequently dried under a high vacuum.

Yield: 129 mg (64% of th.)

LC-MS (Method 10): $R_t$=0.87 min; MS (ESIpos): m/z=314 [M+H]$^+$;

$^1$H-NMR (400 MHz, DMSO-d$_6$): δ=9.52 (s, 1H), 8.46 (s, 1H), 8.22 (d, 1H), 8.18-8.15 (d, 1H), 8.07 (s, 1H), 7.87 (s, 1H), 7.71-7.68 (dd, 1H), 3.79 (s, 2H), 1.02 (s, 9H).

Example 94

2-(4,5-Dimethylpyridin-2-yl)-4-[4-(trifluoromethyl)-1H-imidazol-1-yl]-1,2-dihydro-3H-pyrazol-3-one trifluoroacetate

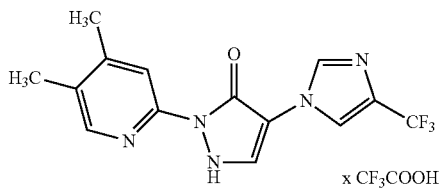 [SMILES: Cc1cnc(-n2[nH]cc(-n3cnc(C(F)(F)F)c3)c2=O)cc1C]

347 mg (1.3 mmol) of the compound from Example 44A and 171 mg (1.3 mmol) of the compound from Example 26A are initially introduced into 5 ml ethanol. 48 mg (0.3 mmol) p-toluenesulfonic acid monohydrate are added and the mixture is stirred under reflux for 16 h. The reaction solution is purified directly by means of preparative HPLC (RP18 column; mobile phase: acetonitrile/water gradient with addition of 0.1% TFA). The product-containing fractions are combined and partly concentrated. The solid is filtered off, washed with water and dried under a high vacuum.

Yield: 84 mg (15% of th.)

LC-MS (Method 8): $R_t$=1.88 min; MS (ESIpos): m/z=324 [M+H]$^+$;

$^1$H-NMR (400 MHz, DMSO-d$_6$): δ=8.27 (s, 1H), 8.25 (s, 1H), 8.18 (s, 1H), 8.15 (s, 1H), 8.08 (s, 1H), 2.38 (s, 3H), 2.27 (s, 3H).

Example 95

2-(4,5-Dimethylpyridin-2-yl)-4-[4-(trifluoromethyl)-1H-imidazol-1-yl]-1,2-dihydro-3H-pyrazol-3-one hydrochloride

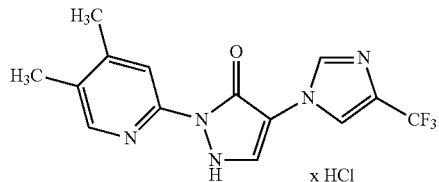 [SMILES: Cc1cnc(-n2[nH]cc(-n3cnc(C(F)(F)F)c3)c2=O)cc1C]

2.5 ml of a 4 N solution of hydrogen chloride in dioxane are added to 80 mg (0.2 mmol) of the compound from Example 94 and the mixture is stirred at RT for 1 h. The solid is filtered off, washed in each case once with dioxane and tert-butyl methyl ether and subsequently dried under a high vacuum.

Yield: 65 mg (99% of th.)

LC-MS (Method 10): $R_t$=1.03 min; MS (ESIpos): m/z=324 [M+H]$^+$;

$^1$H-NMR (400 MHz, DMSO-d$_6$): δ=8.27 (s, 1H), 8.25 (s, 1H), 8.18 (s, 1H), 8.13 (s, 1H), 8.07 (s, 1H), 2.37 (s, 3H), 2.27 (s, 3H).

Example 96

2-[5-(2,2-Dimethylpropoxy)pyridin-2-yl]-4-[4-(trifluoromethyl)-1H-imidazol-1-yl]-1,2-dihydro-3H-pyrazol-3-one hydrochloride

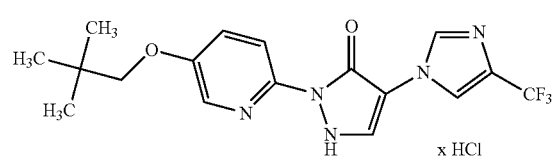 [SMILES: CC(C)(C)COc1ccc(-n2[nH]cc(-n3cnc(C(F)(F)F)c3)c2=O)nc1]

308 mg (1.0 mmol, purity 90%) of the compound from Example 44A are initially introduced into 4 ml ethanol. 260 mg (1.0 mmol, purity 75%) of the compound from Example 12A and 38 mg (0.2 mmol) p-toluenesulfonic acid monohydrate are added and the mixture is stirred under reflux for 16 h. Thereafter, it is concentrated and the residue is purified via preparative HPLC (RP18 column; mobile phase: acetonitrile/water gradient with addition of 0.1% TFA). The product-containing fractions are combined and the solvent is removed. 5 ml of a 4 N solution of hydrogen chloride in dioxane are added to the residue and the mixture is stirred for 30 min. The solid is filtered off and dried under a high vacuum.

Yield: 140 mg (34% of th.)

LC-MS (Method 10): $R_t$=1.38 min; MS (ESIpos): m/z=382 [M+H]$^+$;

$^1$H-NMR (400 MHz, DMSO-d$_6$): δ=8.29 (s, 1H), 8.21-8.12 (m, 4H), 7.71-7.68 (dd, 1H), 3.76 (s, 2H), 1.02 (s, 9H).

Example 97

2-[6-(Azetidin-3-yloxy)pyrimidin-4-yl]-4-(1H-1,2,3-triazol-1-yl)-1,2-dihydro-3H-pyrazol-3-one hydrochloride

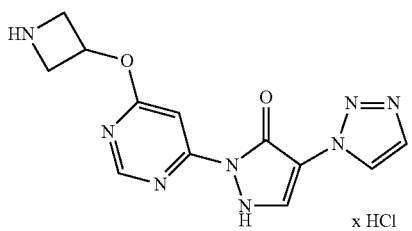 [SMILES: O=c1c(-n2ccnn2)c[nH]n1-c1cc(OC2CNC2)ncn1]

Stage a 3-({6-[5-Oxo-4-(1H-1,2,3-triazol-1-yl)-2,5-dihydro-1H-pyrazol-1-yl]pyrimidin-4-yl}oxy)azetidine 1-tert-butyl ester trifluoroacetate

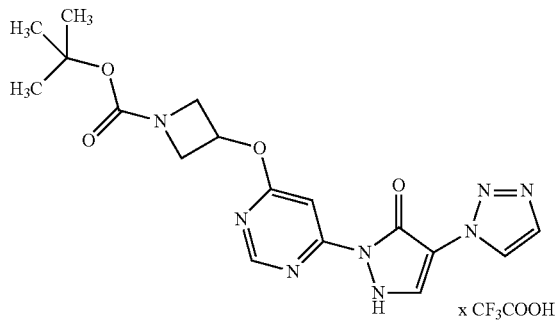 [SMILES: CC(C)(C)OC(=O)N1CC(Oc2cc(-n3[nH]cc(-n4ccnn4)c3=O)ncn2)C1]

345 mg (2.0 mmol) 3-hydroxyazetidine 1-tert-butyl ester are initially introduced into 15 ml dioxane. 1 ml (2.0 mmol) of a 2 M solution of the phosphazene base P2-tert-butyl in THF is added at RT. The mixture is subsequently stirred at RT for 15 min and 350 mg (1.3 mmol) of the compound from Example 52A are added. The mixture is then reacted in a single mode microwave (CEM Explorer) at 120° C. for 1 h. The solid is separated off by filtration, the reaction solution is concentrated and the residue is subsequently purified by means of preparative HPLC (RP18 column; mobile phase: acetonitrile/water gradient with addition of 0.1% TFA). The product-containing fractions are combined and partly concentrated. The solid is filtered off, washed with water and dried under a high vacuum.

Yield: 82 mg (12% of th.)

LC-MS (Method 10): R$_t$=0.98 min; MS (ESIpos): m/z=401 [M+H]$^+$;

$^1$H-NMR (400 MHz, DMSO-d$_6$): δ=8.77 (s, 1H), 8.61 (s, 1H), 8.43 (s, 1H), 7.90 (s, 1H), 7.78 (s, 1H), 5.47-5.38 (m, 1H), 4.32-4.22 (m, 2H), 3.96-3.86 (m, 2H), 1.40 (s, 9H).

Stage b

2-[6-(Azetidin-3-yloxy)pyrimidin-4-yl]-4-(1H-1,2,3-triazol-1-yl)-1,2-dihydro-3H-pyrazol-3-one hydrochloride

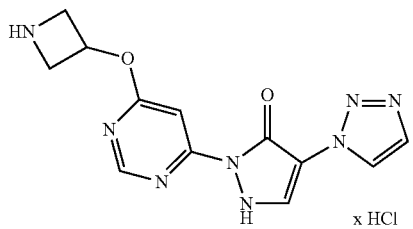 [SMILES: O=c1c(-n2ccnn2)c[nH]n1-c1cc(OC2CNC2)ncn1]

60 mg (0.2 mmol) 3-({6-[5-Oxo-4-(1H-1,2,3-triazol-1-yl)-2,5-dihydro-1H-pyrazol-1-yl]pyrimidin-4-yl}oxy)azetidine 1-tert-butyl ester are suspended in 2 ml methylene chloride. 1 ml TFA is added and the mixture is stirred at RT for 1 h. Thereafter, the mixture is concentrated and the residue is dried under a high vacuum. 3 ml of a 4 N solution of hydrogen chloride in dioxane are then added to the residue and the mixture is stirred at RT for 1 h. The solid is then filtered off, washed in each case once with dioxane and tert-butyl methyl ether and dried under a high vacuum.

Yield: 54 mg (97% of th.)

LC-MS (Method 8): R$_t$=0.80 min; MS (ESIpos): m/z=301 [M+H]$^+$;

$^1$H-NMR (400 MHz, DMSO-d$_6$): δ=9.50 (br. s, 1H), 9.37 (br. s, 1H), 8.80 (s, 1H), 8.63 (s, 1H), 8.44 (s, 1H), 7.90 (s, 1H), 7.80 (s, 1H), 5.57-5.48 (m, 1H), 4.43-4.32 (m, 2H), 4.18-4.07 (m, 2H).

Example 98

1-{2-[5-(2,2-Dimethylpropoxy)pyridin-2-yl]-3-oxo-2,3-dihydro-1H-pyrazol-4-yl}-1H-1,2,3-triazole-4-carbonitrile hydrochloride

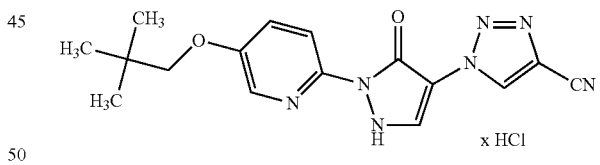

150 mg (0.6 mmol) of the compound from Example 41A are initially introduced into 2.5 ml ethanol. 166 mg (0.6 mmol, purity 75%) of the compound from Example 12A and 24 mg (0.1 mmol) p-toluenesulfonic acid monohydrate are added and the mixture is stirred under reflux for 16 h. The reaction solution is purified directly by means of preparative HPLC (RP18 column; mobile phase: acetonitrile/water gradient with addition of 0.1% TFA). The product-containing fractions are combined and concentrated. 1 ml of a 4 N solution of hydrogen chloride in dioxane are added to the residue obtained and the mixture is stirred at RT for 1 h. The mixture is concentrated and the residue is dried under a high vacuum.

Yield: 3 mg (1% of th.)

LC-MS (Method 8): R$_t$=2.42 min; MS (ESIpos): m/z=340 [M+H]$^+$;

¹H-NMR (400 MHz, DMSO-d₆): δ=9.39 (s, 1H), 8.41 (s, 1H), 8.24 (d, 1H), 8.12 (d, 1H), 7.70 (dd, 1H), 3.78 (s, 2H), 1.03 (s, 9H).

Example 99

6-[4-(4-Cyano-1H-1,2,3-triazol-1-yl)-5-oxo-2,5-dihydro-1H-pyrazol-1-yl]pyridine 3-tert-butyl ester hydrochloride

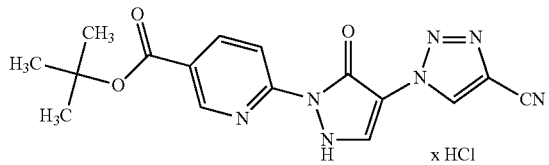 [SMILES: CC(C)(C)OC(=O)c1ccc(-n2[nH]cc(-n3cc(C#N)nn3)c2=O)nc1]

150 mg (0.6 mmol) of the compound from Example 41A are initially introduced into 2.5 ml ethanol. 178 mg (0.6 mmol) of the compound from Example 22A and 24 mg (0.1 mmol) p-toluenesulfonic acid monohydrate are added and the mixture is stirred under reflux for 16 h. The reaction solution is purified directly by means of preparative HPLC (RP18 column; mobile phase: acetonitrile/water gradient with addition of 0.1% TFA). The product-containing fractions are combined, the mixture is concentrated and the residue is dried under a high vacuum. 5 ml of a 4 N solution of hydrogen chloride in dioxane are added to the residue obtained and the mixture is stirred at RT for 30 min. The solid is filtered off, washed with tert-butyl methyl ether and dried under a high vacuum.

Yield: 21 mg (8% of th.)

LC-MS (Method 7): R$_t$=1.96 min; MS (ESIpos): m/z=354 [M+H]$^+$;

¹H-NMR (400 MHz, DMSO-d₆): δ=9.39 (s, 1H), 8.94 (s, 1H), 8.63 (s, 1H), 8.46 (s, 2H), 1.58 (s, 9H).

Example 100

2-[6-(3-Hydroxyazetidin-1-yl)pyrimidin-4-yl]-4-(1H-imidazol-1-yl)-1,2-dihydro-3H-pyrazol-3-one trifluoroacetate

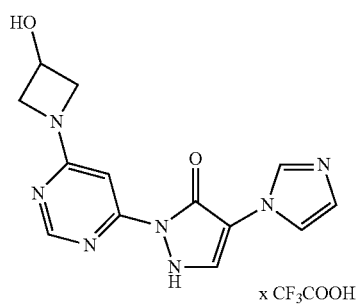 [SMILES: O=c1c(-n2ccnc2)c[nH]n1-c1cc(N2CC(O)C2)ncn1]

400 mg (1.3 mmol) of the compound from Example 53A, 518 mg (4.0 mmol) N,N-diisopropylamine and 293 mg (2.6 mmol) azetidin-3-ol hydrochloride are suspended in 8 ml ethanol. The mixture is reacted in a single mode microwave (CEM Explorer) at 120° C. for 30 min. After filtration, the reaction solution is purified via preparative HPLC (RP18 column; mobile phase: acetonitrile/water gradient with addition of 0.1% TFA). The product-containing fractions are concentrated and the residue is stirred in a mixture of 5 ml tert-butyl methyl ether and 10 ml methanol and then filtered off with suction. Thereafter, it is purified again by means of preparative HPLC (RP18 column; mobile phase: acetonitrile/water gradient with addition of 0.1% TFA). The product-containing fractions are combined, the mixture is concentrated and the residue is dried under a high vacuum.

Yield: 115 mg (21% of th.)

LC-MS (Method 8): R$_t$=0.80 min; MS (ESIpos): m/z=300 [M+H]$^+$;

¹H-NMR (400 MHz, DMSO-d₆): δ=9.38 (s, 1H), 8.50 (s, 1H), 8.23 (s, 1H), 8.02 (t, 1H), 7.80 (t, 1H), 6.97 (s, 1H), 4.70-4.61 (m, 1H), 4.47-4.38 (m, 2H), 3.98-3.90 (m, 2H).

Example 101

2-[6-(3-Hydroxyazetidin-1-yl)pyrimidin-4-yl]-4-(1H-imidazol-1-yl)-1,2-dihydro-3H-pyrazol-3-one hydrochloride

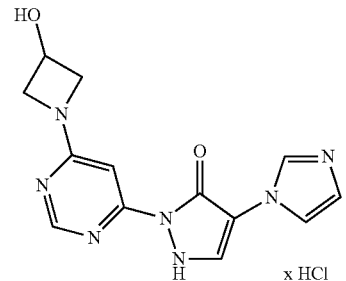 [SMILES: O=c1c(-n2ccnc2)c[nH]n1-c1cc(N2CC(O)C2)ncn1]

100 mg (0.2 mmol) of the compound from Example 100 are stirred with 3 ml of a 4 N solution of hydrogen chloride in dioxane The solid is filtered off, washed twice with tert-butyl methyl ether and dried under a high vacuum.

Yield: 78 mg (96% of th.)

LC-MS (Method 8): R$_t$=0.80 min; MS (ESIpos): m/z=300 [M+H]$^+$;

¹H-NMR (400 MHz, DMSO-d₆): δ=9.42 (s, 1H), 8.50 (s, 1H), 8.25 (s, 1H), 8.03 (t, 1H), 7.82 (t, 1H), 6.97 (s, 1H), 4.69-4.60 (m, 1H), 4.47-4.37 (m, 2H), 3.99-3.90 (m, 2H).

Example 102

2-[6-(Ethylsulfanyl)pyrimidin-4-yl]-4-(1H-1,2,3-triazol-1-yl)-1,2-dihydro-3H-pyrazol-3-one

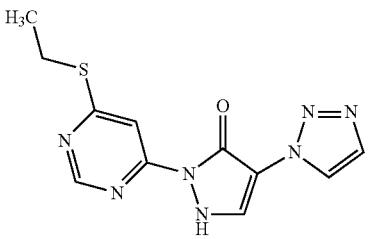 [SMILES: CCSc1cc(-n2[nH]cc(-n3ccnn3)c2=O)ncn1]

200 mg (0.7 mmol) of the compound from Example 52A are suspended in 1.1 ml DMF under argon. 61 mg (1.0 mmol) ethanethiol are added. 35 mg (0.8 mmol, 60% strength in mineral oil) sodium hydride are added cautiously, while cooling with ice. The mixture is stirred at RT for 2.5 h. 1 ml water is subsequently added dropwise and the mixture is subsequently stirred at RT for 15 min. The clear reaction solution obtained is purified directly by means of preparative HPLC (RP18 column; mobile phase: acetonitrile/water gradient with addition of 0.1% TFA). The product-containing fractions are combined, the mixture is concentrated and the residue is dried under a high vacuum.

Yield: 39 mg (18% of th.)

LC-MS (Method 10): $R_t$=0.81 min; MS (ESIpos): m/z=290 [M+H]$^+$;

$^1$H-NMR (400 MHz, DMSO-d$_6$): δ=8.90 (s, 1H), 8.60 (s, 1H), 8.44 (s, 1H), 8.27 (s, 1H), 7.90 (s, 1H), 3.20 (q, 2H), 1.35 (t, 3H).

Example 103

2-[6-(Ethylsulfanyl)pyrimidin-4-yl]-4-(1H-1,2,3-triazol-1-yl)-1,2-dihydro-3H-pyrazol-3-one hydrochloride

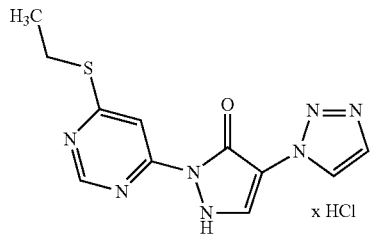 [SMILES: CCSc1cc(-n2[nH]cc(-n3ccnn3)c2=O)ncn1]

35 mg (0.1 mmol) of the compound from Example 102 are stirred with 1.5 ml of a 4 N solution of hydrogen chloride in dioxane. The solid is filtered off, washed twice with tert-butyl methyl ether and dried under a high vacuum.

Yield: 36 mg (90% of th.)

LC-MS (Method 10): $R_t$=0.80 min; MS (ESIpos): m/z=290 [M+H]$^+$;

$^1$H-NMR (400 MHz, DMSO-d$_6$): δ=8.90 (s, 1H), 8.62 (s, 1H), 8.44 (s, 1H), 8.26 (s, 1H), 7.91 (s, 1H), 3.21 (q, 2H), 1.35 (t, 3H).

Example 104

2-(6-{[2-(Diethylamino)ethyl]sulfanyl}pyrimidin-4-yl)-4-(1H-1,2,3-triazol-1-yl)-1,2-dihydro-3H-pyrazol-3-one trifluoroacetate

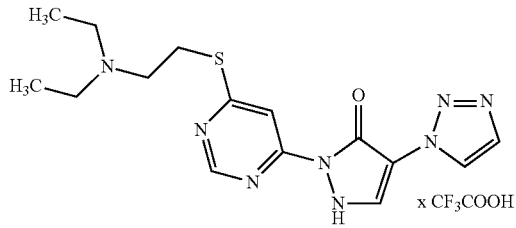 [SMILES: CCN(CC)CCSc1cc(-n2[nH]cc(-n3ccnn3)c2=O)ncn1]

200 mg (0.7 mmol) of the compound from Example 52A are dissolved in 2 ml DMF under argon. 131 mg (1.0 mmol) 2-(diethylamino)ethanethiol are added dropwise and the mixture is then cooled to 0° C. 35 mg (0.8 mmol, 60% strength in mineral oil) sodium hydride are added and the mixture is allowed to warm to RT and is stirred at RT for 2.5 h. 3 ml water are subsequently added slowly and the mixture is stirred for 15 min. The precipitate is filtered off and the filtrate is concentrated. The residue obtained in this way is purified via preparative HPLC (RP18 column; mobile phase: acetonitrile/water gradient with addition of 0.1% TFA).

Yield: 129 mg (41% of th.)

LC-MS (Method 10): $R_t$=0.29 min; MS (ESIpos): m/z=361 [M+H]$^+$;

$^1$H-NMR (400 MHz, DMSO-d$_6$): δ=9.42 (br. s, 1H), 8.91 (s, 1H), 8.49 (s, 1H), 8.40 (s, 1H), 8.37 (s, 1H), 7.88 (s, 1H), 3.58-3.51 (m, 2H), 3.42-3.33 (m, 2H), 3.28-3.20 (m, 4H), 1.30-1.20 (m, 6H).

Example 105

2-{6-[4-(2-Methoxyethyl)piperazin-1-yl]pyrimidin-4-yl}-4-(1H-,2,3-triazol-1-yl)-1,2-dihydro-3H-pyrazol-3-one hydrochloride

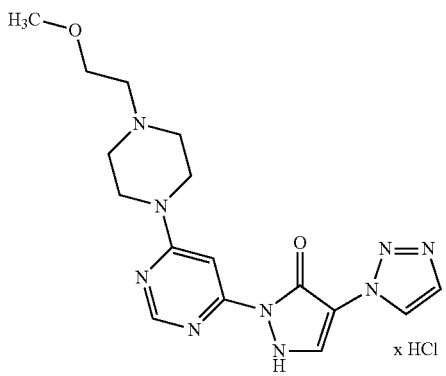 [SMILES: COCCN1CCN(c2cc(-n3[nH]cc(-n4ccnn4)c3=O)ncn2)CC1]

500 mg (2.4 mmol) of the compound from Example 3A, 600 mg (2.4 mmol) of the compound from Example 31A and 82 mg (0.5 mmol) p-toluenesulfonic acid are initially introduced into 8 ml THF and the mixture is reacted in a single mode microwave (Emrys Optimizer) at 170° C. for 30 min. After cooling to RT, the residue is purified directly by means of preparative HPLC (RP18 column; mobile phase: acetonitrile/water gradient with addition of 0.1% formic acid in the water). The formate salt thereby obtained is converted into the hydrochloride by addition of 4 ml of a 4 N solution of hydrogen chloride in dioxane. The product is washed with diethyl ether and dried in vacuo.

Yield: 212 mg (20% of th.)

LC-MS (Method 11): $R_t$=2.79 min; MS (ESIpos): m/z=372 [M+H]$^+$;

$^1$H-NMR (400 MHz, DMSO-d$_6$): δ=11.28 (br. s, 1H), 8.61 (s, 1H), 8.41 (s, 1H), 8.38 (s, 1H), 7.90 (s, 1H), 7.56 (s, 1H), 4.64-4.43 (m, 2H), 3.76 (t, 2H), 3.65-3.51 (m, 4H), 3.36-3.30 (m, 5H), 3.23-3.08 (m, 2H).

Example 106

2-[6-(3,5-Dimethylpiperidin-1-yl)pyrimidin-4-yl]-4-(1H-1,2,3-triazol-1-yl)-1,2-dihydro-3H-pyrazol-3-one

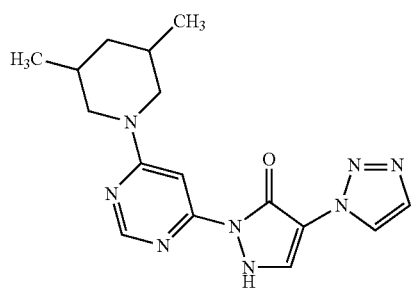 [SMILES: CC1CC(C)CN(c2cc(-n3[nH]cc(-n4ccnn4)c3=O)ncn2)C1]

2.9 g (9.6 mmol) Example Compound 52A are dissolved in 40 ml DMF and provided as a stock solution.

23 mg (0.1 mmol) 3,5-dimethylpiperidine are initially introduced into 200 µl DMF, and 400 µl (0.1 mmol) of the stock solution from Example Compound 52A and 35 mg (0.3 mmol) potassium carbonate are added in succession. The reaction mixture is stirred at 100° C. for 16 h. For working up, the suspension is filtered and the filtrate is chromatographed by means of preparative LC-MS (Method 16). The product fractions are concentrated in vacuo and the residue is dried.

Yield: 3 mg (10% of th.)

LC-MS (Method 16): $R_t$=1.90 min; MS (ESIpos): m/z=341 [M+H]$^+$.

The compounds listed in Table 8 are prepared analogously to the working instructions of Example 106 from 0.1 mmol Example Compound 52A and 0.1 mmol of the corresponding secondary amine:

TABLE 8

| Example no. | Structure | Yield (% of th.) | MS (ESI) [M + H]$^+$; LC-MS: $R_t$ (Method 16) |
|---|---|---|---|
| 107 | 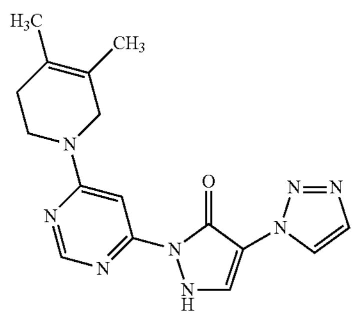 [SMILES: CC1=C(C)CN(c2cc(-n3[nH]cc(-n4ccnn4)c3=O)ncn2)CC1] | 2% | m/z = 339; 1.88 min |
| 108 | 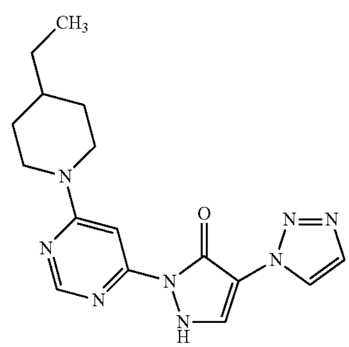 [SMILES: CCC1CCN(c2cc(-n3[nH]cc(-n4ccnn4)c3=O)ncn2)CC1] | 1% | m/z = 341; 1.91 min |
| 109 | 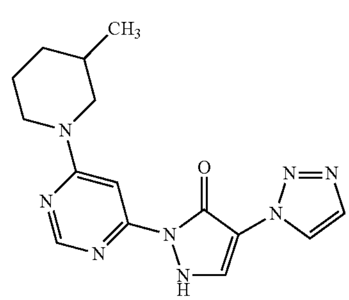 [SMILES: CC1CCCN(c2cc(-n3[nH]cc(-n4ccnn4)c3=O)ncn2)C1] | 7% | m/z = 327; 1.77 min |

TABLE 8-continued

| Example no. | Structure | Yield (% of th.) | MS (ESI) [M + H]+; LC-MS: R_t (Method 16) |
|---|---|---|---|
| 110 | 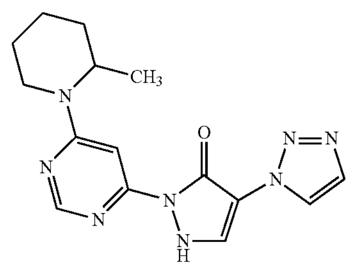 [SMILES: CC1CCCCN1c1cc(-n2[nH]cc(-n3ccnn3)c2=O)ncn1] | 5% | m/z = 327; 1.77 min |
| 111 | 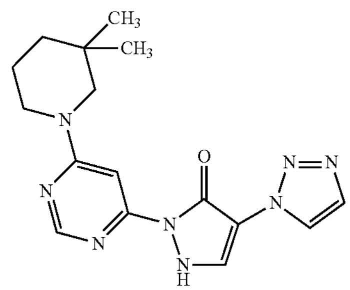 [SMILES: CC1(C)CCCN(c2cc(-n3[nH]cc(-n4ccnn4)c3=O)ncn2)C1] | 4% | m/z = 341; 1.82 min |
| 112 | 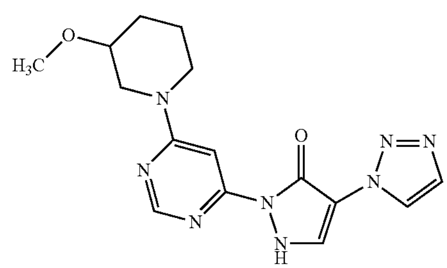 [SMILES: COC1CCCN(c2cc(-n3[nH]cc(-n4ccnn4)c3=O)ncn2)C1] | 5% | m/z = 343; 1.54 min |
| 113 | 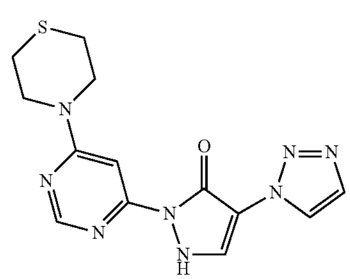 [SMILES: O=c1c(-n2ccnn2)c[nH]n1-c1cc(N2CCSCC2)ncn1] | 5% | m/z = 331; 1.58 min |
| 114 | 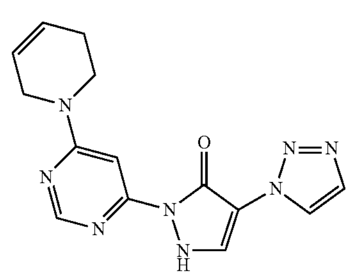 [SMILES: O=c1c(-n2ccnn2)c[nH]n1-c1cc(N2CC=CCC2)ncn1] | 5% | m/z = 311; 1.63 min |

TABLE 8-continued

| Example no. | Structure | Yield (% of th.) | MS (ESI) [M + H]+; LC-MS: R_t (Method 16) |
|---|---|---|---|
| 115 | 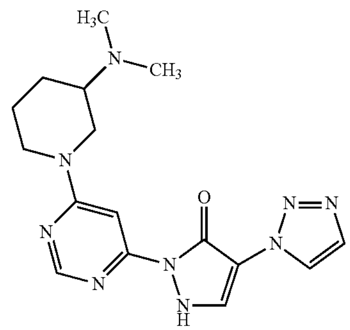 [SMILES: CN(C)C1CCCN(c2cc(-n3[nH]cc(-n4ccnn4)c3=O)ncn2)C1] | 2% | m/z = 356; 1.18 min |
| 116 | 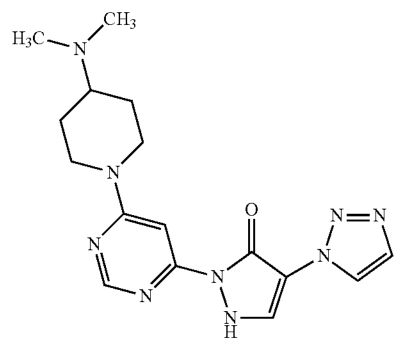 [SMILES: CN(C)C1CCN(c2cc(-n3[nH]cc(-n4ccnn4)c3=O)ncn2)CC1] | 7% | m/z = 356; 1.18 min |
| 117 | 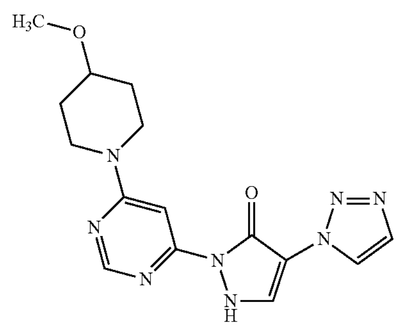 [SMILES: COC1CCN(c2cc(-n3[nH]cc(-n4ccnn4)c3=O)ncn2)CC1] | 6% | m/z = 343; 1.53 min |
| 118 | 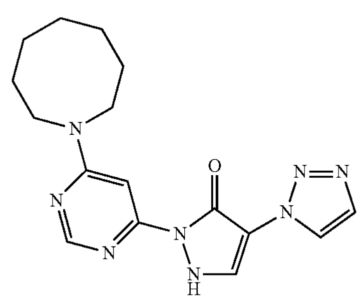 [SMILES: O=c1c(-n2ccnn2)c[nH]n1-c1cc(N2CCCCCCC2)ncn1] | 7% | m/z = 341; 1.82 min |

TABLE 8-continued

| Example no. | Structure | Yield (% of th.) | MS (ESI) [M + H]+; LC-MS: R$_t$ (Method 16) |
|---|---|---|---|
| 119 | 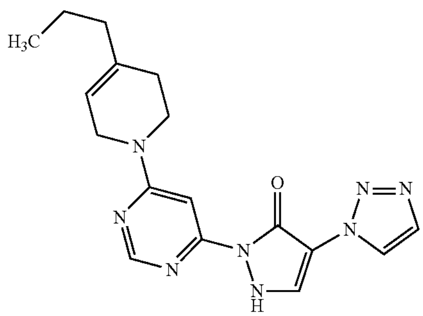 [SMILES: CCCC1=CCN(c2cc(-n3[nH]cc(-n4ccnn4)c3=O)ncn2)CC1] | 9% | m/z = 353; 2.01 min |
| 120 | 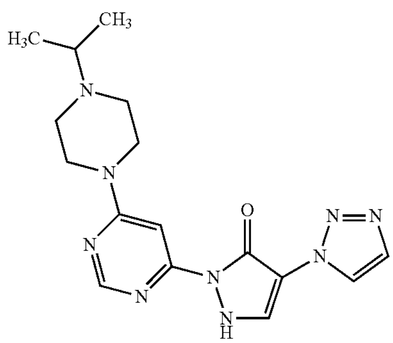 | 9% | m/z = 356; 1.18 min |
| 121 | 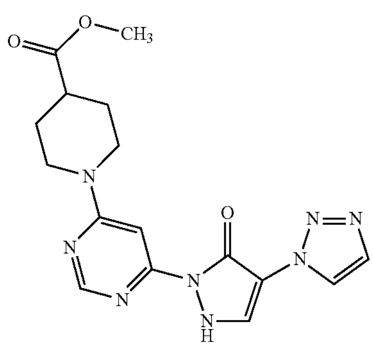 [SMILES: COC(=O)C1CCN(c2cc(-n3[nH]cc(-n4ccnn4)c3=O)ncn2)CC1] | 8% | m/z = 371; 1.60 min |
| 122 | 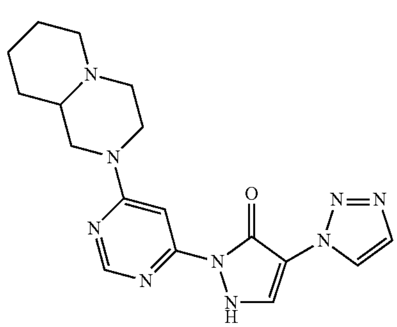 [SMILES: O=c1c(-n2ccnn2)c[nH]n1-c1cc(N2CCN3CCCCC3C2)ncn1] | 9% | m/z = 368; 1.18 min |

TABLE 8-continued

| Example no. | Structure | Yield (% of th.) | MS (ESI) [M + H]+; LC-MS: R$_t$ (Method 16) |
|---|---|---|---|
| 123 | 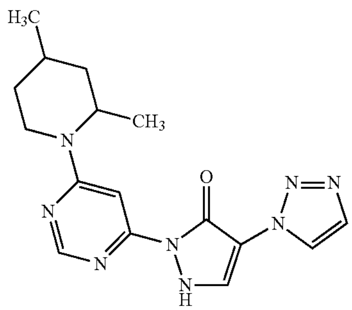 [SMILES: CC1CCN(c2cc(-n3[nH]cc(-n4ccnn4)c3=O)ncn2)C(C)C1] | 2% | m/z = 341; 1.81 min |
| 124 | 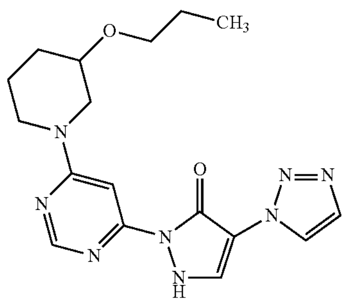 [SMILES: CCCOC1CCCN(c2cc(-n3[nH]cc(-n4ccnn4)c3=O)ncn2)C1] | 10% | m/z = 371; 1.79 min |
| 125 | 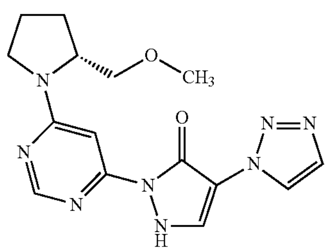 [SMILES: COC[C@H]1CCCN1c1cc(-n2[nH]cc(-n3ccnn3)c2=O)ncn1] | 7% | m/z = 343; 1.57 min |
| 126 | 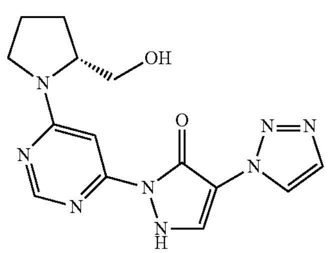 [SMILES: O=c1c(-n2ccnn2)c[nH]n1-c1cc(N2CCC[C@@H]2CO)ncn1] | 2% | m/z = 329; 1.39 min |
| 127 | 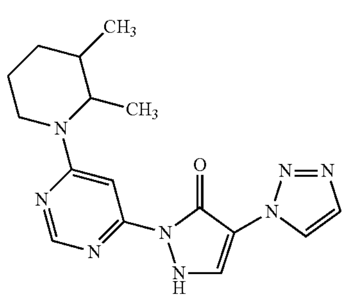 [SMILES: CC1CCCN(c2cc(-n3[nH]cc(-n4ccnn4)c3=O)ncn2)C1C] | 3% | m/z = 341; 1.88 min |

TABLE 8-continued

| Example no. | Structure | Yield (% of th.) | MS (ESI) [M + H]+; LC-MS: R_t (Method 16) |
|---|---|---|---|
| 128 | 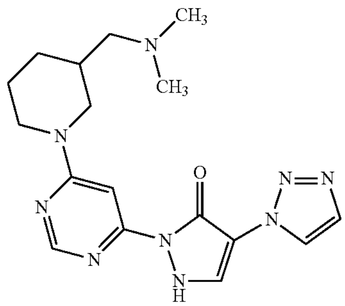 [SMILES: CN(C)CC1CCCN(c2cc(-n3[nH]cc(-n4ccnn4)c3=O)ncn2)C1] | 4% | m/z = 370; 1.22 min |
| 129 | 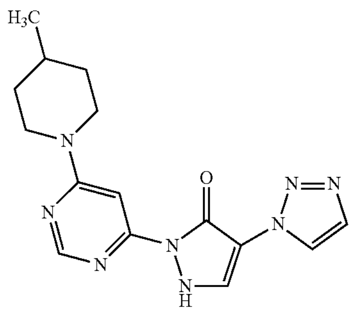 [SMILES: CC1CCN(c2cc(-n3[nH]cc(-n4ccnn4)c3=O)ncn2)CC1] | 7% | m/z = 327; 1.78 min |
| 130 | 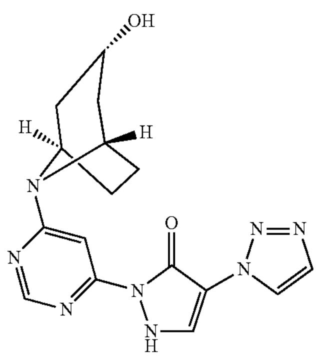 | 10% | m/z = 371; 1.79 min |
| 131 | 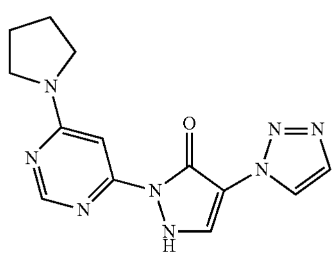 [SMILES: O=c1c(-n2ccnn2)c[nH]n1-c1cc(N2CCCC2)ncn1] | 3% | m/z = 299; 1.51 min |
| 132 | 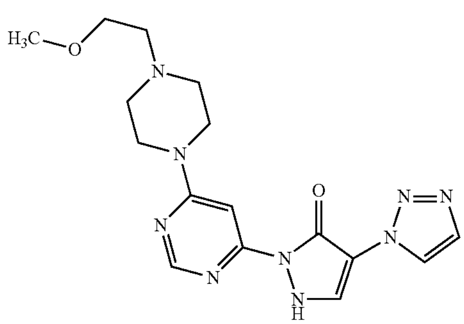 [SMILES: COCCN1CCN(c2cc(-n3[nH]cc(-n4ccnn4)c3=O)ncn2)CC1] | 3% | m/z = 372; 1.15 min |

TABLE 8-continued

| Example no. | Structure | Yield (% of th.) | MS (ESI) [M + H]⁺; LC-MS: R_t (Method 16) |
|---|---|---|---|
| 133 | 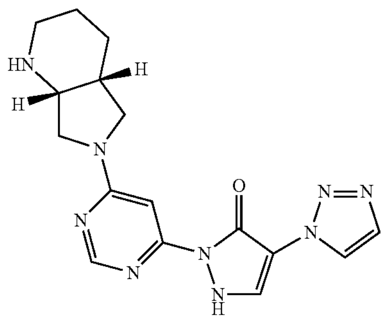 [SMILES: O=c1c(-n2ccnn2)c[nH]n1-c1cc(N2C[C@H]3CCCN[C@H]3C2)ncn1] | 9% | m/z = 354; 1.18 min |
| 134 | 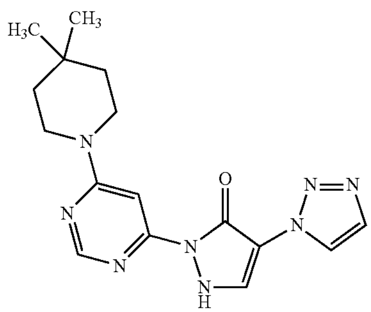 [SMILES: CC1(C)CCN(c2cc(-n3[nH]cc(-n4ccnn4)c3=O)ncn2)CC1] | 11% | m/z = 341; 1.87 min |
| 135 | 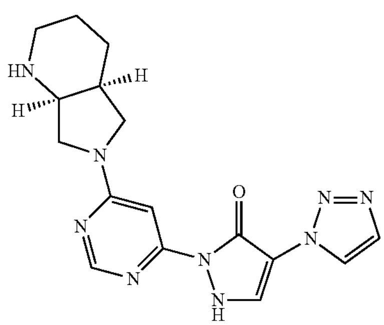 [SMILES: O=c1c(-n2ccnn2)c[nH]n1-c1cc(N2C[C@@H]3CCCN[C@@H]3C2)ncn1] | 5% | m/z = 354; 1.18 min |
| 136 | 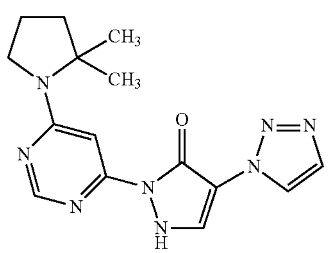 [SMILES: CC1(C)CCCN1c1cc(-n2[nH]cc(-n3ccnn3)c2=O)ncn1] | 2% | m/z = 327; 1.79 min |
| 137 | 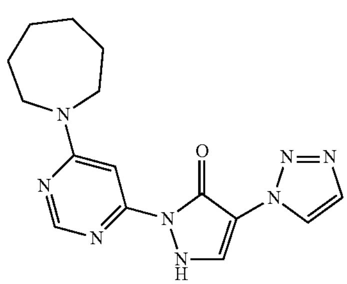 [SMILES: O=c1c(-n2ccnn2)c[nH]n1-c1cc(N2CCCCCC2)ncn1] | 6% | m/z = 327; 1.73 min |

Example 138

2-[6-(2,5-Dimethyl-2,5-dihydro-1H-pyrrol-1-yl)pyrimidin-4-yl]-4-(1H-imidazol-1-yl)-1,2-dihydro-3H-pyrazol-3-one

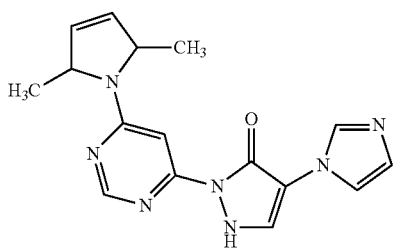 [SMILES: CC1C=CC(C)N1c1cc(-n2[nH]cc(-n3ccnc3)c2=O)ncn1]

2.9 g (9.6 mmol) Example Compound 53A are dissolved in 40 ml DMF and provided as a stock solution.

19 mg (0.1 mmol) 2,5-dimethyl-2,5-dihydro-1H-pyrrole are initially introduced into 200 µl DMF, and 400 µl (0.1 mmol) of the stock solution from Example Compound 53A and 35 mg (0.3 mmol) potassium carbonate are added in succession. The reaction mixture is stirred at 100° C. for 16 h. For working up, the suspension is filtered and the filtrate is chromatographed by means of preparative LC-MS (Method 16). The product fractions are concentrated in vacuo and the residue is dried.

Yield: 5 mg (16% of th.)

LC-MS (Method 16): $R_t$=1.42 min; MS (ESIpos): m/z=324 [M+H]$^+$.

The compounds listed in Table 9 are prepared analogously to the working instructions of Example 140 from 0.1 mmol Example Compound 53A and 0.1 mmol of the corresponding secondary amine:

TABLE 9

| Example no. | Structure | Yield (% of th.) | MS (ESI) [M + H]$^+$; LC-MS: $R_t$ (Method 16) |
|---|---|---|---|
| 139 | 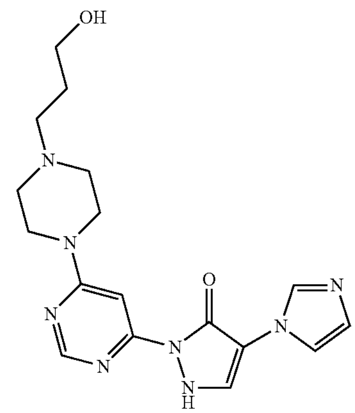 [SMILES: O=c1c(-n2ccnc2)c[nH]n1-c1cc(N2CCN(CCCO)CC2)ncn1] | 34% | m/z = 371; 0.30 min |
| 140 | 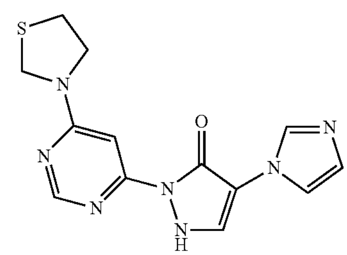 [SMILES: O=c1c(-n2ccnc2)c[nH]n1-c1cc(N2CCSC2)ncn1] | 16% | m/z = 351; 1.28 min |
| 141 | 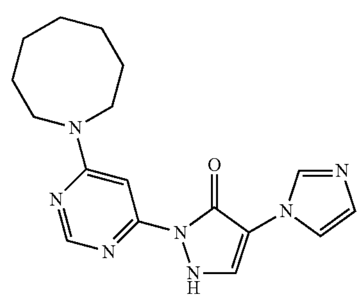 [SMILES: O=c1c(-n2ccnc2)c[nH]n1-c1cc(N2CCCCCCC2)ncn1] | 69% | m/z = 340; 1.48 min |

TABLE 9-continued

| Example no. | Structure | Yield (% of th.) | MS (ESI) [M + H]+; LC-MS: R_t (Method 16) |
|---|---|---|---|
| 142 | 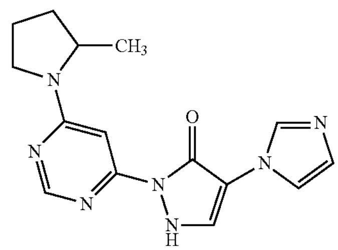 [SMILES: CC1CCCN1c1cc(-n2[nH]cc(-n3ccnc3)c2=O)ncn1] | 10% | m/z = 312; 1.34 min |
| 143 | 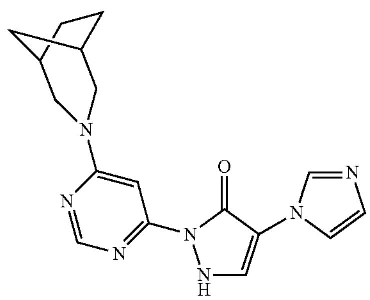 [SMILES: O=c1c(-n2ccnc2)c[nH]n1-c1cc(N2CC3CCC(C3)C2)ncn1] | 52% | m/z = 338; 1.45 min |
| 144 | 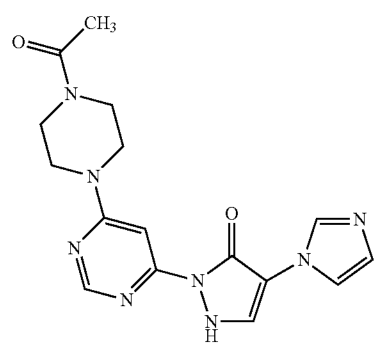 [SMILES: CC(=O)N1CCN(c2cc(-n3[nH]cc(-n4ccnc4)c3=O)ncn2)CC1] | 4% | m/z = 355; 1.22 min |
| 145 | 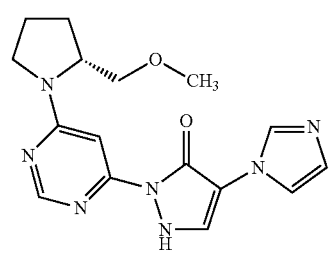 [SMILES: COC[C@H]1CCCN1c1cc(-n2[nH]cc(-n3ccnc3)c2=O)ncn1] | 83% | m/z = 342; 1.32 min |
| 146 | 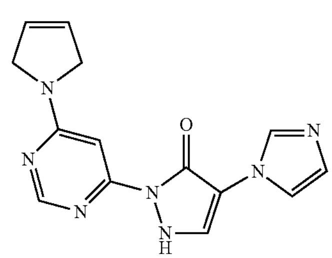 [SMILES: O=c1c(-n2ccnc2)c[nH]n1-c1cc(N2CC=CC2)ncn1] | 13% | m/z = 295; 1.27 min |

TABLE 9-continued

| Example no. | Structure | Yield (% of th.) | MS (ESI) [M + H]+; LC-MS: R_t (Method 16) |
|---|---|---|---|
| 147 | 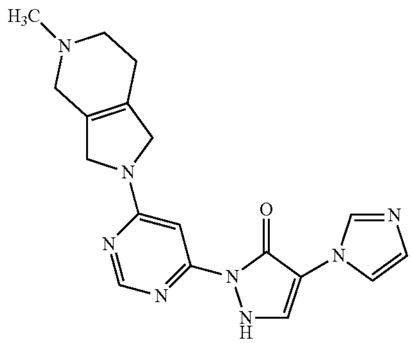 [SMILES: CN1CCC2=C(C1)CN(c1cc(-n3[nH]cc(-n4ccnc4)c3=O)ncn1)C2] | 44% | m/z = 365; 1.07 min |
| 148 | 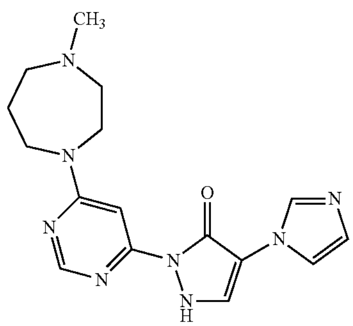 [SMILES: CN1CCCN(c2cc(-n3[nH]cc(-n4ccnc4)c3=O)ncn2)CC1] | 42% | m/z = 341; 0.30 min |
| 149 | 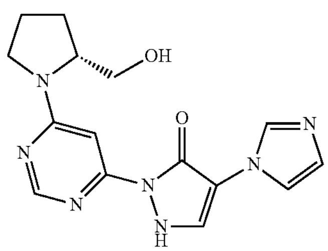 [SMILES: O=c1c(-n2ccnc2)c[nH]n1-c1cc(N2CCC[C@@H]2CO)ncn1] | 32% | m/z = 328; 1.21 min |
| 150 | 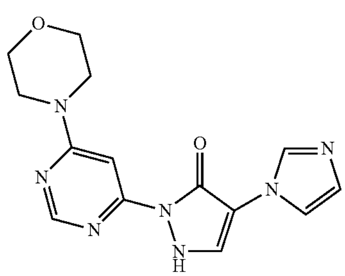 | 17% | m/z = 314; 1.21 min |
| 151 | 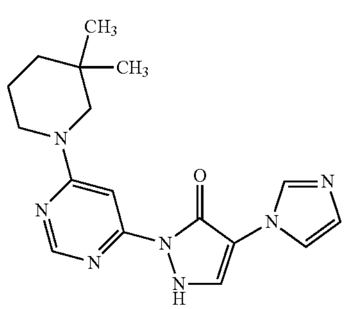 [SMILES: CC1(C)CCCN(c2cc(-n3[nH]cc(-n4ccnc4)c3=O)ncn2)C1] | 33% | m/z = 340; 1.51 min |

TABLE 9-continued

| Example no. | Structure | Yield (% of th.) | MS (ESI) [M + H]+; LC-MS: R_t (Method 16) |
|---|---|---|---|
| 152 | 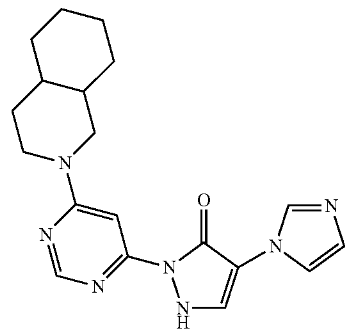 [SMILES: O=c1c(-n2ccnc2)c[nH]n1-c1cc(N2CCC3CCCCC3C2)ncn1] | 98% | m/z = 365; 1.63 min |
| 153 | 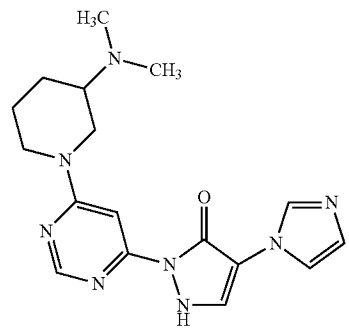 [SMILES: CN(C)C1CCCN(c2cc(-n3[nH]cc(-n4ccnc4)c3=O)ncn2)C1] | 91% | m/z = 355; 1.05 min |
| 154 | 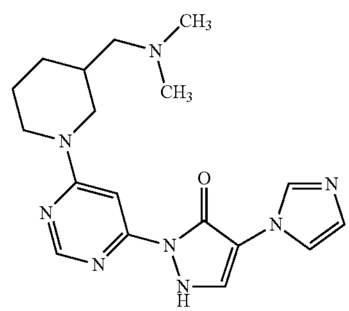 [SMILES: CN(C)CC1CCCN(c2cc(-n3[nH]cc(-n4ccnc4)c3=O)ncn2)C1] | 99% | m/z = 368; 1.09 min |
| 155 | 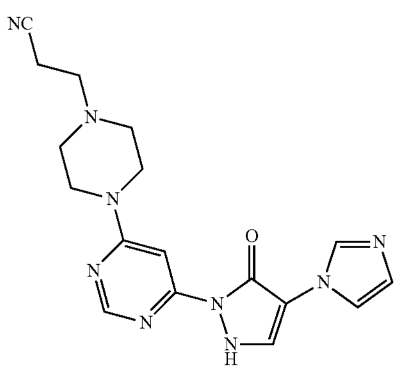 [SMILES: N#CCCN1CCN(c2cc(-n3[nH]cc(-n4ccnc4)c3=O)ncn2)CC1] | 53% | m/z = 366; 1.09 min |

TABLE 9-continued

| Example no. | Structure | Yield (% of th.) | MS (ESI) [M + H]+; LC-MS: R$_t$ (Method 16) |
| --- | --- | --- | --- |
| 156 | 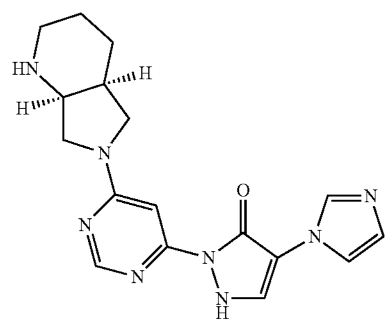 [SMILES: O=c1c(-n2ccnc2)c[nH]n1-c1cc(N2C[C@@H]3CCCN[C@@H]3C2)ncn1] | 38% | m/z = 353; 1.03 min |
| 157 | 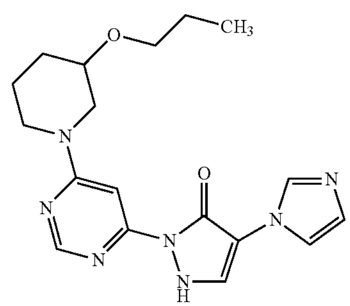 [SMILES: CCCOC1CCCN(c2cc(-n3[nH]cc(-n4ccnc4)c3=O)ncn2)C1] | 89% | m/z = 370; 1.46 min |
| 158 | 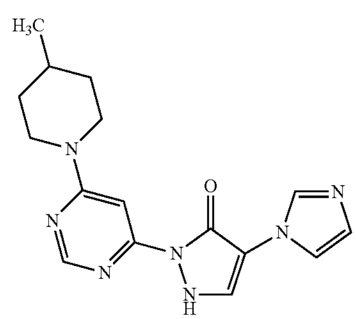 [SMILES: CC1CCN(c2cc(-n3[nH]cc(-n4ccnc4)c3=O)ncn2)CC1] | 73% | m/z = 326; 1.46 min |
| 159 | 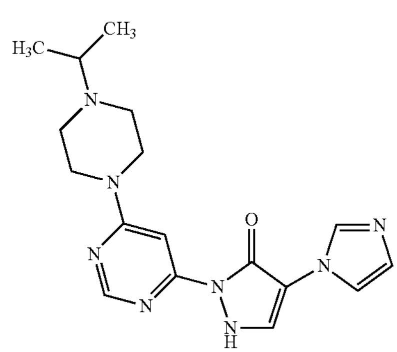 [SMILES: CC(C)N1CCN(c2cc(-n3[nH]cc(-n4ccnc4)c3=O)ncn2)CC1] | 97% | m/z = 355; 1.04 min |

TABLE 9-continued

| Example no. | Structure | Yield (% of th.) | MS (ESI) [M + H]+; LC-MS: R_t (Method 16) |
| --- | --- | --- | --- |
| 160 | 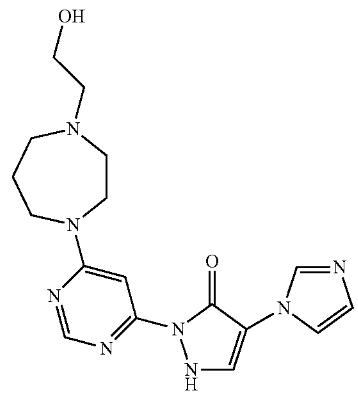 [SMILES: O=c1c(-n2ccnc2)c[nH]n1-c1cc(N2CCCN(CCO)CC2)ncn1] | 41% | m/z = 371; 1.00 min |
| 161 | 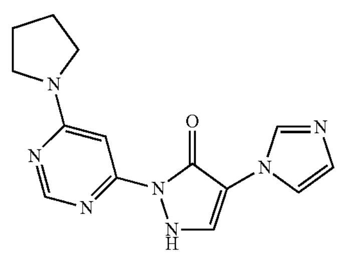 [SMILES: O=c1c(-n2ccnc2)c[nH]n1-c1cc(N2CCCC2)ncn1] | 36% | m/z = 298; 1.27 min |
| 162 | 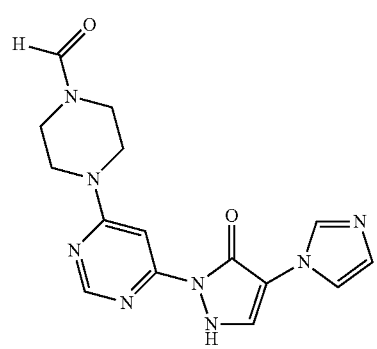 [SMILES: O=CN1CCN(c2cc(-n3[nH]cc(-n4ccnc4)c3=O)ncn2)CC1] | 3% | m/z = 341; 1.18 min |
| 163 | 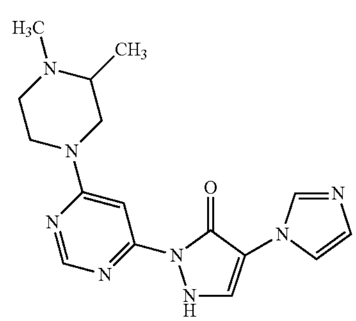 [SMILES: CC1CN(c2cc(-n3[nH]cc(-n4ccnc4)c3=O)ncn2)CCN1C] | 58% | m/z = 341; 1.01 min |

TABLE 9-continued

| Example no. | Structure | Yield (% of th.) | MS (ESI) [M + H]+; LC-MS: R$_t$ (Method 16) |
| --- | --- | --- | --- |
| 164 | 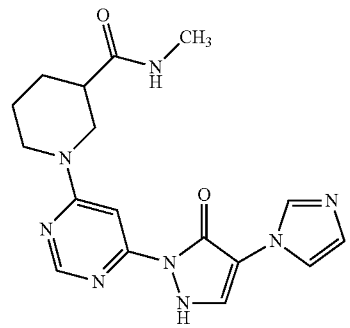 [SMILES: CNC(=O)C1CCCN(c2cc(-n3[nH]cc(-n4ccnc4)c3=O)ncn2)C1] | 33% | m/z = 369; 1.23 min |
| 165 | 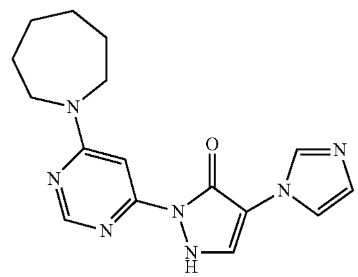 [SMILES: O=c1c(-n2ccnc2)c[nH]n1-c1cc(N2CCCCCC2)ncn1] | 70% | m/z = 326; 1.41 min |
| 166 | 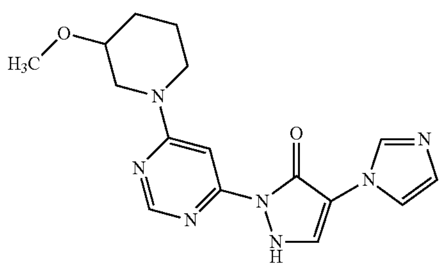 [SMILES: COC1CCCN(c2cc(-n3[nH]cc(-n4ccnc4)c3=O)ncn2)C1] | 60% | m/z = 342; 1.30 min |
| 167 | 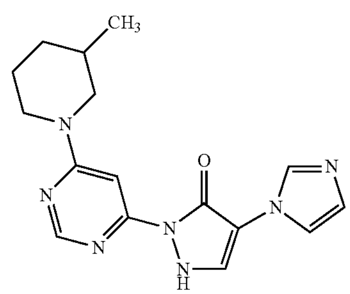 [SMILES: CC1CCCN(c2cc(-n3[nH]cc(-n4ccnc4)c3=O)ncn2)C1] | 86% | m/z = 326; 1.46 min |
| 168 | 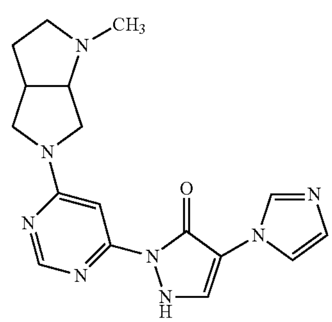 [SMILES: CN1CCC2CN(c3cc(-n4[nH]cc(-n5ccnc5)c4=O)ncn3)CC21] | 71% | m/z = 352; 1.04 min |

TABLE 9-continued

| Example no. | Structure | Yield (% of th.) | MS (ESI) [M + H]+; LC-MS: R$_t$ (Method 16) |
|---|---|---|---|
| 169 | 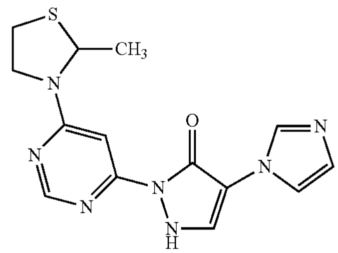 [SMILES: CC1SCCN1c1cc(-n2[nH]cc(-n3ccnc3)c2=O)ncn1] | 6% | m/z = 330; 1.35 min |
| 170 | 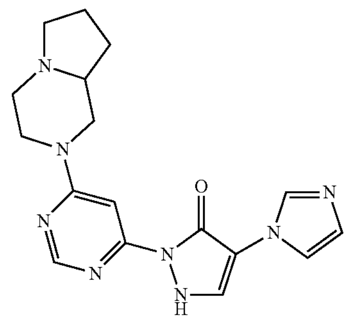 [SMILES: O=c1c(-n2ccnc2)c[nH]n1-c1cc(N2CCN3CCCC3C2)ncn1] | 70% | m/z = 353; 1.00 min |
| 171 | 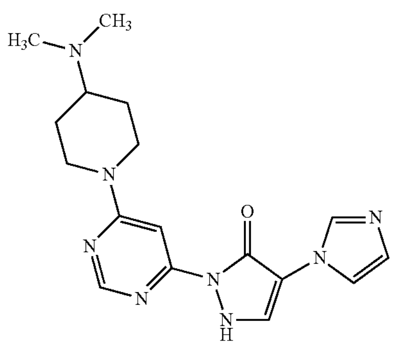 | 60% | m/z = 355; 1.04 min |
| 172 | 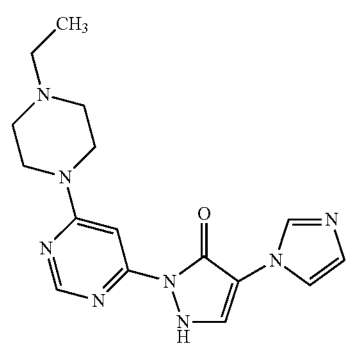 [SMILES: CCN1CCN(c2cc(-n3[nH]cc(-n4ccnc4)c3=O)ncn2)CC1] | 64% | m/z = 341; 1.00 min |
| 173 | 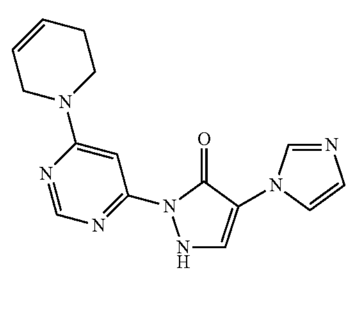 [SMILES: O=c1c(-n2ccnc2)c[nH]n1-c1cc(N2CC=CCC2)ncn1] | 67% | m/z = 310; 1.35 min |

TABLE 9-continued

| Example no. | Structure | Yield (% of th.) | MS (ESI) [M + H]+; LC-MS: $R_t$ (Method 16) |
|---|---|---|---|
| 174 | 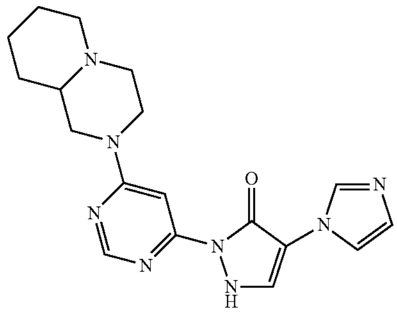 [SMILES: O=c1c(-n2ccnc2)c[nH]n1-c1cc(N2CCN3CCCCC3C2)ncn1] | 99% | m/z = 367; 1.05 min |
| 175 | 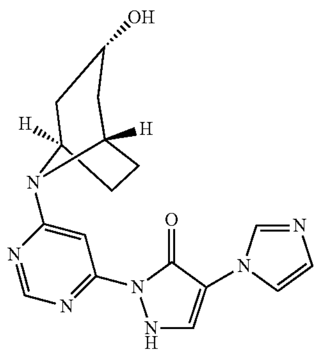 [SMILES: O=c1c(-n2ccnc2)c[nH]n1-c1cc(N2[C@@H]3CC[C@H]2C[C@@H](O)C3)ncn1] | 34% | m/z = 354; 1.26 min |
| 176 | 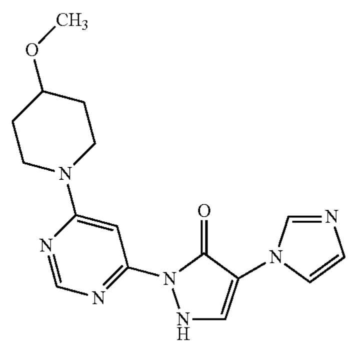 [SMILES: COC1CCN(c2cc(-n3[nH]cc(-n4ccnc4)c3=O)ncn2)CC1] | 66% | m/z = 342; 1.30 min |

Example 177

4-(3-Methyl-1,2,4-oxadiazol-5-yl)-2-(6-morpholin-4-ylpyrimidin-4-yl)-1,2-dihydro-3H-pyrazol-3-one trifluoroacetate

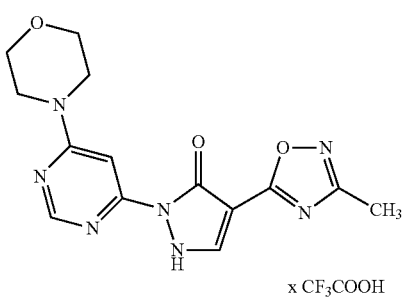 [SMILES: Cc1noc(-c2c[nH]n(-c3cc(N4CCOCC4)ncn3)c2=O)n1]

22 mg (0.5 mmol, 60% strength in mineral oil) sodium hydride are suspended in 1 ml DMF under argon. 38 mg (0.5 mmol) 1-N'-hydroxyethanimidamide ("acetamide oxime") are added and the mixture is heated at 50° C., while stirring. After one hour, 50 mg (0.2 mmol) of the compound from Example 54A are added. The reaction mixture is stirred at 80° C. for 2 h. A mixture of in each case 22 mg (0.5 mmol, 60% strength in mineral oil) sodium hydride and 38 mg (0.5 mmol) 1-N'-hydroxyethanimidamide in 1 ml DMF, which has first been heated at 50° C. for 30 min, while stirring, is subsequently added again twice in succession and the reaction mixture is stirred at 80° C. for a further 30 min after each addition. Thereafter, the mixture is allowed to cool and is concentrated. The residue is dissolved in a mixture of in each case 2 ml water, methanol and 1 N hydrochloric acid and purified via preparative HPLC (RP18 column; mobile phase: acetonitrile/water gradient with addition of 0.1% TFA).

Yield: 12 mg (17% of th.)

LC-MS (Method 4): $R_t$=1.35 min; MS (ESIpos): m/z=330 [M+H]+;

$^1$H-NMR (400 MHz, DMSO-$d_6$): δ=8.58 (s, 1H), 8.04 (s, 1H), 7.29 (s, 1H), 3.85-3.65 (m, 8H), 2.23 (s, 3H).

Example 178

4-(3-Methyl-1,2,4-oxadiazol-5-yl)-2-(6-morpholin-4-ylpyrimidin-4-yl)-1,2-dihydro-3H-pyrazol-3-one hydrochloride

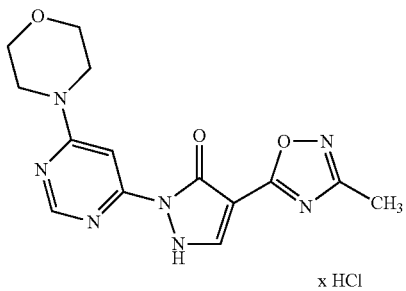 [SMILES: Cc1noc(-c2c[nH]n(-c3cc(N4CCOCC4)ncn3)c2=O)n1]

x HCl 10 mg (0.02 mmol) of the compound from Example 177 are stirred with a 4 N solution of hydrogen chloride in dioxane at RT for 2 h. Thereafter, the solvent is decanted off and the solid is stirred in tert-butyl methyl ether three times in succession and the solvent is decanted off each time. The solid which remains is dried under a high vacuum.

Yield: 7 mg (86% of th.)

LC-MS (Method 8): $R_t$=1.24 min; MS (ESIpos): m/z=330 [M+H]$^+$;

$^1$H-NMR (400 MHz, DMSO-d$_6$): δ=8.58 (s, 1H), 8.08 (s, 1H), 7.29 (s, 1H), 4.00-3.50 (m, 8H), 2.23 (s, 3H).

Example 179

2-(6-Methoxypyrimidin-4-yl)-4-(1H-1,2,3-triazol-1-yl)-1,2-dihydro-3H-pyrazol-3-one hydrochloride

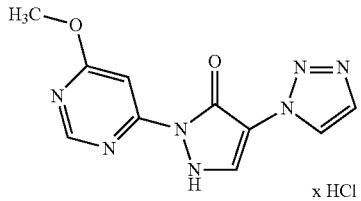 [SMILES: COc1cc(-n2[nH]cc(-n3ccnn3)c2=O)ncn1]

x HCl 0.3 ml (6.6 mmol) methanol are initially introduced into 15 ml dioxane. 1.3 ml (2.7 mmol) of a 2 M solution of the phosphazene base P2-tert-butyl in THF are added slowly, while stirring, and the mixture is stirred at RT for 15 min. 350 mg (1.3 mmol) of the compound from Example 52A are subsequently added and the mixture is reacted in a single mode microwave (CEM Explorer) at 150° C. for 2 h. A further 2 ml (49.2 mmol) methanol are then added and the mixture is reacted again in a single mode microwave (CEM Explorer) under the same conditions for 2 h. After cooling, the reaction mixture is concentrated and the residue is purified via preparative HPLC (RP18 column; mobile phase: acetonitrile/water gradient with addition of 0.1% TFA). The product-containing fractions are combined and the mixture is concentrated on a rotary evaporator. The residue is dried under a high vacuum and 3 ml of a 4 N solution of hydrogen chloride in dioxane is subsequently added. The mixture is stirred at RT for 30 min and the solid is then filtered off and dried under a high vacuum.

Yield: 60 mg (15% of th.)

LC-MS (Method 7): $R_t$=0.82 min; MS (ESIpos): m/z=260 [M+H]$^+$;

$^1$H-NMR (400 MHz, DMSO-d$_6$): δ=8.80 (s, 1H), 8.59 (s, 1H), 8.43 (s, 1H), 7.90 (s, 1H), 7.70 (s, 1H), 4.00 (s, 3H).

Example 180

2-[6-(4-Pyrrolidin-1-ylpiperidin-1-yl)pyrimidin-4-yl]-4-(1H-1,2,3-triazol-1-yl)-1,2-dihydro-3H-pyrazol-3-one

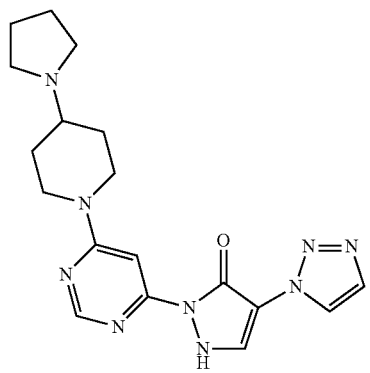 [SMILES: O=c1c(-n2ccnn2)c[nH]n1-c1cc(N2CCC(N3CCCC3)CC2)ncn1]

481 mg (2.3 mmol) of the compound from Example 3A, 600 mg (2.3 mmol) of the compound from Example 30A and 79 mg (0.5 mmol) p-toluenesulfonic acid are initially introduced into 8 ml THF and the mixture is reacted in a single mode microwave (Emrys Optimizer) at 170° C. for 30 min. For working up, the reaction mixture is concentrated and the residue is chromatographed via preparative HPLC (Method 17). The product fractions are lyophilized and thereafter water/acetonitrile (5:1) is added. The solution is heated, treated with ultrasound and filtered over a Millipore filter (0.45 μm). The filtrate is concentrated to dryness in vacuo.

Yield: 17 mg (2% of th.)

LC-MS (Method 8): $R_t$=0.94 min; MS (ESIpos): m/z=382 [M+H]$^+$;

$^1$H-NMR (400 MHz, DMSO-d$_6$): δ=8.41 (s, 1H), 8.35 (s, 1H), 8.07 (s, 1H), 7.70 (s, 1H), 7.68 (s, 1H), 4.43-4.23 (m, 2H), 3.18-2.88 (m, 6H), 2.14-2.00 (m, 2H), 1.92-1.76 (m, 4H), 1.56-1.40 (m, 2H), 1.16 (t, 1H).

B. EVALUATION OF THE PHARMACOLOGICAL ACTIVITY

The pharmacological properties of the compounds according to the invention can be demonstrated in the following assays:

| Abbreviations: | |
|---|---|
| DMEM | Dulbecco's modified Eagle medium |
| FCS | fetal calf serum |
| TMB | 3,3',5,5'-tetramethylbenzidine |
| Tris | tris(hydroxymethyl)-aminomethane |

1. In vitro Tests for Determination of the Activity and Selectivity of HIF Prolyl 4-Hydroxylase Inhibitors 1.a) Inhibition of the Activity of HIF Prolyl Hydroxylase:

Hydroxylated HIF bonds specifically to the von Hippel-Lindau protein-elongin B-elongin C complex (VBC complex). This interaction occurs only if HIF is hydroxylated on a conserved prolyl radical. It is the basis for the biochemical determination of HIF prolyl hydroxylase activity. The test is carried out as described [Oehme F., Jonghaus W., Narouz-Ott L., Huetter J., Flamme I., Anal. Biochem. 330 (1), 74-80 (2004)]:

A clear 96-well microtiter plate coated with NeutrAvidin HBC (Pierce) is incubated with blocker casein for 30 minutes. The plate is then washed three times with 200 µl each time of wash buffer (50 mM Tris, pH 7.5, 100 mM NaCl, 10% (v/v) blocker casein, 0.05% (v/v) Tween 20) per well. The peptide biotin-DLDLEMLAPYIPMDDDFQL (Eurogentec, 4102 Seraing, Belgium) is added in a concentration of 400 nM in 100 µl wash buffer. This peptide serves as a substrate for the prolyl hydroxylation and is bonded to the microtiter plate. After incubation for 60 minutes, the plate is washed three times with wash buffer, incubated with 1 mM biotin in blocker casein for 30 minutes and then washed again three times with wash buffer.

To carry out the prolyl hydroxylase reaction, the peptide substrate bonded to the plate is incubated with a cell lysate containing prolyl hydroxylase for 1 to 60 minutes. The reaction takes place in 100 µl reaction buffer (20 mM Tris, pH 7.5, 5 mM KCl, 1.5 mM MgCl2, 1 µM-1 mM 2-oxoglutarate, 10 µM FeSO4, 2 mM ascorbate) at room temperature. The reaction mixture moreover contains various concentrations of the prolyl hydroxylase inhibitor to be tested. The test substance is preferably, but not exclusively, employed at concentrations of between 1 nM and 100 µM. The reaction is stopped by washing the plate three times with wash buffer.

For quantitative determination of the prolyl hydroxylation, a fusion protein which contains both thioredoxin from E. coli and the VBC complex in 80 µl bonding buffer (50 mM Tris, pH 7.5, 120 mM NaCl) is added. After 15 minutes, 10 µl of a solution of polyclonal anti-thioredoxin antibodies from rabbit in bonding buffer are added. After a further 30 minutes, 10 µl of a solution of anti-rabbit immunoglobulin coupled to horseradish peroxidase in bonding buffer are added. After incubation at room temperature for 30 minutes, the plate is washed three times with wash buffer in order to remove non-bonded VBC complex and antibodies. To determine the amount of bonded VBC complex, the plate is incubated with TMB for 15 minutes. The color reaction is ended by addition of 100 µl 1 M sulfuric acid. The amount of bonded VBC complex is determined by measurement of the optical density at 450 nm. It is proportional to the amount of hydroxylated proline in the peptide substrate.

Alternatively, a VBC complex coupled to europium (Perkin Elmer) can be used for detection of the prolyl hydroxylation. In this case, the amount of bonded VBC complex is determined by the fluorescence with respect to time. The use of VBC complex labeled with [$^{35}$S]-methionine is moreover possible. For this, the radioactively labeled VBC complex can be prepared by in vitro transcription-translation in reticulocyte lysate.

The embodiment examples inhibit the activity of HIF prolyl hydroxylase in this test with an IC50 value of ≤30 µM. Representative IC50 values for the embodiment examples are reproduced in the following Table 1:

TABLE 1

| Example no. | IC$_{50}$ [µM] |
|---|---|
| 5 | 1.2 |
| 7 | 0.34 |
| 10 | 0.5 |
| 12 | 0.75 |
| 17 | 0.56 |
| 43 | 1.8 |
| 45 | 0.78 |
| 50 | 1.4 |
| 55 | 2 |
| 60 | 1.4 |
| 61 | 1.1 |
| 62 | 0.05 |
| 72 | 0.49 |
| 83 | 1.9 |
| 85 | 0.19 |
| 91 | 2.8 |
| 101 | 1.7 |
| 103 | 0.35 |
| 113 | 0.74 |
| 129 | 0.36 |
| 166 | 0.69 |

1.b) Cellular, Functional in vitro Test:

The activity of the compounds according to the invention is quantified with the aid of a recombinant cell line. The cell is originally derived from a human lung carcinoma cell line (A549, ATCC: American Type Culture Collection, Manassas, Va. 20108, USA). The test cell line is transfected in a stable manner with a vector which contains the reporter gene of Photinus pyralis luciferase (called luciferase in the following) under the control of an artificial minimal promoter. The minimal promoter comprises two hypoxia-responsible elements upstream of a TATA box [Oehme F., Ellinghaus P., Kolkhof P., Smith T. J., Ramakrishnan S., Hütter J., Schramm M., Flamme I., Biochem. Biophys. Res. Commun. 296 (2), 343-9 (2002)]. Under the effect of hypoxia (e.g. culturing in the presence of 1% oxygen for 24 hours) or under the action of non-selective dioxygenase inhibitors (e.g. desferroxamine in a concentration of 100 µM, cobalt chloride in a concentration of 100 µM or N-oxalylglycine diethyl ester in a concentration of 1 mM), the test cell line produces luciferase, which can be detected and quantified with the aid of suitable bioluminescence reagents (e.g. Steady-Glo® Luciferase Assay System, Promega Corporation, Madison, Wis. 53711, USA) and a suitable luminometer.

Test procedure: On the day before the test, the cells are plated out in an exactly calculated amount of culture medium (DMEM, 10% FCS, 2 mM glutamine) in 384- or 1,536-well microtiter plates and kept in a cell incubator (96% atmospheric humidity, 5% v/v $CO_2$, 37° C.). On the test day, the test substances are added to the culture medium in graduated concentrations. No test substance is added to the cells in batches serving as negative controls. As a positive control for determination of the sensitivity of the cell to inhibitors, desferroxamine e.g. is added in a final concentration of 100 µM. Six to 24 hours after transfer of the test substances into the wells of the microtiter plates, the resulting light signal is measured in the luminometer. A dose/effect relationship is plotted with the aid of the measurement values, which serves as the basis for determining the half-maximum active concentration (called the $EC_{50}$ value).

1.c) Cellular, Functional in vitro Test of Modification of the Gene Expression:

To investigate the modification of the expression of specific mRNAs in human cell lines after treatment with test substances, the following cell lines are cultured on 6- or 24-well plates: human hepatoma cells (HUH, JCRB Cell Bank, Japan), human embryonal kidney fibroblasts (HEK/293, ATCC, Manassas, Va. 20108, USA), human cervical carcinoma cells (HeLa, ATCC, Manassas, Va. 20108, USA), human umbilical vein endothelial cells (HUVEC, Cambrex, East Rutherford, N.J. 07073, USA). 24 hours after addition of the test substances, the cells are washed with phosphate-buffered saline and the total RNA is obtained from them using a suitable method (e.g. Trizol® reagent, Invitrogen GmbH, 76131 Karlsruhe, Germany).

For a typical analysis experiment, 1 µg each of the total RNA obtained in this way is digested with DNase I and translated into a complementary DNA (cDNA) using a suitable reverse transcriptase reaction (ImProm-II Reverse Transcription System, Promega Corporation, Madison, Wis. 53711, USA). 2.5% of the cDNA batch obtained in this way is used in each case for the polymerase chain reaction. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.). The primer-probe combinations used here are generated by means of Primer Express 1.5 Software (Applied Biosystems, Inc.). Specifically, the mRNAs of erythropoietin, carboanhydrase IX, lactate dehydrogenase A and vascular endothelial cell growth factor are investigated.

Substances according to the present invention lead to a significant dose-dependent increase in the mRNA of hypoxia-induced genes in cells of human origin.

2. In vivo Tests for Detection of the Action in the Cardiovascular System 2.a) In vivo Test of Modification of Gene Expression:

The test compounds dissolved in suitable solvents are administered to mice or rats either orally by stomach tube administration, intraperitoneally or intravenously. Typical dosages are 0.1, 0.5, 1, 5, 10, 20, 50, 100 and 300 mg substance per kg of body weight and administration. Control animals receive only solvent. 4, 8 or 24 hours after administration of the test substance the animals are sacrificed with an overdose of isoflurane and a subsequent fracture of the neck and the organs to be investigated are removed. Parts of the organs are shock-frozen in liquid nitrogen. Total RNA is obtained from the organ parts as described under B.1.a) and this is translated into a cDNA. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.).

Substances according to the present invention lead to a significant dose-dependent increase in the mRNA of erythropoietin in the kidney after oral or parenteral administration compared with the placebo control.

2.b) Determination of the Erythropoietin Level in Serum:

The test substance in a suitable solvent is administered to mice or rats either intraperitoneally or orally once or twice daily. Typical dosages are 0.1, 0.5, 1, 5, 10, 20, 50, 100 and 300 mg substance per kg of body weight and administration. Placebo control animals receive only solvent. Before the administration and four hours after the last administration of substance, 50 µl of blood are taken from the animals from the retroorbital venous plexus or the tail vein under short narcosis. The blood is rendered uncoagulable by addition of lithium heparin. The blood plasma is obtained by centrifugation. The content of erythropoietin in the blood plasma is determined with the aid of an erythropoietin-ELISA (Quantikine® mouse Epo Immunoassay, R&D Systems, Inc., Minneapolis, USA) in accordance with the manufacturer's instructions. The measurement values are converted into pg/ml with the aid of a reference measurement recorded for mouse erythropoietin.

Substances according to the present invention lead to a significant dose-dependent increase in the plasma erythropoietin after oral and parental administration compared with the starting value and the placebo control.

2.c) Determination of the Cell Composition of Peripheral Blood:

The test substance in a suitable solvent is administered to mice or rats either intraperitoneally or orally once or twice daily for several days. Typical dosages are e.g. 0.1, 0.5, 1, 5, 10, 20, 50, 100 and 300 mg substance per kg of body weight and administration. Control animals receive only solvent. At the end of the study, blood is taken from the animals from the venous plexus of the corner of the eye or the tail vein under short narcosis and is rendered uncoagulable by addition of sodium citrate. The concentrations of erythrocytes, leukocytes and thrombocytes are determined in the blood samples in a suitable electronic measuring apparatus. The concentration of the reticulocytes is determined by microscope screening of in each case 1,000 erythrocytes with the aid of blood smears stained with a stain solution suitable for this purpose (KABE Labortechnik, Nümbrecht). For determination of the hematocrit, blood is taken from the retroorbital venous plexus by means of a hematocrit capillary and the hematocrit value is read off manually after centrifugation of the capillary in a centrifuge suitable for this purpose.

Substances according to the present invention lead to a significant dose-dependent increase in the hematocrit, the erythrocyte count and the reticulocytes after oral and parenteral administration compared with the starting value and the placebo control.

3. Determination of the Solubility

Preparation of the Starting Solution (Initial Solution):

At least 1.5 mg of the test substance are weighed out accurately into a Wide Mouth 10 mm Screw V-Vial (from Glastechnik Gräfenroda GmbH, Art. No. 8004-WM-H/V 15µ) with fitting screw cap and septum, DMSO is added to give a concentration of 50 mg/ml and the mixture is vortexed for 30 minutes.

Preparation of the Calibration Solutions:

The required pipetting steps are carried out in a 1.2 ml Deep Well Plate (DWP) with 96 wells using a liquid handling robot. The solvent used is a mixture of acetonitrile/water 8:2.

Preparation of the starting solution for calibration solutions (stock solution): 833 µl of the solvent mixture are added to 10 µl of the initial solution (concentration=600 µg/ml), and the mixture is homogenized. For each test substance, 1:100 dilutions are prepared in separate DWPs, and the dilutions for their part are homogenized.

Calibration solution 5 (600 ng/ml): 270 µl of solvent mixture are added to 30 µl of the stock solution, and the mixture is homogenized.

Calibration solution 4 (60 ng/ml): 270 µl of solvent mixture are added to 30 µl of calibration solution 5, and the mixture is homogenized.

Calibration solution 3 (12 ng/ml): 400 µl of solvent mixture are added to 100 µl of calibration solution 4, and the mixture is homogenized.

Calibration solution 2 (1.2 ng/ml): 270 µl of solvent mixture are added to 30 µl of calibration solution 3, and the mixture is homogenized.

Calibration solution 1 (0.6 ng/ml): 150 µl of solvent mixture are added to 150 µl of calibration solution 2, and the mixture is homogenized.

Preparation of the Sample Solutions:

The required pipetting steps are carried out in a 1.2 ml DWP with 96 wells using a liquid handling robot. 1000 µl of PBS buffer pH 6.5 are added to 10.1 µl of the stock solution. (PBS buffer pH 6.5: 61.86 g of sodium chloride, 39.54 g of sodium dihydrogen phosphate and 83.35 g of 1N aqueous sodium hydroxide solution are weighed out into a 1 liter measuring flask, the flask is filled with water and the mixture is stirred for about 1 hour. From this solution, 500 ml are added to a 5 liter measuring flask, and the flask is filled with water. Using 1N aqueous sodium hydroxide solution, the pH is adjusted to 6.5.)

Practice:

The required pipetting steps are carried out in a 1.2 ml DWP with 96 wells using a liquid handling robot. Using a temperature-adjustable shaker, the sample solutions prepared in this manner are shaken at 20° C. and 1400 rpm for 24 hours. From these solutions, in each case 180 µl are removed and transferred into Beckman polyallomer centrifuge tubes. These solutions are centrifuged at about 223 000×g for 1 hour. From each sample solution, 100 µl of the supernatant are removed and diluted 1:10 and 1:1000 with PBS buffer 6.5.

Analysis:

The samples are analyzed by HPLC/MS-MS. Quantification is carried out using a five point calibration curve of the test compound. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 7) sample solution 1:10.

HPLC/MS-MS Method

HPLC: Agilent 1100, quat. pump (G1311A), autosampler CTC HTS PAL, degasser (G1322A) and column thermostat (G1316A); column: Oasis HLB 20 mm×2.1 mm, 25µ; temperature: 40° C.; mobile phase A: water+0.5 ml of formic acid/l; mobile phase B: acetonitrile+0.5 ml of formic acid/l; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS initial splitter 1:20; measurement in the ESI mode.

C. EMBODIMENT EXAMPLES FOR PHARMACEUTICAL COMPOSITIONS

The compounds according to the invention can be converted into pharmaceutical formulations as follows.

Tablet:

Composition:

100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm.

Preparation:

The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:

Composition:

1,000 mg of the compound according to the invention, 1,000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.

Preparation:

The Rhodigel is suspended in ethanol and the compound according to the invention is added to the suspension. The water is added with stirring. The mixture is stirred for approx. 6 h until swelling of the Rhodigel has ended.

Solution for Oral Administration:

Composition:

500 mg of the compound according to the invention, 2.5 g polysorbate and 97 g polyethylene glycol 400.20 g of oral solution correspond to an individual dose of 100 mg of the compound according to the invention.

Preparation:

The compound according to the invention is suspended in a mixture of polyethylene glycol and polysorbate, while stirring. The stirring operation is continued until solution of the compound according to the invention is complete.

i.v. Solution:

The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and is transferred into sterile and pyrogen-free injection containers.

The invention claimed is:

1. A compound of the formula (I)

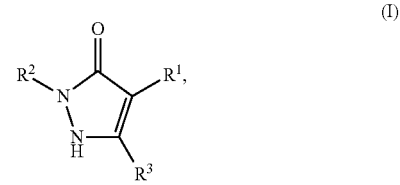

in which $R^1$ represents a heteroaryl group of the formula

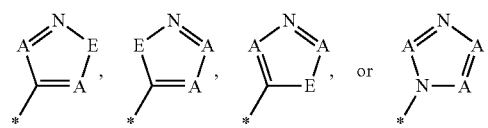

wherein

\* denotes the linkage point with the dihydropyrazolone ring,

A in each individual occurrence denotes C—$R^4$ or N, wherein at most two ring members A represent N at the same time, and E denotes O, S or N—$R^5$, $R^2$ represents a heteroaryl group of the formula

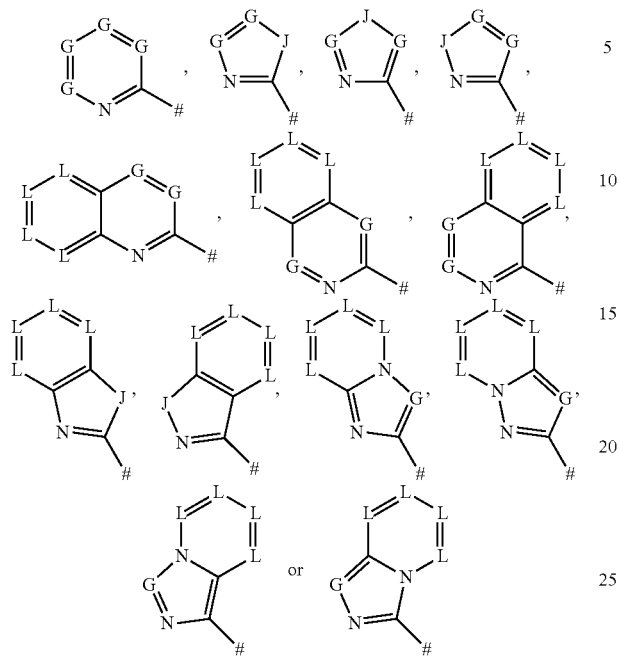

wherein
# denotes the linkage point with the dihydropyrazolone ring,
G in each individual occurrence denotes C—$R^6$ or N, wherein at most two ring members G represent N at the same time,
J denotes O, S or N—$R^7$ and
L in each individual occurrence denotes C—$R^8$ or N, wherein at most two ring members L represent N at the same time,
wherein
$R^4$, $R^6$ and $R^8$ are identical or different and in each individual case, independently of one another, represents hydrogen or a substituent chosen from the series consisting of halogen, cyano, nitro, $(C_1-C_6)$-alkyl, $(C_3-C_7)$-cycloalkyl, 4- to 10-membered heterocycloalkyl, phenyl, 5- or 6-membered heteroaryl, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein (i) $(C_1-C_6)$-alkyl in its turn can be substituted once to three times in an identical or different manner by radicals chosen from the series consisting of halogen, cyano, oxo, $(C_3-C_7)$-cycloalkyl, 4- to 10-membered heterocycloalkyl, phenyl, 5- or 6-membered heteroaryl, —C(=O)—$R^9$, —C(=O)—$OR^{10}$, —C(=O)—$NR^{11}R^{12}$, —O—C(=O)—$R^9$, —C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the cycloalkyl, heterocycloalkyl, phenyl and heteroaryl radicals mentioned last in their turn can in each case be substituted up to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl, (ii) $(C_3-C_7)$-cycloalkyl, 4- to 10-membered heterocycloalkyl, phenyl and 5- or 6-membered heteroaryl in their turn can in each case be substituted once to three times in an identical or different manner by radicals chosen from the series consisting of $(C_1-C_6)$-alkyl, halogen, cyano, oxo, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, $NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the alkyl radical mentioned last can in its turn be substituted up to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and/or 5- or 6-membered heteroaryl, (iii) $R^9$, $R^{10}$, $R^{11}$, $R^{13}$, $R^{14}$, $R^{17}$, $R^{19}$, $R^{21}$, $R^{24}$, $R^{25}$, $R^{26}$, $R^{28}$, $R^{29}$ and $R^{30}$ independently of one another for each individual occurrence represent a radical chosen from the series consisting of hydrogen, $(C_1-C_6)$-alkyl, $(C_3-C_7)$-cycloalkyl, 4- to 10-membered heterocycloalkyl, phenyl and 5- or 6-membered heteroaryl, wherein
$(C_3-C_7)$-cycloalkyl, 4- to 10-membered heterocycloalkyl, phenyl and 5- or 6-membered heteroaryl in their turn can in each case be substituted up to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl
and
$(C_1-C_6)$-alkyl can be substituted once to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkyl-amino, hydroxycarbonyl, $(C_1-C_4)$-alkoxycarbonyl, $(C_3-C_7)$-cycloalkyl, 4- to 7-membered hetero-cycloalkyl, phenyl and/or 5- or 6-membered heteroaryl, (iv) $R^{12}$, $R^{15}$, $R^{16}$, $R^{18}$, $R^{20}$, $R^{22}$, $R^{23}$, $R^{27}$ and $R^{31}$ independently of one another for each individual occurrence represent a radical chosen from the series consisting of hydrogen and $(C_1-C_6)$-alkyl, wherein $(C_1-C_6)$-alkyl can be substituted once to three times in an identical or different manner by halogen, cyano, hydroxyl, trifluoromethoxy, $(C_1-C_4)$-alkoxy, amino, mono-$(C_1-C_4)$-alkylamino, di-$(C_1-C_6)$-alkylamino, hydroxycarbonyl and/or $(C_1-C_4)$-alkoxycarbonyl, and/or wherein
(v) $R^{11}$ and $R^{12}$, $R^{14}$ and $R^{15}$, $R^{16}$ and $R^{17}$, $R^{18}$ and $R^{19}$, $R^{20}$ and $R^{21}$, $R^{21}$ and $R^{22}$, $R^{23}$ and $R^{24}$, $R^{26}$ and $R^{27}$ and $R^{30}$ and $R^{31}$ in each case paired together with the atoms to which they are bonded can form a 5- or 6-membered heterocycloalkyl ring, which can be substituted once to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkyl-amino, di-$(C_1-C_4)$-alkylamino, hydroxycarbonyl and/or $(C_1-C_4)$-alkoxycarbonyl, and $R^5$ and $R^7$ are identical or different and independently of one another represent hydrogen or a substituent chosen from the series consisting of $(C_1-C_6)$-alkyl, $(C_3-C_7)$-cycloalkyl, 4- to 7-membered heterocycloalkyl, phenyl and 5- or 6-membered heteroaryl, wherein (i) $(C_1-C_6)$-alkyl in its turn can be substituted once to three times in an identical or different manner by radicals chosen from the series consisting of halogen, cyano, oxo, $(C_3-C_7)$-cycloalkyl, 4- to 7-membered heterocycloalkyl, phenyl, 5- or 6-membered heteroaryl, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the cycloalkyl, heterocycloalkyl, phenyl and heteroaryl radicals mentioned last in their turn can in each case be substituted up to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl, and (ii) $(C_1-C_7)$-cycloalkyl, 4- to 7-membered heterocycloalkyl, phenyl and 5- or 6-membered heteroaryl in their turn can in each case be substituted once to three times in an identical or different manner by radicals chosen from the series consisting of $(C_1-C_6)$-alkyl, halogen, cyano, oxo, —C(=O)—$R^9$, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$SO_2$—$R^{25}$, —$SO_2$—$NR^{26}R^{27}$, —$OR^{28}$, —$SR^{29}$ and —$NR^{30}R^{31}$, wherein the alkyl radical mentioned last in its turn can be substituted up to three times in an identical or different manner by halogen, cyano, hydroxyl, trifluoromethoxy, $(C_1-C_6)$-alkoxy, amino, mono-$(C_1-C_4)$-alkylamino, di-$(C_1-C_4)$-alkylamino, hydroxycarbonyl, $(C_1-C_6)$-alkoxycarbonyl, $(C_1-C_6)$-cycloalkyl, 4- to 7-membered heterocycloalkyl, phenyl and/or 5- or 6-membered heteroaryl, wherein (a) $R^9$, $R^{10}$, $R^{11}$, $R^{13}$, $R^{14}$, $R^{17}$, $R^{19}$, $R^{21}$, $R^{24}$, $R^{25}$, $R^{26}$, $R^{28}$, $R^{29}$ and $R^{30}$ independently of one another for each individual occurrence represent a radical chosen from the series consisting of hydrogen, $(C_1-C_6)$-alkyl, $(C_3-C_7)$-cycloalkyl, 4- to 7-membered heterocycloalkyl, phenyl and 5- or 6-membered heteroaryl, wherein $(C_3-C_7)$-cycloalkyl, 4- to 7-membered heterocycloalkyl, phenyl and 5- or 6-membered heteroaryl in their turn can in each case be substituted up to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl and $(C_1-C_6)$-alkyl can be substituted once to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkyl-amino, hydroxycarbonyl, $(C_1-C_4)$-alkoxycarbonyl, $(C_3-C_7)$-cycloalkyl, 4- to 7-membered hetero-cycloalkyl, phenyl and/or 5- or 6-membered heteroaryl, (b) $R^{12}$, $R^{15}$, $R^{16}$, $R^{18}$, $R^{20}$, $R^{22}$, $R^{23}$, $R^{27}$ and $R^{31}$ independently of one another for each individual occurrence represent a radical chosen from the series consisting of hydrogen and $(C_1-C_6)$-alkyl, wherein $(C_1-C_6)$-alkyl can be substituted once to three times in an identical or different manner by halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and/or $(C_1-C_4)$-alkoxycarbonyl, and/or (c) $R^{11}$ and $R^{12}$, $R^{14}$ and $R^{15}$, $R^{16}$ and $R^{17}$, $R^{18}$ and $R^{19}$, $R^{20}$ and $R^{21}$, $R^{21}$ and $R^{22}$, $R^{23}$ and $R^{24}$, $R^{26}$ and $R^{27}$ and $R^{30}$ and $R^{31}$ in each case paired together with the atoms to which they are bonded can form a 5- or 6-membered heterocycloalkyl ring, which can be substituted once to three times in an identical or different manner by halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkyl-amino, di-$(C_1-C_4)$-alkylamino, hydroxycarbonyl and/or $(C_1-C_4)$-alkoxycarbonyl, and $R^3$ represents hydrogen, $(C_1-C_6)$-alkyl or $(C_3-C_7)$-cycloalkyl, and their salts, solvates and solvates of the salts, with the exception of the compounds 3-methyl-1-(pyridin-2-yl)-4-(1-pyridin-2-yl-3-methyl-1H-pyrazol-5-yl)-2H-3-pyrazolin-5(1H)-one, 3',5-dimethyl-2-phenyl-1'-(4-phenyl-1,3-thiazol-2-yl)-1'H,2H-3,4'-bipyrazol-5'-ol, 3',5-dimethyl-2-phenyl-1'-(4-thiophen-2-yl-1,3-thiazol-2-yl)-1'H,2H-3,4'-bipyrazol-5'-ol, 3',5-dimethyl-1'-(4-methyl-1,3-thiazol-2-yl)-2-phenyl-1'H,2H-3,4'-bipyrazol-5'-ol, 2-(4-chlorophenyl)-3',5-dimethyl-1'-(4-phenyl-1,3-thiazol-2-yl)-1'H,2H-3,4'-bipyrazol-5'-ol and 2-tert-butyl-1'-[4-(4-chlorophenyl)-1,3-thiazol-2-yl]-3',5-dimethyl-1'H,2H-3,4'-bipyrazol-5'-ol.

2. A compound of the formula (I) as claimed in claim 1, in which $R^1$ represents a heteroaryl group of the formula

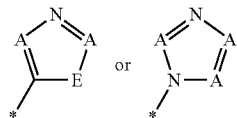

wherein
* denotes the linkage point with the dihydropyrazolone ring,
A in each individual occurrence denotes C—$R^4$ or N, wherein at most two ring members A represent N at the same time, wherein
$R^4$ in each individual case, independently of one another, represents hydrogen or a substituent chosen from the series consisting of fluorine, chlorine, bromine, cyano, nitro, $(C_1-C_6)$-alkyl, hydroxyl, $(C_1-C_6)$-alkoxy, trifluoromethoxy, amino, mono-$(C_1-C_6)$-alkylamine, di-$(C_1-C_6)$-alkylamino, hydroxycarbonyl and $(C_1-C_6)$-alkoxycarbonyl, wherein the $(C_1-C_6)$-alkyl radical mentioned in its turn can be substituted up to three times in an identical or different manner by fluorine, chlorine, bromine, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and/or $(C_1-C_4)$-alkoxycarbonyl,
and
E denotes O, S or N—$R^5$, wherein
$R^5$ represents hydrogen or $(C_1-C_6)$-alkyl,
$R^2$ represents a heteroaryl group of the formula

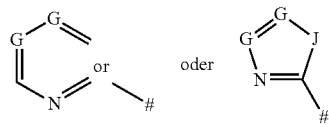

wherein
# denotes the linkage point with the dihydropyrazolone ring,
G in each case denotes C—$R^6$ or N, wherein not more than one of the two ring members G represents N, wherein
$R^6$ in each individual case, independently of one another, represents hydrogen or a substituent chosen from the series consisting of fluorine, chlorine, bromine, cyano, $(C_1-C_6)$-alkyl, $(C_3-C_6)$-cycloalkyl, 4- to 6-membered heterocycloalkyl, phenyl, 5- or 6-membered heteroaryl, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$OR^{28}$ and —$NR^{30}R^{31}$, wherein
(i) $(C_1-C_6)$-alkyl in its turn can be substituted once to three times in an identical or different manner by radicals chosen from the series consisting of fluorine, chlorine, bromine, cyano, $(C_3-C_6)$-cycloalkyl, 4- to 6-membered heterocycloalkyl, phenyl, 5- or 6-membered heteroaryl, —C(=O)—$OR^{10}$, —C(=O)—$NR^{11}R^{12}$, —O—C(=O)—$R^{13}$, —O—C(=O)—$NR^{14}R^{15}$, —$NR^{16}$—C(=O)—$R^{17}$, —$NR^{18}$—C(=O)—$OR^{19}$, —$NR^{20}$—C(=O)—$NR^{21}R^{22}$, —$NR^{23}$—$SO_2$—$R^{24}$, —$OR^{28}$ and —$NR^{30}R^{31}$, wherein the cycloalkyl, heterocycloalkyl, phenyl and heteroaryl radicals mentioned last in their turn can in each case be substituted up to twice in an identical or different manner by fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and/or $(C_1-C_4)$-alkoxycarbonyl,
(ii) $(C_3-C_6)$-cycloalkyl, 4- to 6-membered heterocycloalkyl, phenyl and 5- or 6-membered heteroaryl in their turn can in each case be substituted once or twice in an identical or different manner by fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxy-carbonyl and/or $(C_1-C_4)$-alkoxycarbonyl,
(iii) $R^{10}$, $R^{11}$, $R^{13}$, $R^{14}$, $R^{17}$, $R^{19}$, $R^{21}$, $R^{24}$, $R^{28}$ and $R^{30}$ independently of one another for each individual occurrence represent a radical chosen from the series consisting of hydrogen, $(C_1-C_6)$-alkyl, $(C_3-C_6)$-cycloalkyl, 4- to 6-membered heterocycloalkyl, phenyl and 5- or 6-membered heteroaryl, wherein
$(C_3-C_6)$-cycloalkyl, 4- to 6-membered heterocycloalkyl, phenyl and 5- or 6-membered heteroaryl in their turn can in each case be substituted up to three times in an identical or different manner by fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkyl-amino, di-$(C_1-C_4)$-alkylamino, hydroxycarbonyl and/or $(C_1-C_4)$-alkoxycarbonyl,
and
$(C_1-C_6)$-alkyl can be substituted once to three times in an identical or different manner by fluorine, chlorine, bromine, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_6)$-alkoxycarbonyl, $(C_3-C_6)$-cycloalkyl, 4- to 6-membered heterocycloalkyl, phenyl and/or 5- or 6-membered heteroaryl,
(iv) $R^{12}$, $R^{15}$, $R^{16}$, $R^{18}$, $R^{20}$, $R^{22}$, $R^{23}$ and $R^{31}$ independently of one another for each individual occurrence represent a radical chosen from the series consisting of hydrogen and $(C_1-C_6)$-alkyl, wherein $(C_1-C_6)$-alkyl can be substituted once or twice in an identical or different manner by fluorine, chlorine, bromine, cyano, hydroxyl, trifluoromethoxy, $(C_1-C_4)$-alkoxy, amino, mono-$(C_1-C_4)$-alkylamino, di-$(C_1-C_4)$-alkyl-amino, hydroxycarbonyl and/or $(C_1-C_4)$-alkoxycarbonyl, and/or wherein
(v) $R^{11}$ and $R^{12}$, $R^{14}$ and $R^{15}$, $R^{16}$ and $R^{17}$, $R^{18}$ and $R^{19}$, $R^{20}$ and $R^{21}$, $R^{21}$ and $R^{22}$, $R^{23}$ and $R^{24}$ and $R^{30}$ and $R^{31}$ in each case paired together with the atoms to which they are bonded can form a 5- or 6-membered heterocycloalkyl ring, which can be substituted once or twice in an identical or different manner by fluorine, chlorine, bromine, cyano, $(C_1-C_4)$-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxy-carbonyl and/or ($C_1$-$C_4$)-alkoxycarbonyl, and
J denotes O or S,
and
$R^3$ represents hydrogen or methyl,
and their salts, solvates and solvates of the salts.

3. A compound of the formula (I) as claimed in claim 1, in which
$R^1$ represents a heteroaryl group of the formula

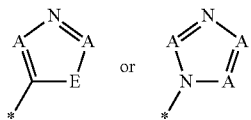

wherein
* denotes the linkage point with the dihydropyrazolone ring,
A in each individual occurrence denotes C—$R^4$ or N, wherein at most one of the ring members A represents N, wherein
$R^4$ in each individual case, independently of one another, represents hydrogen or a substituent chosen from the series consisting of fluorine, chlorine, bromine, cyano, nitro, ($C_1$-$C_6$)-alkyl, hydroxyl, ($C_1$-$C_6$)-alkoxy, trifluoromethoxy, amino, mono-($C_1$-$C_6$)-alkylamine, di-($C_1$-$C_6$)-alkylamino, hydroxycarbonyl and ($C_1$-$C_6$)-alkoxycarbonyl, wherein the ($C_1$-$C_6$)-alkyl radical mentioned in its turn can be substituted up to three times in an identical or different manner by fluorine, hydroxyl, trifluoromethoxy, ($C_1$-$C_4$)-alkoxy, amino, mono-($C_1$-$C_4$)-alkylamino, di-($C_1$-$C_4$)-alkyl-amino, hydroxycarbonyl and/or ($C_1$-$C_4$)-alkoxycarbonyl,
and
E denotes O or S,
$R^2$ represents a heteroaryl group of the formula

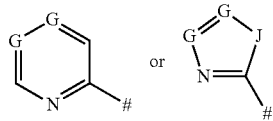

wherein
# denotes the linkage point with the dihydropyrazolone ring,
G in each case denotes C—$R^6$ or N, wherein not more than one of the two ring members G represents N, wherein
$R^6$ in each individual case, independently of one another, represents hydrogen or a substituent chosen from the series consisting of fluorine, chlorine, bromine, cyano, ($C_1$-$C_6$)-alkyl, ($C_3$-$C_6$)-cycloalkyl, 4- to 6-membered heterocycloalkyl, phenyl, 5- or 6-membered heteroaryl, —C(=O)—$OR^{10}$, —C(=O)—$NR^{11}R^{12}$, —$NR^{16}$—C(=O)—$R^{17}$, —$NR^{18}$—C(=O)—$ONR^{19}$, —$OR^{28}$ and —$NR^{30}R^{31}$, wherein
(i) ($C_1$-$C_6$)-alkyl in its turn can be substituted once to three times in an identical or different manner by radicals chosen from the series consisting of fluorine, ($C_3$-$C_6$)-cycloalkyl, 4- to 6-membered heterocycloalkyl, 5- or 6-membered heteroaryl, —C(=O)—$OR^{10}$, —C(=O)—$NR^{11}R^{12}$, —$NR^{16}$—C(=O)—$R^{17}$, —$NR^{18}$—C(=O)—$OR^{19}$, —$OR^{28}$ and —$NR^{30}R^{31}$,
wherein the cycloalkyl, heterocycloalkyl and heteroaryl radicals mentioned last in their turn can in each case be substituted up to twice in an identical or different manner by fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_6$)-alkylamino, di-($C_1$-$C_6$)-alkylamino, hydroxycarbonyl and/or ($C_1$-$C_4$)-alkoxycarbonyl,
(ii) ($C_3$-$C_6$)-cycloalkyl, 4- to 6-membered heterocycloalkyl, phenyl and 5- or 6-membered heteroaryl in their turn can in each case be substituted once or twice in an identical or different manner by fluorine, chlorine, bromine, cyano, ($C_1$-$C_6$)-alkyl, hydroxyl, ($C_1$-$C_4$)-alkoxy, trifluoro-methoxy, oxo, amino, mono-($C_1$-$C_4$)-alkylamino, di-($C_1$-$C_4$)-alkylamino, hydroxycarbonyl and/or ($C_1$-$C_4$)-alkoxycarbonyl,
wherein ($C_1$-$C_6$)-alkyl in its turn can be substituted up to three times in an identical or different manner by fluorine, hydroxyl, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and/or 5- or 6-membered heteroaryl,
(iii) $R^{10}$, $R^{11}$, $R^{17}$, $R^{19}$, $R^{28}$ and $R^{30}$ independently of one another for each individual occurrence represent a radical chosen from the series consisting of hydrogen, ($C_1$-$C_6$)-alkyl, ($C_3$-$C_6$)-cycloalkyl and 4- to 6-membered heterocycloalkyl, wherein
($C_3$-$C_6$)-cycloalkyl and 4- to 6-membered heterocycloalkyl in their turn can in each case be substituted up to three times in an identical or different manner by fluorine, ($C_1$-$C_4$)-alkyl, trifluoromethyl, hydroxyl, ($C_1$-$C_4$)-alkoxy, oxo, amino, mono-($C_1$-$C_4$)-alkylamino, di-($C_1$-$C_4$)-alkylamino, hydroxycarbonyl and/or ($C_1$-$C_4$)-alkoxycarbonyl
and
($C_1$-$C_6$)-alkyl can be substituted once to three times in an identical or different manner by fluorine, hydroxyl, ($C_1$-$C_4$)-alkoxy, amino, mono-($C_1$-$C_4$)-alkylamino, di-($C_1$-$C_4$)-alkylamino, hydroxy-carbonyl, ($C_1$-$C_4$)-alkoxycarbonyl, ($C_3$-$C_6$)-cycloalkyl, 4- to 6-membered heterocycloalkyl, phenyl and/or 5- or 6-membered heteroaryl,
(iv) $R^{12}$, $R^{16}$, $R^{18}$ and $R^{31}$ independently of one another for each individual occurrence represent a radical chosen from the series consisting of hydrogen and ($C_1$-$C_6$)-alkyl,
wherein ($C_1$-$C_6$)-alkyl can be substituted once or twice in an identical or different manner by fluorine, hydroxyl, ($C_1$-$C_4$)-alkoxy, amino, mono-($C_1$-$C_4$)-alkylamino, di-($C_1$-$C_4$)-alkylamino, hydroxycarbonyl and/or ($C_1$-$C_4$)-alkoxycarbonyl, and/or wherein (v) $R^{11}$ and $R^{12}$, $R^{16}$ and $R^{17}$, $R^{18}$ and $R^{19}$ and $R^{30}$ and $R^{31}$ in each case paired together with the atoms to which they are bonded can form a 5- or 6-membered heterocycloalkyl ring, which can be substituted once or twice in an identical or different manner by fluorine, $(C_1-C_4)$-alkyl, trifluoromethyl, hydroxyl, $(C_1-C_4)$-alkoxy, oxo, amino, mono-$(C_1-C_6)$-alkylamino, di-$(C_1-C_4)$-alkylamino, hydroxy-carbonyl and/or $(C_1-C_4)$-alkoxycarbonyl, and J denotes O or S, and $R^3$ represents hydrogen, and their salts, solvates and solvates of the salts.

4. A compound of the formula (I) as claimed in claim 1, in which $R^1$ represents a heteroaryl group of the formula

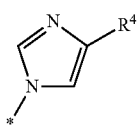

wherein

* denotes the linkage point with the dihydropyrazolone ring and $R^4$ denotes hydrogen, fluorine, chlorine, bromine, cyano, $(C_1-C_4)$-alkyl, trifluoromethyl, hydroxymethyl, $(C_1-C_4)$-alkoxy, trifluoromethoxy, hydroxycarbonyl or $(C_1-C_4)$-alkoxycarbonyl, $R^2$ represents a heteroaryl group of the formula

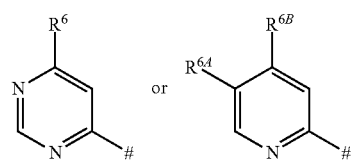

wherein # denotes the linkage point with the dihydropyrazolone ring and $R^6$, $R^{6A}$ and $R^{6B}$ are identical or different and independently of one another denote hydrogen or a substituent chosen from the series consisting of fluorine, chlorine, bromine, cyano, $(C_1-C_6)$-alkyl, trifluoro-methyl, hydroxyl, $(C_1-C_6)$-alkoxy, trifluoromethoxy, amino, mono-$(C_1-C_6)$-alkylamino, di-$(C_1-C_4)$-alkylamino, hydroxycarbonyl, $(C_1-C_4)$-alkoxycarbonyl and 4- to 6-membered heterocycloalkyl, wherein $(C_1-C_6)$-alkyl in its turn can be substituted by hydroxyl, $(C_1-C_4)$-alkoxy or amino and 4- to 6-membered heterocycloalkyl in its turn can be substituted once or twice in an identical or different manner by fluorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino, hydroxycarbonyl and/or $(C_1-C_4)$-alkoxycarbonyl, and $R^3$ represents hydrogen, and their salts, solvates and solvates of the salts.

5. 2-[5-(Hydroxymethyl)pyridin-2-yl]-4-[4-(trifluoromethyl)1H-imidazol-1-yl]-1,2-dihydro-3H-pyrazol-3-one according to claim 1 having the following formula

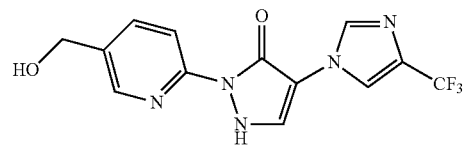 [SMILES: O=c1c(-n2cnc(C(F)(F)F)c2)c[nH]n1-c1ccc(CO)cn1]

and its salts, solvates and solvates of the salts.

6. A pharmaceutical composition comprising a compound according to claim 1 and an inert, non-toxic, pharmaceutically suitable auxiliary substance.

7. A pharmaceutical composition comprising the compound according to claim 5 and an inert, non-toxic, pharmaceutically suitable auxiliary substance.

8. A pharmaceutical composition comprising a compound according to claim 1 and one or more additional active compounds chosen from the group consisting of ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, tumor chemotherapeutics and antibiotics.

9. 2-[5-(Hydroxymethyl)pyridin-2-yl]-4-[4-(trifluoromethyl)-1H-imidazol-1-yl]-1,2-dihydro-3H-pyrazol-3-one according to claim 1 having the following formula

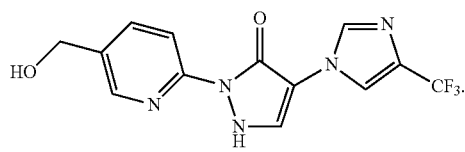 [SMILES: O=c1c(-n2cnc(C(F)(F)F)c2)c[nH]n1-c1ccc(CO)cn1]

10. 2-[5-(Hydroxymethyl)pyridin-2-yl]-4-[4-(trifluoromethyl)-1H-imidazol-1-yl]-1,2-dihydro-3H-pyrazol-3-one hydrochloride according to claim 1 having the following formula

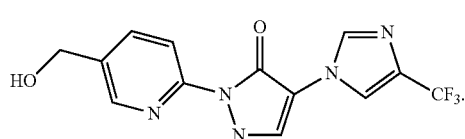

11. A pharmaceutical composition comprising the compound according to claim 9 and an inert, non-toxic, pharmaceutically suitable auxiliary substance.

12. A pharmaceutical composition comprising a compound according to claim 10 and an inert, non-toxic, pharmaceutically suitable auxiliary substance.

13. A process for the preparation of a compound of the formula (I) as defined in claim 1, characterized in that a compound of the formula (II)

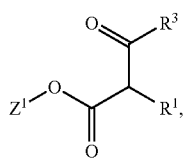
(II)

in which $R^1$ and $R^3$ in each case have the meanings given in claim 1 and
$Z^1$ represents methyl or ethyl,
is reacted in an inert solvent, optionally in the presence of an acid, with a compound of the formula (III)

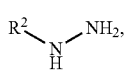
(III)

in which $R^2$ has the meaning given in claim 1,
to give compounds of the formula (IV)

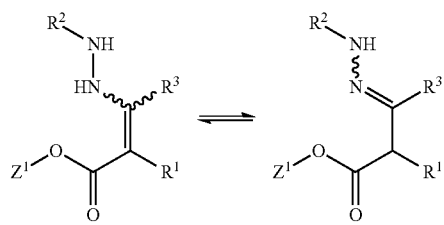
(IV)

in which $Z^1$, $R^1$, $R^2$ and $R^3$ have the meaning given in claim 1,
which cyclize already under these reaction conditions or in a subsequent reaction step under the influence of a base to give the compounds of the formula (I),
and the compounds of the formula (I) are optionally converted with the corresponding (i) solvents and/or (ii) bases or acids into their solvates, salts and/or solvates of the salts.

14. A process for the preparation of a compound of the formula (I) as defined in claim 1 in which $R^3$ denotes hydrogen, characterized in that a compound of the formula (V)

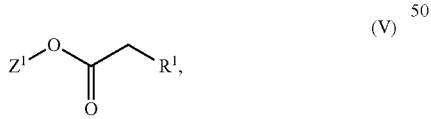
(V)

in which $R^1$ has the meaning given in claim 1 and
$Z^1$ represents methyl or ethyl,
is subjected to a condensation reaction with a compound of the formula (VI)

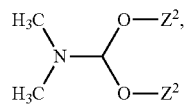
(VI)

in which
$Z^2$ represents methyl or ethyl,
to give compounds of the formula (VII)

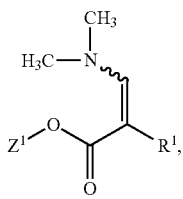
(VII)

in which $Z^1$ and $R^1$ have the meaning given in claim 1,
and these are subsequently reacted in the presence of an acid with a compound of the formula (III)

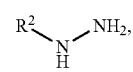
(III)

in which $R^2$ has the meaning given in claims 1,
to give compounds of the formula (IV-A)

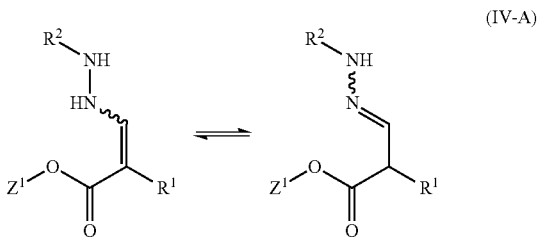
(IV-A)

in which $Z^1$, $R^1$ and $R^2$ have the meaning given in claim 1,
which cyclize already under these reaction conditions or in a subsequent reaction step under the influence of a base to give the compounds of the formula (I) wherein $R^3$ represents hydrogen.

* * * * *